(12) United States Patent
Hazard, III et al.

(10) Patent No.: US 10,918,413 B2
(45) Date of Patent: Feb. 16, 2021

(54) BEDSIDE STEREOTACTIC ULTRASOUND GUIDANCE DEVICE, SYSTEM AND METHOD

(71) Applicant: The Penn State Research Foundation, University Park, PA (US)

(72) Inventors: Sprague W. Hazard, III, Hummelstown, PA (US); Barry Fell, Harrisburg, PA (US); Randy Haluck, Lititz, PA (US); Pratik Rohatgi, Hummelstown, PA (US); Peter Dillon, Harrisburg, PA (US)

(73) Assignee: The Penn State Research Foundation, University Park (PA)

( * ) Notice: Subject to any disclaimer, the term of this patent is extended or adjusted under 35 U.S.C. 154(b) by 344 days.

(21) Appl. No.: 15/899,591

(22) Filed: Feb. 20, 2018

(65) Prior Publication Data
US 2018/0168682 A1 Jun. 21, 2018

Related U.S. Application Data

(63) Continuation-in-part of application No. PCT/US2016/047593, filed on Aug. 18, 2016.
(Continued)

(51) Int. Cl.
*A61B 17/34* (2006.01)
*A61B 90/11* (2016.01)
(Continued)

(52) U.S. Cl.
CPC .......... *A61B 17/3403* (2013.01); *A61B 5/065* (2013.01); *A61B 5/1076* (2013.01); *A61B 5/6852* (2013.01); *A61B 8/0808* (2013.01); *A61B 8/12* (2013.01); *A61B 34/20* (2016.02);

*A61B 34/30* (2016.02); *A61B 90/10* (2016.02); *A61B 90/11* (2016.02); *A61B 2017/00106* (2013.01); *A61B 2017/00398* (2013.01); *A61B 2017/00924* (2013.01); *A61B 2017/3407* (2013.01); *A61B 2017/3413* (2013.01); *A61B 2034/107* (2016.02); *A61B 2034/2059* (2016.02); *A61B 2034/2063* (2016.02); *A61B 2090/0811* (2016.02);
(Continued)

(58) Field of Classification Search
CPC .... A61B 90/10; A61B 90/11; A61B 2090/103
See application file for complete search history.

(56) References Cited

U.S. PATENT DOCUMENTS 4,681,103 A 7/1987 Boner
7,694,821 B1 4/2010 Asfora
(Continued)

FOREIGN PATENT DOCUMENTS

WO 2008153975 12/2008
WO 2009149398 12/2009
(Continued)

*Primary Examiner* — Todd J Scherbel
(74) *Attorney, Agent, or Firm* — Riverside Law LLP

(57) ABSTRACT

The present invention provides fixation devices, locking assemblies, and methods for using the same. The fixation devices of the invention are capable of accurate insertion of medical devices by providing detection means of a patient's internal anatomy and localizing a desired target. The devices are capable of locking into position to maintain accuracy.

11 Claims, 76 Drawing Sheets

Related U.S. Application Data

(60) Provisional application No. 62/206,636, filed on Aug. 18, 2015, provisional application No. 62/266,077, filed on Dec. 11, 2015, provisional application No. 62/550,764, filed on Aug. 28, 2017.

(51) Int. Cl.

| | | |
|---|---|---|
| *A61B 34/20* | (2016.01) | |
| *A61B 5/107* | (2006.01) | |
| *A61B 5/00* | (2006.01) | |
| *A61B 5/06* | (2006.01) | |
| *A61B 8/12* | (2006.01) | |
| *A61B 8/08* | (2006.01) | |
| *A61B 34/30* | (2016.01) | |
| *A61B 90/10* | (2016.01) | |
| *A61B 17/00* | (2006.01) | |
| *A61B 90/00* | (2016.01) | |
| *A61B 34/10* | (2016.01) | |

(52) U.S. Cl.
CPC ... *A61B 2090/103* (2016.02); *A61B 2090/364* (2016.02); *A61B 2090/367* (2016.02); *A61B 2090/378* (2016.02); *A61B 2090/3925* (2016.02)

(56) References Cited

U.S. PATENT DOCUMENTS

| | | |
|---|---|---|
| 8,845,656 B2 | 9/2014 | Skakoon |
| 2002/0019641 A1 | 2/2002 | Truwit |
| 2003/0187351 A1 | 10/2003 | Franck |
| 2007/0038100 A1 | 2/2007 | Nita |
| 2007/0191867 A1 | 8/2007 | Mazzocchi |
| 2008/0064960 A1* | 3/2008 | Whitmore, III ...... A61B 8/4218 600/459 |
| 2009/0171218 A1* | 7/2009 | Nygaard ............ A61B 10/0233 600/461 |
| 2009/0234369 A1* | 9/2009 | Bax ........................ A61B 90/11 606/130 |
| 2009/0306501 A1 | 12/2009 | Flint |
| 2010/0268308 A1 | 10/2010 | Rossby |
| 2011/0301451 A1 | 12/2011 | Rohling |
| 2013/0053867 A1 | 2/2013 | Gowda |
| 2013/0204316 A1 | 8/2013 | Carpentier |
| 2013/0345599 A1 | 12/2013 | Lin |
| 2014/0005542 A1 | 1/2014 | Bizzell |
| 2014/0074202 A1 | 3/2014 | Bedenbaugh |
| 2014/0155859 A1 | 6/2014 | Bonde |
| 2015/0164548 A1 | 6/2015 | Burg |
| 2015/0173793 A1 | 6/2015 | Flint |
| 2015/0202011 A1 | 7/2015 | Gowda |
| 2016/0100895 A1* | 4/2016 | Piferi .................... A61B 17/00 606/130 |
| 2017/0000521 A1 | 1/2017 | Bizzell |

FOREIGN PATENT DOCUMENTS

| | | |
|---|---|---|
| WO | 2010057315 | 5/2010 |
| WO | 2015066280 | 5/2015 |
| WO | 2017031340 | 2/2017 |

* cited by examiner

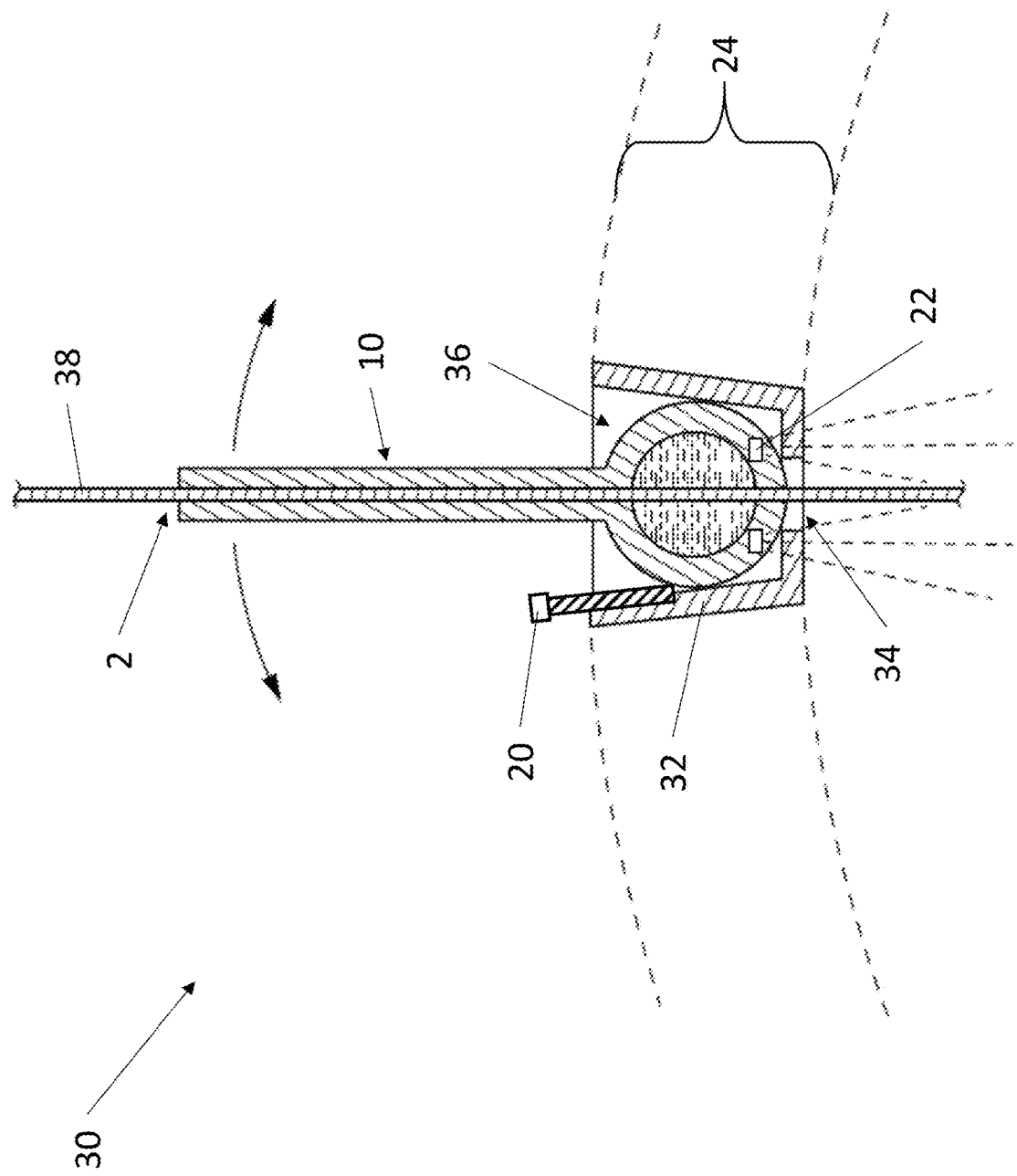

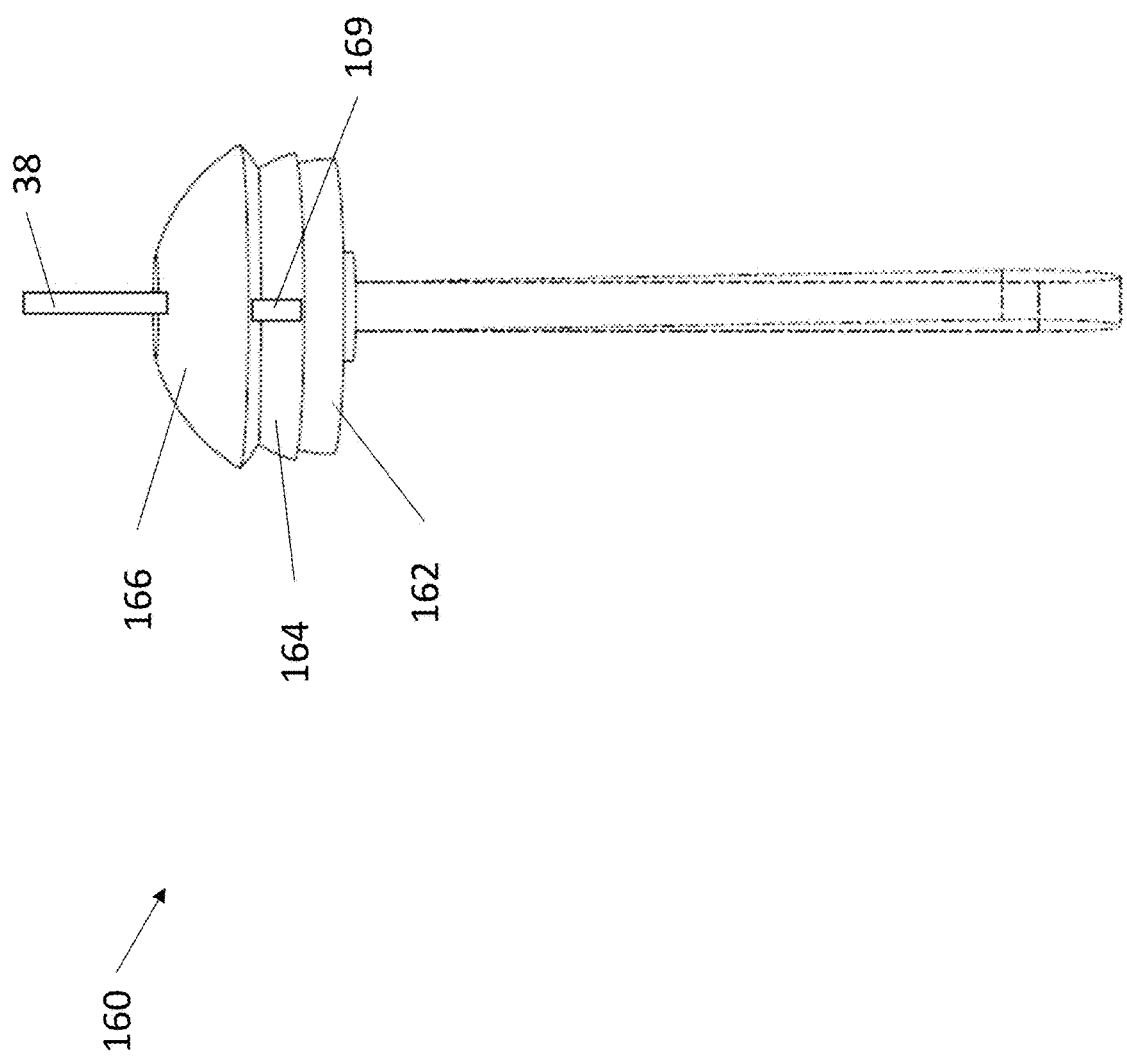

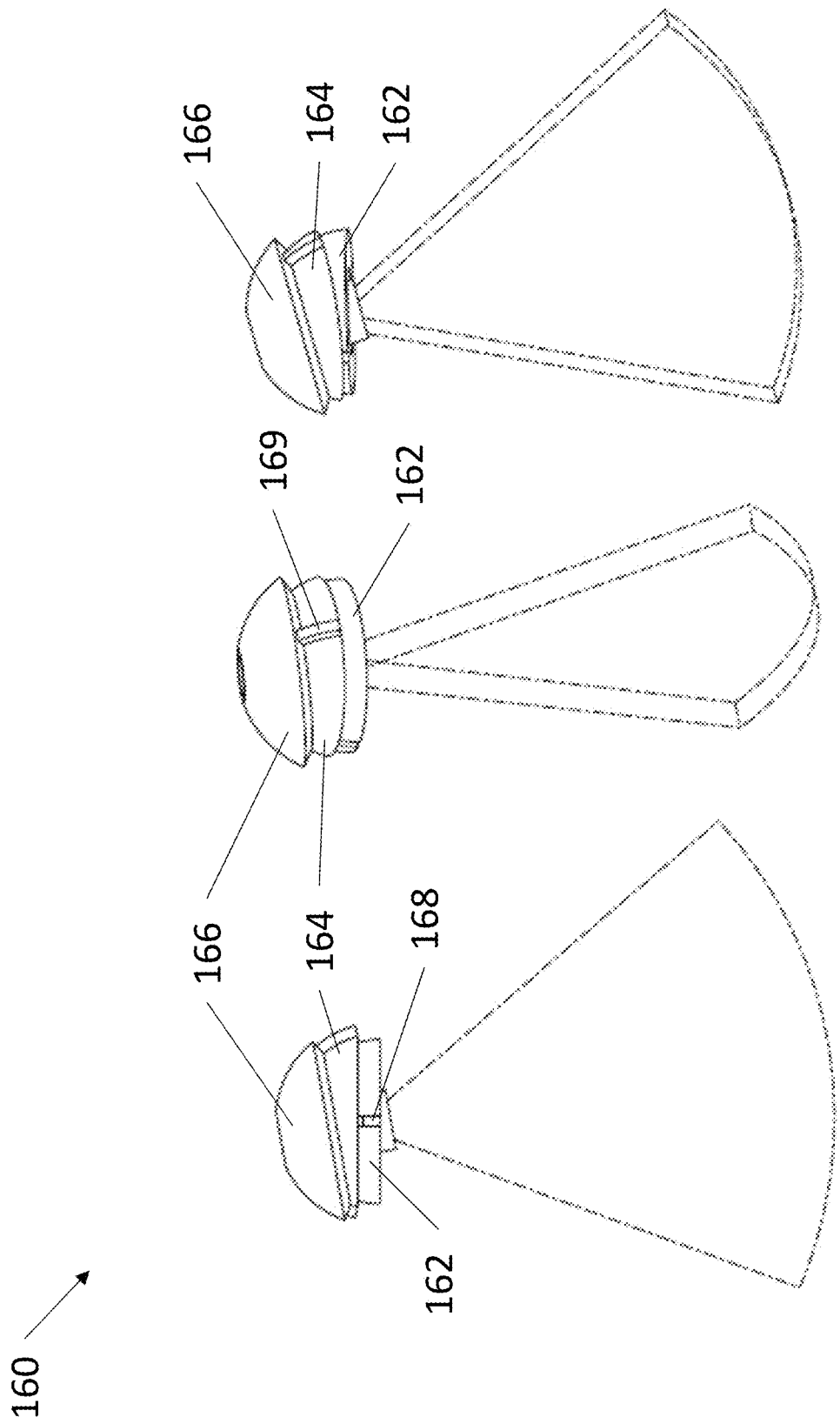

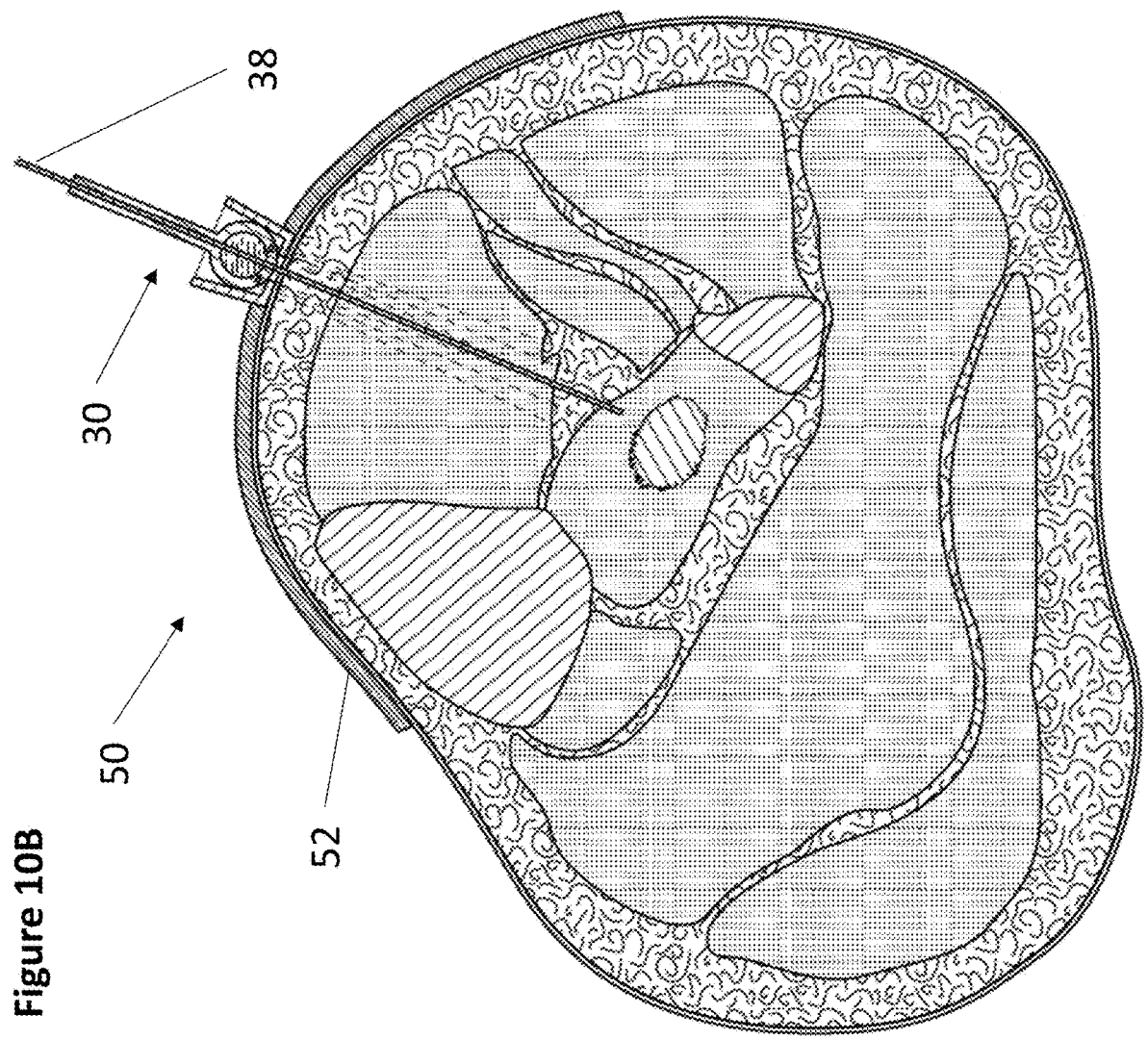
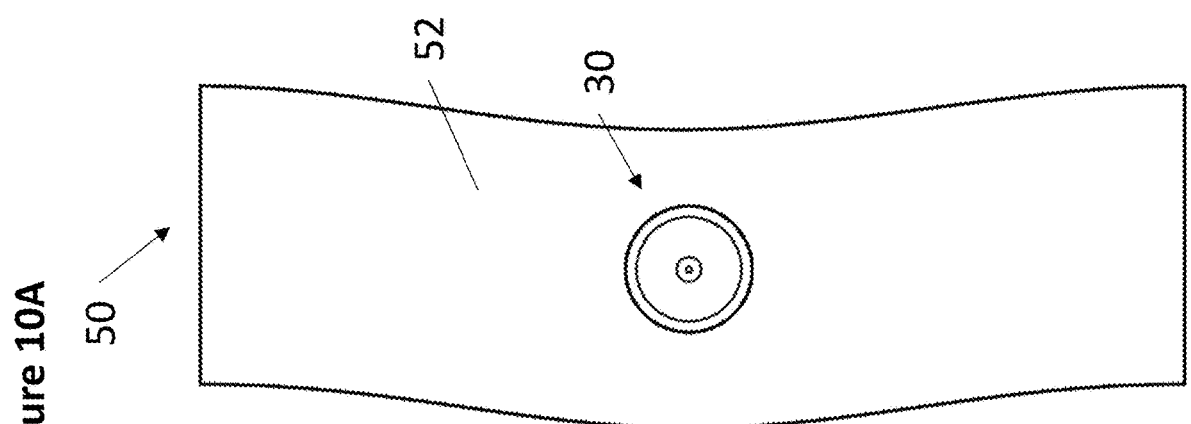
Figure 10B
Figure 10A

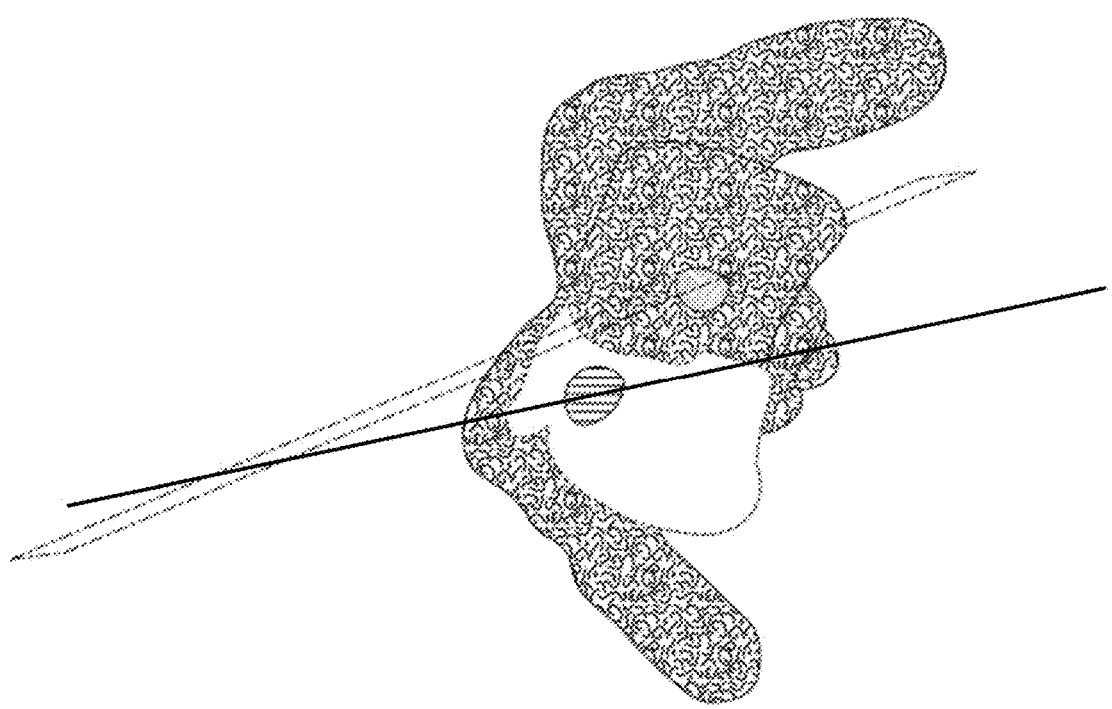

140

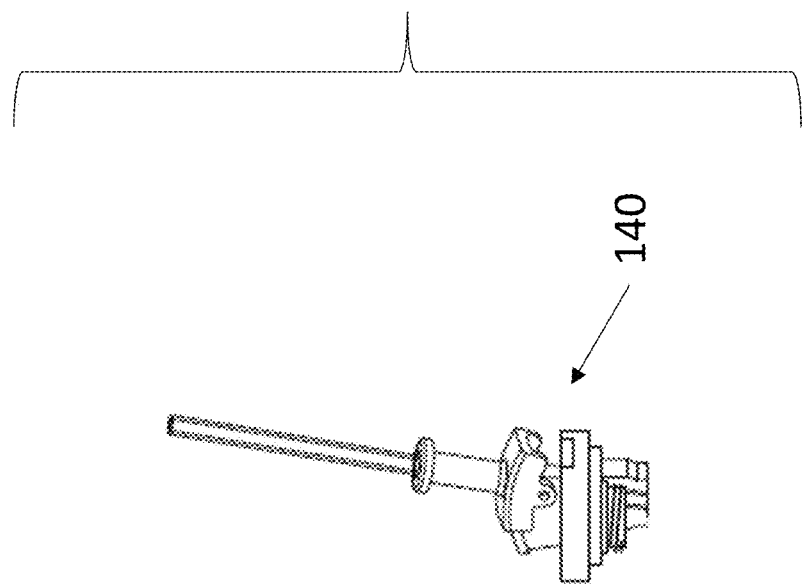
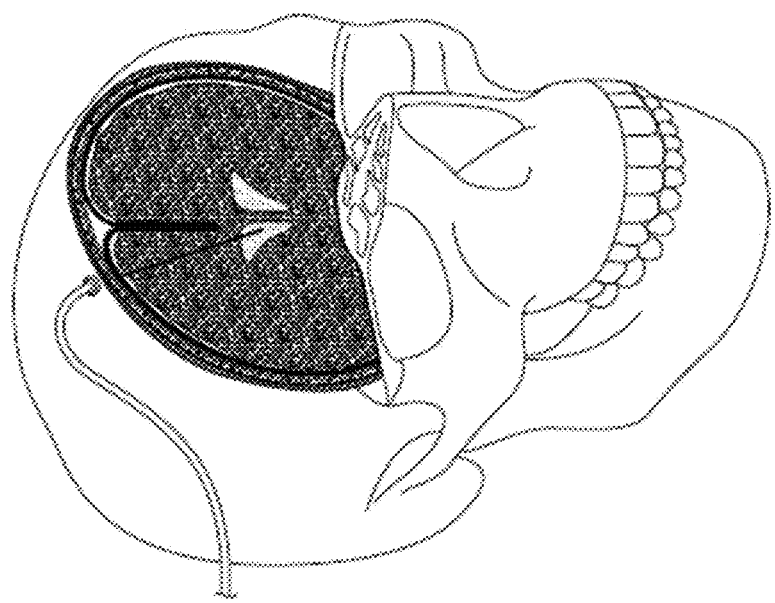
Figure 33

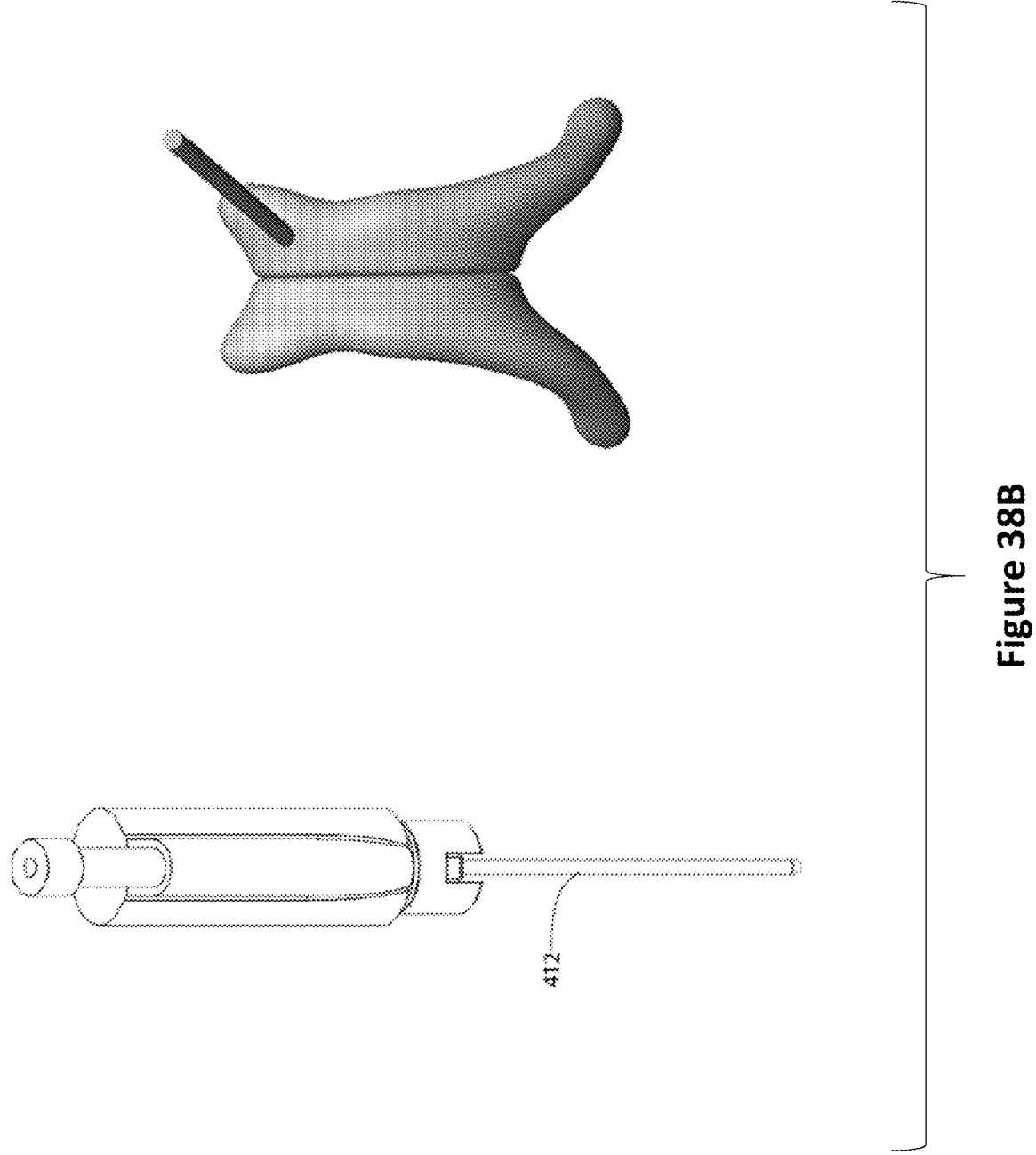

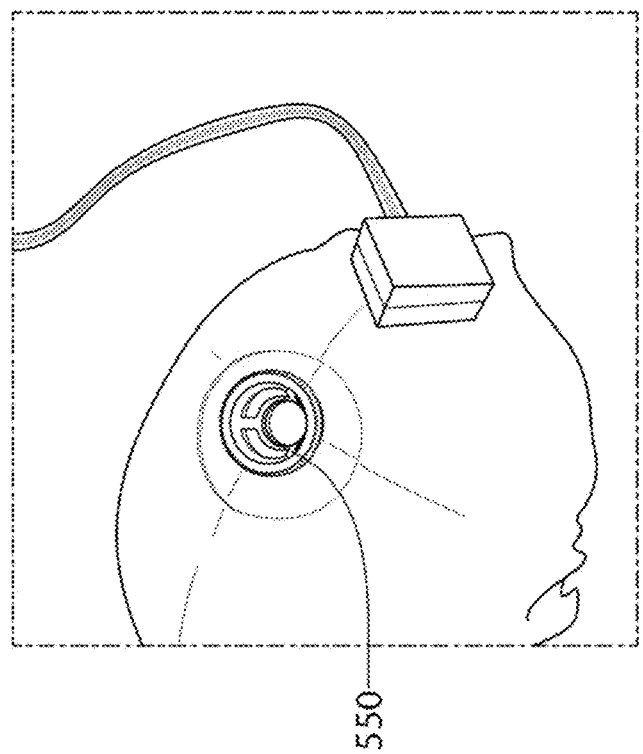
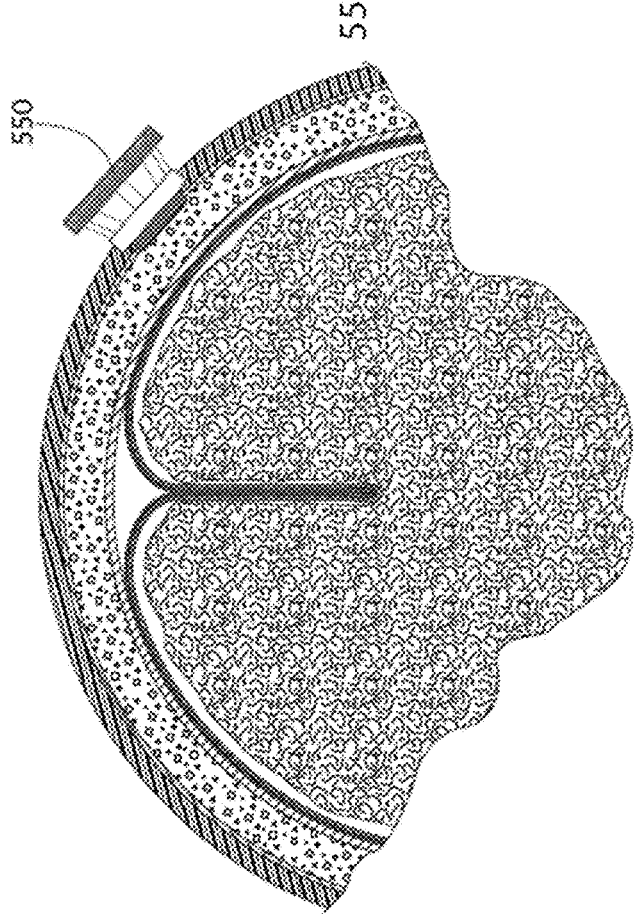
Figure 42B
Figure 42A

BEDSIDE STEREOTACTIC ULTRASOUND GUIDANCE DEVICE, SYSTEM AND METHOD

CROSS-REFERENCE TO RELATED APPLICATIONS

This application is a national stage filing and continuation-in-part of International Application No. PCT/US16/47593 filed on Aug. 18, 2016 and claims priority to U.S. Provisional Patent Application No. 62/206,636 filed Aug. 18, 2015, U.S. Provisional Patent Application No. 62/266,077 filed Dec. 11, 2015, and U.S. Provisional Patent Application No. 62/550,764 filed Aug. 28, 2017, the contents of which are incorporated by reference herein in their entireties.

BACKGROUND OF THE INVENTION

Stereotactic surgical procedures generally employ navigation equipment that utilizes optical and/or electromagnetic technologies. These technologies rely on previously obtained and processed images calibrated to patient landmarks. The systems are large, expensive, and have several parts that require a stable, unencumbered platform for use. In addition, practitioners have no navigational devices for use in unstable patients in the ICU who require precise placement of devices, such as external ventricular drains (EVD) to prevent ischemia or herniation. For example, EVDs are typically placed by neurosurgeons using anatomical landmarks to guide their passage. This technique relies heavily on the practitioner's skill level and may require multiple passes through normal, undamaged brain.

Some devices in the art employ features that attempt to improve device targeting and placement. These devices use a pivoting housing to stably hold a device for insertion. However, the housings generally do not have inherent imaging capabilities. As a result, the devices require the use of a separate imaging device, such as an ultrasound probe, to be used for the selection of a desired direction of insertion. The ultrasound probe must then be removed before the device can be inserted, and the operator is unable to visualize the device insertion without using another imaging device.

There is a need in the art for better devices and methods for accurate localization and intervention of targets within a patient. Further, there is a need for true "point of care" navigation that can continuously update imaging to reflect dynamic changes of the target location being imaged. The present invention meets this need.

SUMMARY OF THE INVENTION

The present invention provides fixation devices, locking assemblies, and methods for using the same. The fixation devices of the invention are capable of accurate insertion of medical devices by providing detection means of a patient's internal anatomy and localizing a desired target. The devices are capable of at least partially locking into position to maintain accuracy.

In one aspect, the invention relates to a fixation device comprising: an elongate body having a proximal end opening, a distal end opening, and a lumen connecting the proximal and distal end openings; at least one emission means at a distal end region of the elongate body; and at least one receiving means for receiving at least some emissions from said emission means.

In one embodiment, the elongate body lumen is sized suitably for an instrument, tool, implant, or biological material to pass therethrough. In one embodiment, the elongate body lumen is sized suitably for an inserted instrument, tool, implant, or biological material to rotate. In one embodiment, the elongate body lumen has a cross-section that is circular, elliptical, polygonal, or keyed. In one embodiment, the elongate body lumen may be centered or off-center in the elongate body.

In one embodiment, the emission means are selected from the group consisting of: ultrasonic transducers, optical sensors, thermal sensors, electromagnetic sensors, photoelectric transducers, laser diodes, radio transducers, Doppler, x-ray, particle sensors, chemical sensors, and piezoelectric sensors. In one embodiment, the ultrasonic transducers are either piezoelectric ultrasonic transducers or capacitive ultrasonic transducers. In one embodiment, the distal end region of the elongate body is composed of a material which is at least partially transmissive to said emission.

In one embodiment, the device further comprises: a grommet having a proximal end opening, a distal end opening, and a lumen connecting the proximal and distal end openings; and at least one locking member; wherein the grommet lumen is sized such that the elongate body of the fixation device can pass through the grommet lumen and be at least partially locked into place by the at least one locking member.

In one embodiment, the grommet comprises one or more materials selected from the group consisting of: metals, ceramics, and polymers. In one embodiment, the grommet comprises one or more materials selected from the group consisting of: stainless steel, cobalt, titanium, aluminum oxide, zirconia, calcium phosphate, silicon, polyethylene, polyvinyl chloride, polyurethane, and polylactide.

In one embodiment, the device further comprises: a cup having a base member and perimeter sidewalls forming an open top, wherein the base member includes at least one opening, and at least one locking member; wherein the cup is sized such that the distal end region of the elongate body of the fixation device can be at least partially locked into place within the cup by the at least one locking member.

In one embodiment, the cup comprises one or more materials selected from the group consisting of: metals, ceramics, and polymers. In one embodiment, wherein the cup comprises one or more materials selected from the group consisting of: stainless steel, cobalt, titanium, aluminum oxide, zirconia, calcium phosphate, silicon, polyethylene, polyvinyl chloride, polyurethane, and polylactide. In one embodiment, the at least one locking member is selected from the group consisting of: a screw, a bolt, a pin, an adhesive, and a clamp. In one embodiment, the at least one locking member is engaged mechanically, electro-mechanically, magnetically, or adhesively.

In one embodiment, the device further comprises an anchoring patch comprising: a flexible substrate having a first and a second surface; and a rigid housing positioned within the flexible substrate; wherein the housing is dimensioned to engage the devices of the present invention.

In one embodiment, the flexible substrate comprises a material selected from the group consisting of plastics, polymers, metals, and gels. In one embodiment, the device further comprises an adhesive material on at least a portion of the first surface of the flexible substrate.

In one embodiment, the device further comprises a first angled shim housing having a space at its center and a cranial burr anchor, wherein the first angled shim housing is attached to the cranial burr anchor, wherein the fixation device fits within and is rotatable within the space of the first angled shim housing, and the first angled shim housing is rotatable about the cranial burr anchor.

In one embodiment, the device further comprises a second angled shim housing, wherein the second angled shim housing is attached between the first angled shim housing and the cranial burr anchor, and wherein the second angled shim housing is rotatable about the first angled shim housing and the cranial burr anchor.

In one embodiment, the device further comprises a lever attachment having a lumen attached to and continuous with the lumen of the fixation device, wherein the lumen of the lever attachment is sized to accept a medical instrument.

In one embodiment, the device further comprises a rotatable housing, a cranial burr anchor, and a lever attachment having a lumen connected to the proximal end opening of the fixation device, wherein the rotatable housing is attached to the cranial burr anchor, wherein the fixation device is encased and rotatable within the rotatable housing, wherein the rotatable housing is rotatable about the cranial burr anchor, and wherein the lumen of the lever attachment is sized to accept a medical instrument.

In one embodiment, the device further comprises a cranial interface component having at least two angular rails, an anterior-posterior angle control component having at least two angular rails, a lateral angle control component having a space at its center, and a lever attachment having a lumen connected to the proximal opening of the fixation device, wherein the anterior-posterior angle control component is movable along the at least two angular rails of the cranial interface component, wherein the lateral angle control component is movable along the at least two angular rails of the anterior-posterior angle control component, wherein the fixation device fits within and is rotatable within the space of the lateral angle control component, and wherein the lumen of the lever attachment is sized to accept a medical instrument.

In one embodiment, the device further comprises a hemispherical cap having a first track and a hemispherical cranial burr anchor having a second track, wherein the first track spans the diameter of the hemispherical cap, wherein the second track spans the diameter of the hemispherical cranial burr anchor, wherein the hemispherical cap is movable along the second track, wherein the fixation device is movable along the first track, and wherein the first track and the second track are perpendicular to each other.

In another aspect, the present invention relates to a method of localizing and interacting with a target site within a patient's anatomy, comprising the steps of: attaching the device of the present invention to the patient's body near the target site; generating emissions using the attached device; receiving the emissions from the attached device; adjusting the orientation of the attached device to aim the attached device at the target site; at least partially locking the attached device; determining a target site first boundary having a minimum depth and a target site second boundary having a maximum depth; and inserting medical devices through the lumen of the attached device to interact with the target site such that the medical devices pass the minimum depth but do not exceed the maximum depth.

In another aspect, the present invention relates to a method for accurate insertion of an external ventricular drain (EVD), comprising the steps of: inserting the device of the present invention into a burr hole in a patient's skull; imaging a region within the patient's brain using the attached device; aligning the lumen of the attached device with a desired site of drainage; at least partially locking the attached device in place; determining a desired site of drainage first boundary having a minimum depth and a desired site of drainage second boundary having a maximum depth; and guiding an EVD through the lumen of the attached device into the desired site of drainage for draining such that the EVD passes the minimum depth but does not exceed the maximum depth. In one embodiment, an ultrasonic reflective strip is attached to the EVD.

In another aspect, the present invention relates to a method for accurate insertion of a medical device to a target site, comprising the steps of: affixing an anchoring patch having a flexible substrate and a rigid housing onto a patient at a desired site of insertion of a medical device; engaging the device of claim 9 or 12 to the rigid housing of the anchoring patch; aligning the lumen of the attached device with the target site; at least partially locking the attached device in place; determining a target site first boundary having a minimum depth and a target site second boundary having a maximum depth; and guiding the medical device through the lumen of the attached device to the target site such that the medical device passes the minimum depth but does not exceed the maximum depth.

In one embodiment, the medical device is selected from the group consisting of: catheters, microforceps, microscalpels, biopsy needles, radiofrequency ablation probes, cryoablation probes, suturing instruments, and syringes. In one embodiment, an ultrasonic reflective strip is attached to the medical device.

In another aspect, the present invention relates to a method of stereotactic mapping; comprising the steps of: attaching at least two devices of the present invention to a patient's body; generating emissions using at least one of the attached devices; and receiving the emissions using at least one of the attached devices.

In another aspect, the present invention relates to a method of using a fixation device to insert a ventricular catheter into a subject's brain, comprising the steps of: marking the skin at Kocher's point above a subject's skull; making an incision at the marked skin; perforating the skull; inserting a fixation device having ultrasonic transducers; aligning the ultrasonic transducers to capture a cross-sectional ultrasound image of the brain and the positional, angular, and rotational orientation of the ultrasonic transducers; actuating the ultrasonic transducers; acquiring a series of ultrasonic images of the brain and associated positional, angular, and rotational orientation of the ultrasonic transducers during actuation; assembling the ultrasonic images into a 3D reconstruction of the brain ventricles using the associated positional, angular, and rotational orientation of the ultrasonic transducers; performing an automatic segmentation of the 3D reconstruction to isolate an anatomy of interest; acquiring the positional, angular, and rotational orientation of the anatomy of interest; aligning the fixation device to target the anatomy of interest; fixing the alignment of the fixation device relative to the skull; inserting a catheter and ventricular drain through the fixation device into the anatomy of interest; and removing the fixation device over the catheter and ventricular drain.

In another aspect, the present invention relates to a fixation device comprising: an elongate body having a proximal end opening, a distal end opening, and a lumen connecting the proximal and distal end openings; a first angled shim housing having a space at its center; and a cranial burr anchor; wherein the first angled shim housing is attached to the cranial burr anchor, wherein the elongate body fits within and is rotatable within the space of the first angled shim housing, and wherein the first angled shim housing is rotatable about the cranial burr anchor.

In another aspect, the present invention relates to a fixation device comprising: an elongate body having a proximal end opening, a distal end opening, and a lumen connecting the proximal and distal end openings; a first angled shim housing having a space at its center; a second angled shim housing; and a cranial burr anchor; wherein the first angled shim housing is attached to the second angled shim housing, wherein the second angled shim housing is attached to the cranial burr anchor, wherein the elongate body fits within and is rotatable within the space of the first angled shim housing, wherein the first angled shim housing is rotatable about the second angled shim housing, and wherein the second angled shim housing is rotatable about the cranial burr anchor.

In another aspect, the present invention relates to a fixation device comprising: an elongate body having a proximal end opening, a distal end opening, and a lumen connecting the proximal and distal end openings; a first angled shim housing having a space at its center; a lever attachment having a lumen; and a cranial burr anchor; wherein the lever attachment is attached to the first angled shim housing, wherein the first angled shim housing is attached to the cranial burr anchor, wherein the lumen of the elongate body is attached to and continuous with the lumen of the lever attachment, wherein the elongate body fits within and is rotatable within the space of the first angled shim housing, and wherein the first angled shim housing is rotatable about the cranial burr anchor.

In another aspect, the present invention relates to a fixation device comprising: an elongate body having a proximal end opening, a distal end opening, and a lumen connecting the proximal and distal end openings; a rotatable housing; a cranial burr anchor; and a lever attachment having a lumen attached to and continuous with the lumen of the elongate body; wherein the rotatable housing is attached to the cranial burr anchor, wherein the elongate body is encased and rotatable within the rotatable housing, wherein the rotatable housing is rotatable about the cranial burr anchor, and wherein the lumen of the lever attachment is sized to accept a medical instrument.

In another aspect, the present invention relates to a fixation device comprising: an elongate body having a proximal end opening, a distal end opening, and a lumen connecting the proximal and distal end openings; a cranial interface component having at least two angular rails; an anterior-posterior angle control component having at least two angular rails; a lateral angle control component having a space at its center; and a lever attachment having a lumen attached to and continuous with the lumen of the elongate body; wherein the anterior-posterior angle control component is movable along the at least two angular rails of the cranial interface component, wherein the lateral angle control component is movable along the at least two angular rails of the anterior-posterior angle control component, wherein the elongate body fits within and is rotatable within the space of the lateral angle control component, and wherein the lumen of the lever attachment is sized to accept a medical instrument.

In another aspect, the present invention relates to a fixation device comprising: an elongate body having a proximal end opening, a distal end opening, and a lumen connecting the proximal and distal end openings; a hemispherical cap having a first track; and a hemispherical cranial burr anchor having a second track; wherein the first track spans the diameter of the hemispherical cap, wherein the second track spans the diameter of the hemispherical cranial burr anchor, wherein the hemispherical cap is movable along the second track, wherein the elongate body is movable along the first track, and wherein the first track and the second track are perpendicular to each other.

In another aspect, the present invention relates to a kit comprising: the device of the present invention; a hair clipper; a tape measure; a surgical marking implement; skin preparation material; a scalpel; and a drilling instrument.

In one embodiment, the kit further comprises display equipment. In one embodiment, the kit further comprises a portable power source.

In another aspect, the present invention relates to a kit comprising: a devices of any of claims 34-39; a power source; a hair clipper; a tape measure; a surgical marking implement; skin preparation material; a scalpel; and a drilling instrument.

In one embodiment, the kit further comprises at least one emission means and at least one receiving means for receiving at least some emissions from said emission means. In one embodiment, the kit further comprises display equipment. In one embodiment, the kit further comprises a portable power source.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements, geometry, and instrumentalities of the embodiments shown in the drawings.

FIG. 3 depicts an exemplary fixation device coupled with a cup locking assembly.

FIG. 9A through FIG. 9D depict an exemplary compact 4 DoF device.

FIG. 10A and FIG. 10B depict (FIG. 10A) an exemplary fixation device coupled with a cup locking assembly and an anchoring patch and (FIG. 10B) a schematic depicting a cross sectional view of the entire assembly adhered to a patient's calf.

FIG. 14A and FIG. 14B depict the malplacement of a shunt in a three dimensional model of the ventricles of a brain. Wherein the goal of a ventriculostomy is to deliver the shunt (solid line) to the anterior ipsilateral horn of the ventricle by transiting the burr location on the cranium known as Kocher's point, the traditional free-hand technique via a trajectory normal to the cranium surface (dashed line)

is prone to malplacement of the shunt into the contralateral ventricle or other, less desirous or contrary locations.

Figure 14A:
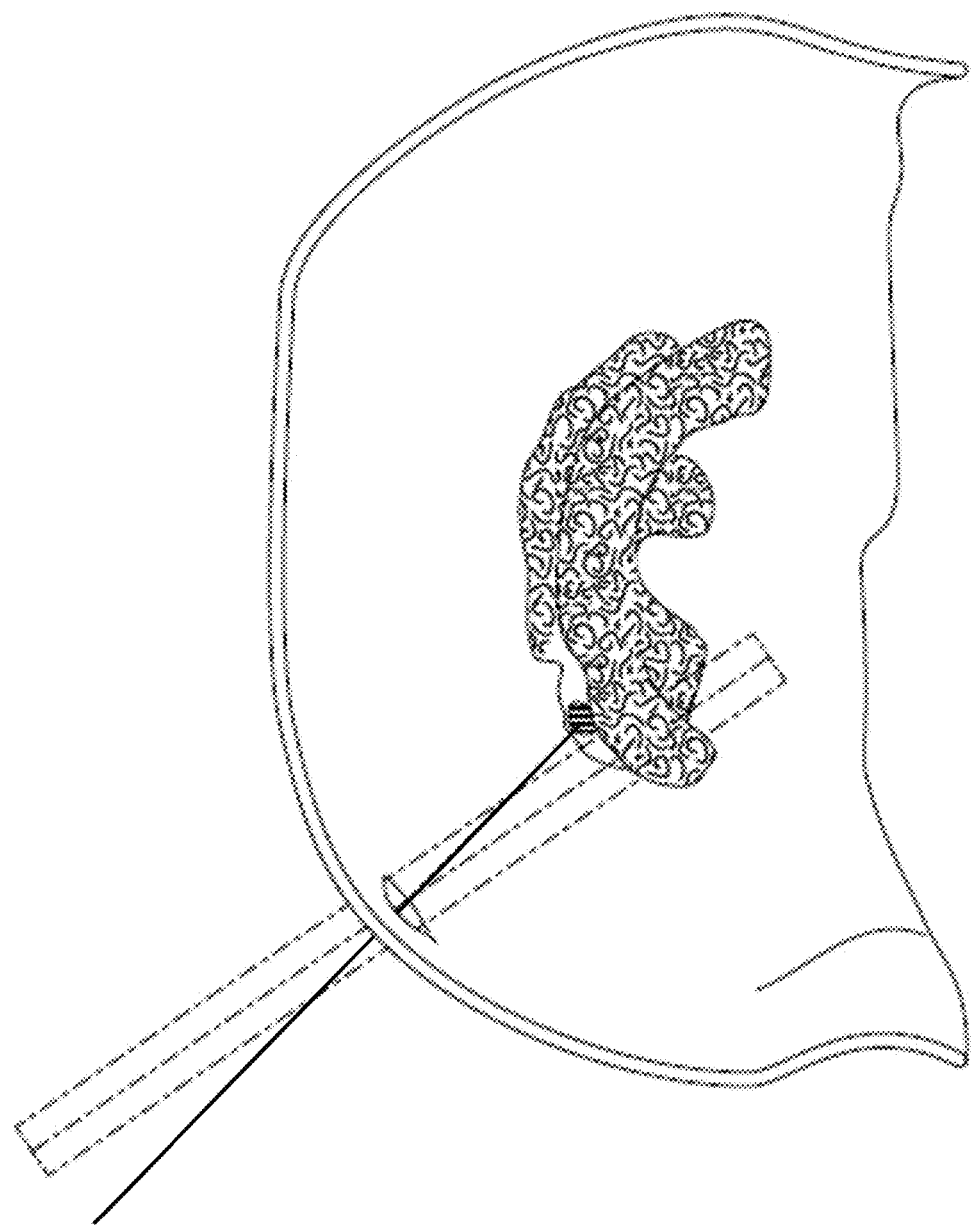
Figure 15C:
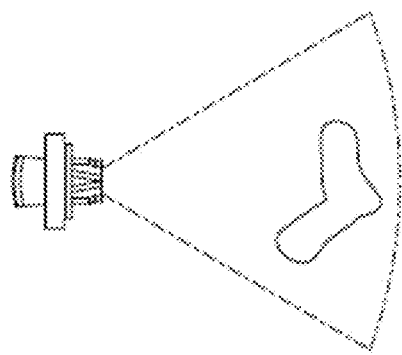
Figure 15F:
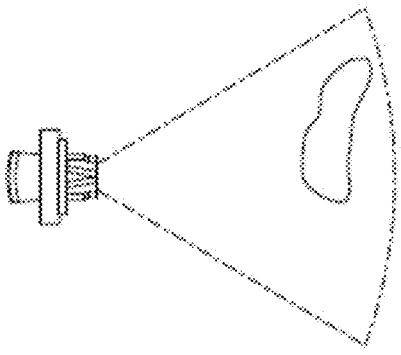
Figure 15B:
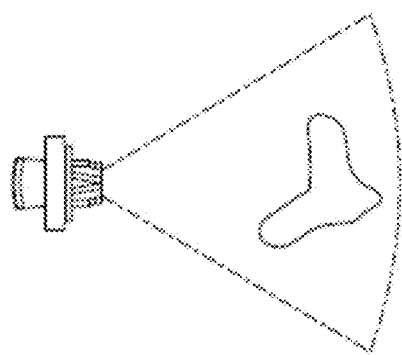
Figure 15E:
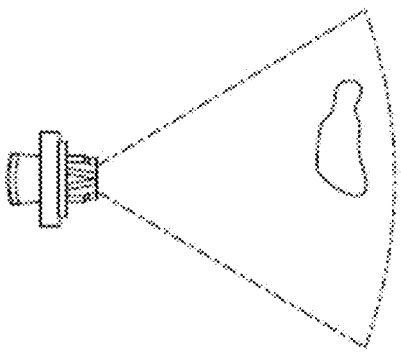
Figure 15A:
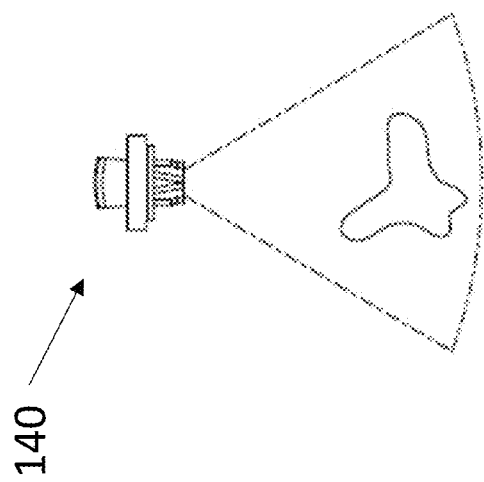
Figure 15D:
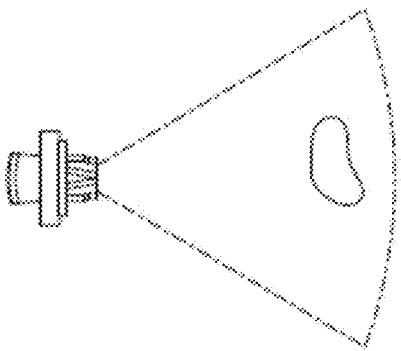

FIG. 15A through FIG. 15F depict a method of stepwise rotation of an ultrasound transducer to generate the three-dimensional model of the ventricles depicted in FIG. 14A and FIG. 14B. FIG. 15A: initial position; FIG. 15B: 15 degree rotation from initial; FIG. 15C: 30 degree rotation from initial; FIG. 15D: 45 degree rotation from initial; FIG. 15E: 60 degree rotation from initial: FIG. 15F: 75 degree rotation from initial.

Figure 16:
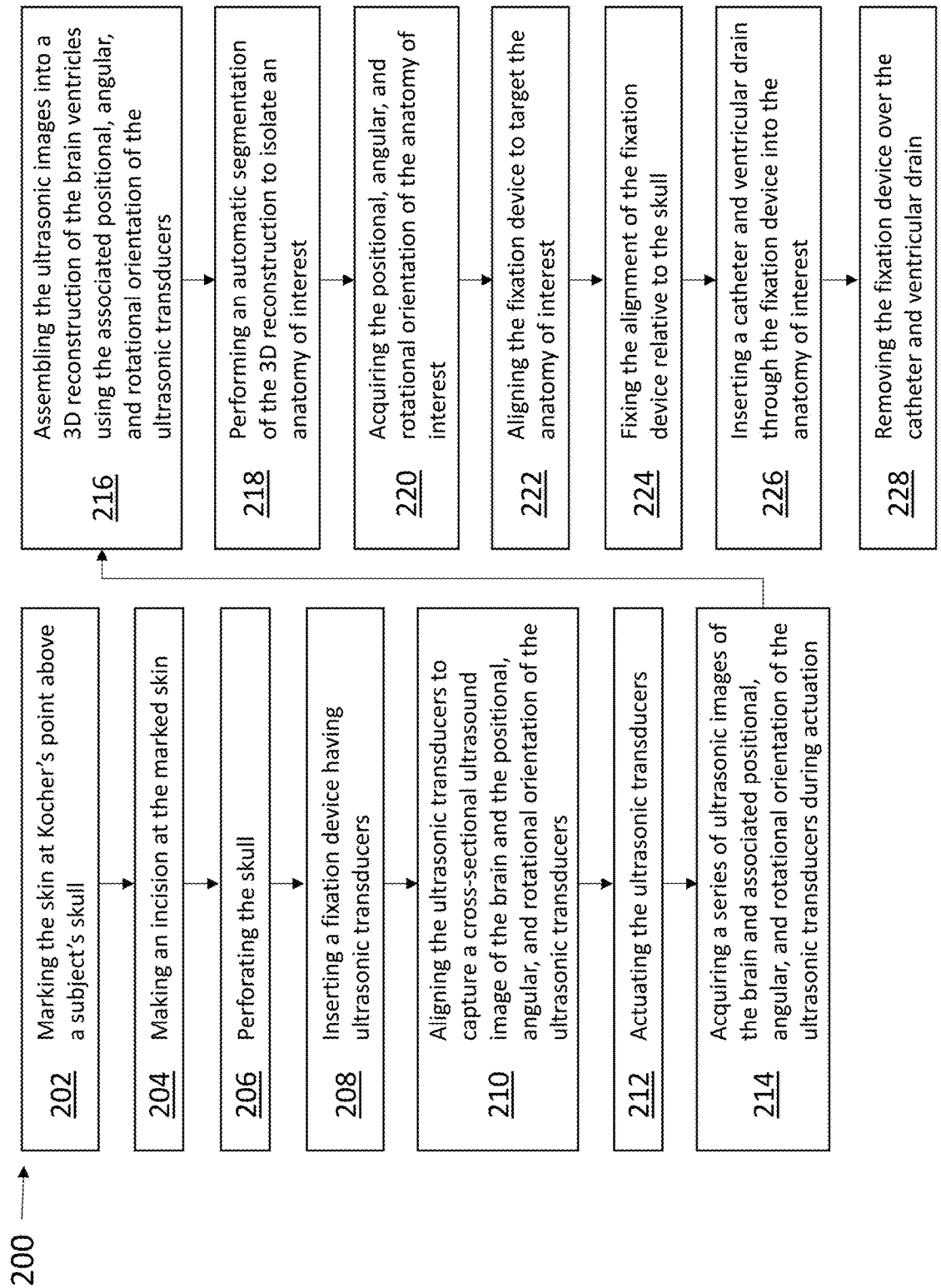

FIG. 16 is a flowchart for an exemplary method of using a fixation device to insert a ventricular drain.

Figure 17:
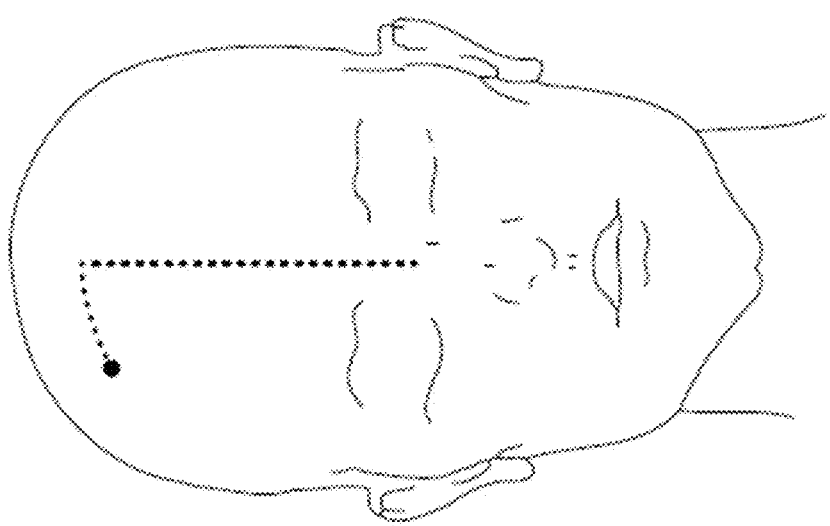

FIG. 17 depicts an exemplary method of marking the skin by locating the point between the pupils (nasion), drawing a line 10 cm from the nasion along the skull heading posterior to the occiput, and measuring 3 cm laterally.

Figure 18:
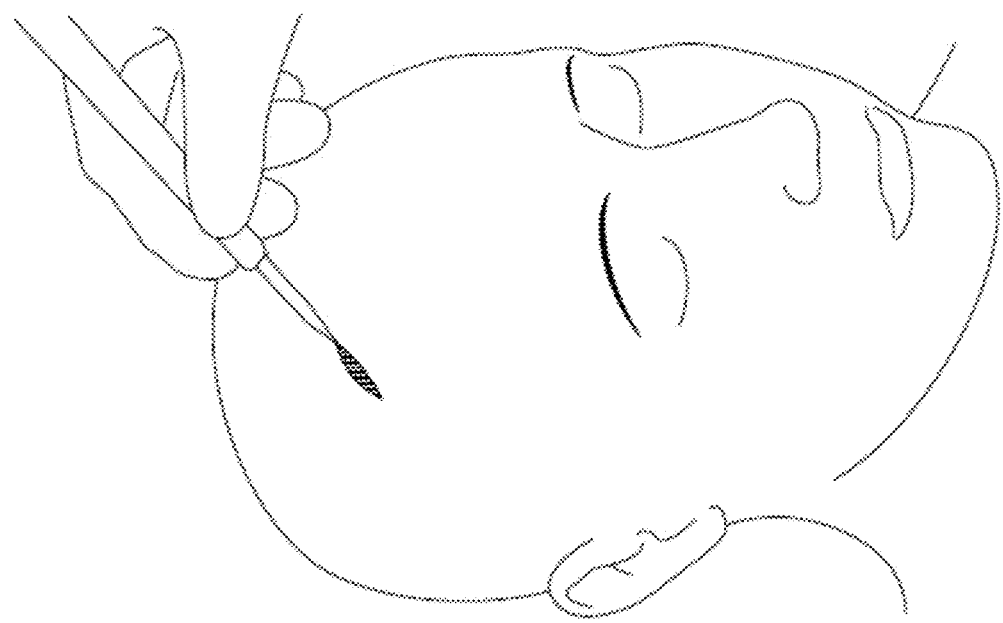

FIG. 18 depicts an exemplary method of making an incision at the skin marked in FIG. 17.

Figure 19:
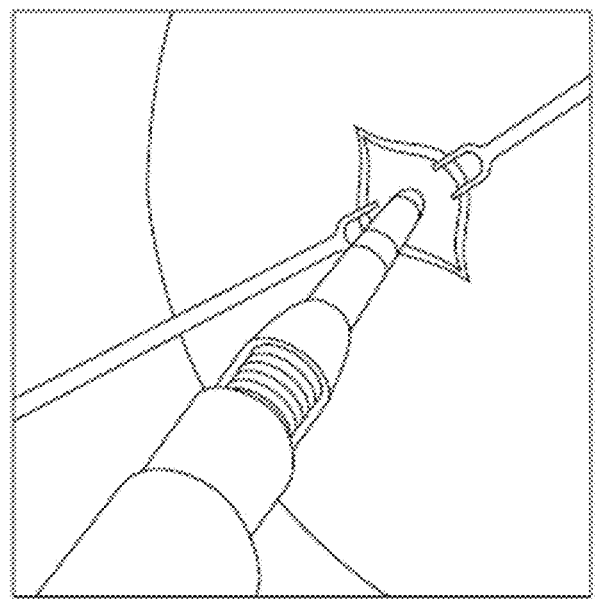

FIG. 19 depicts an exemplary method of perforating the skull at the incision made in FIG. 18.

Figure 20:
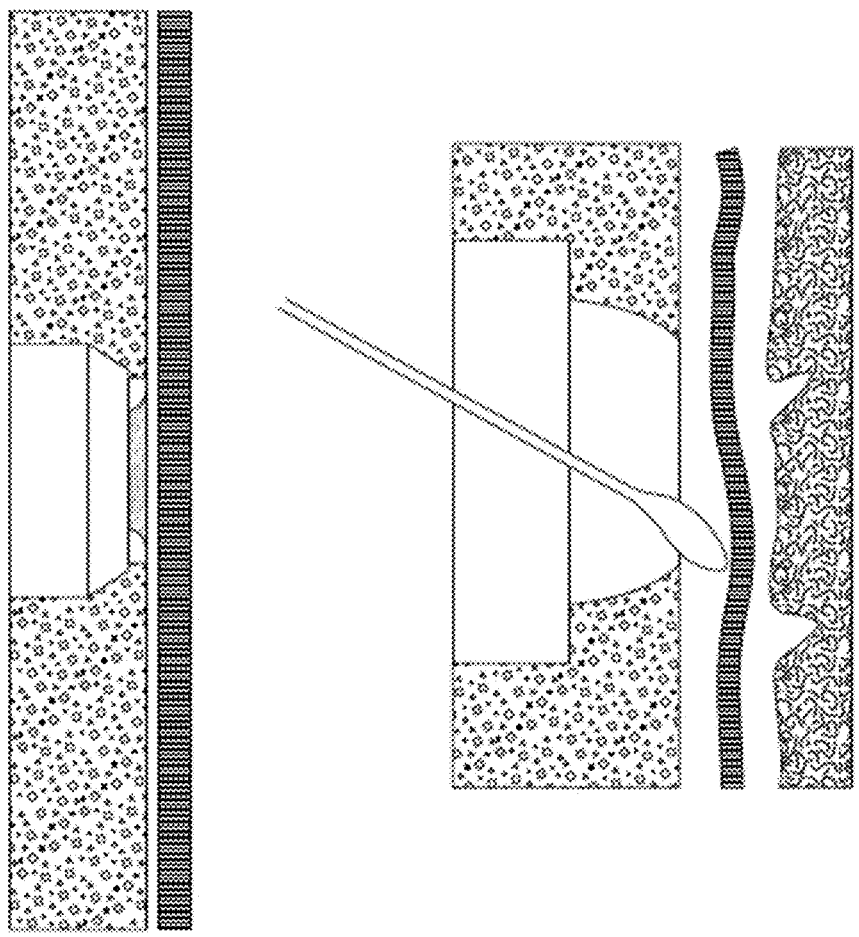

FIG. 20 depicts an exemplary skull perforation dimensioned to fit a device of the present invention.

Figure 21:
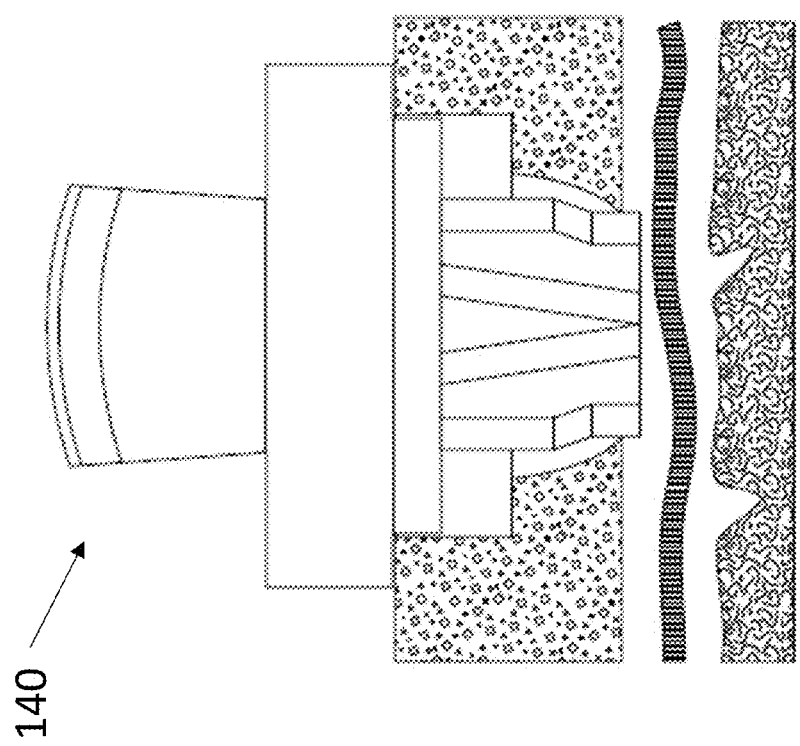

FIG. 21 depicts the insertion of a device of the present invention into a skull perforation.

Figure 22:
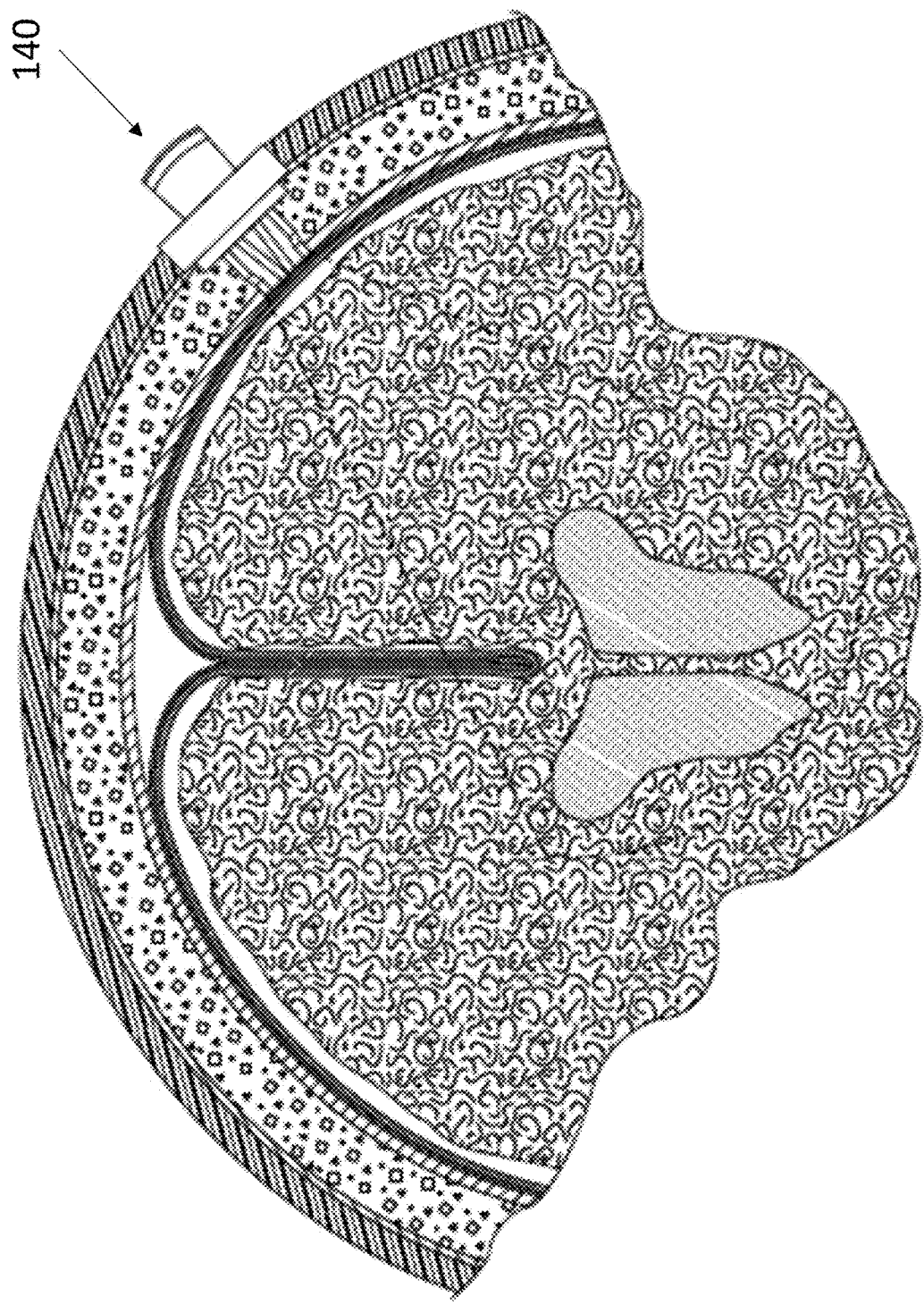

FIG. 22 depicts a device of the present invention inserted into a skull perforation.

Figure 23:
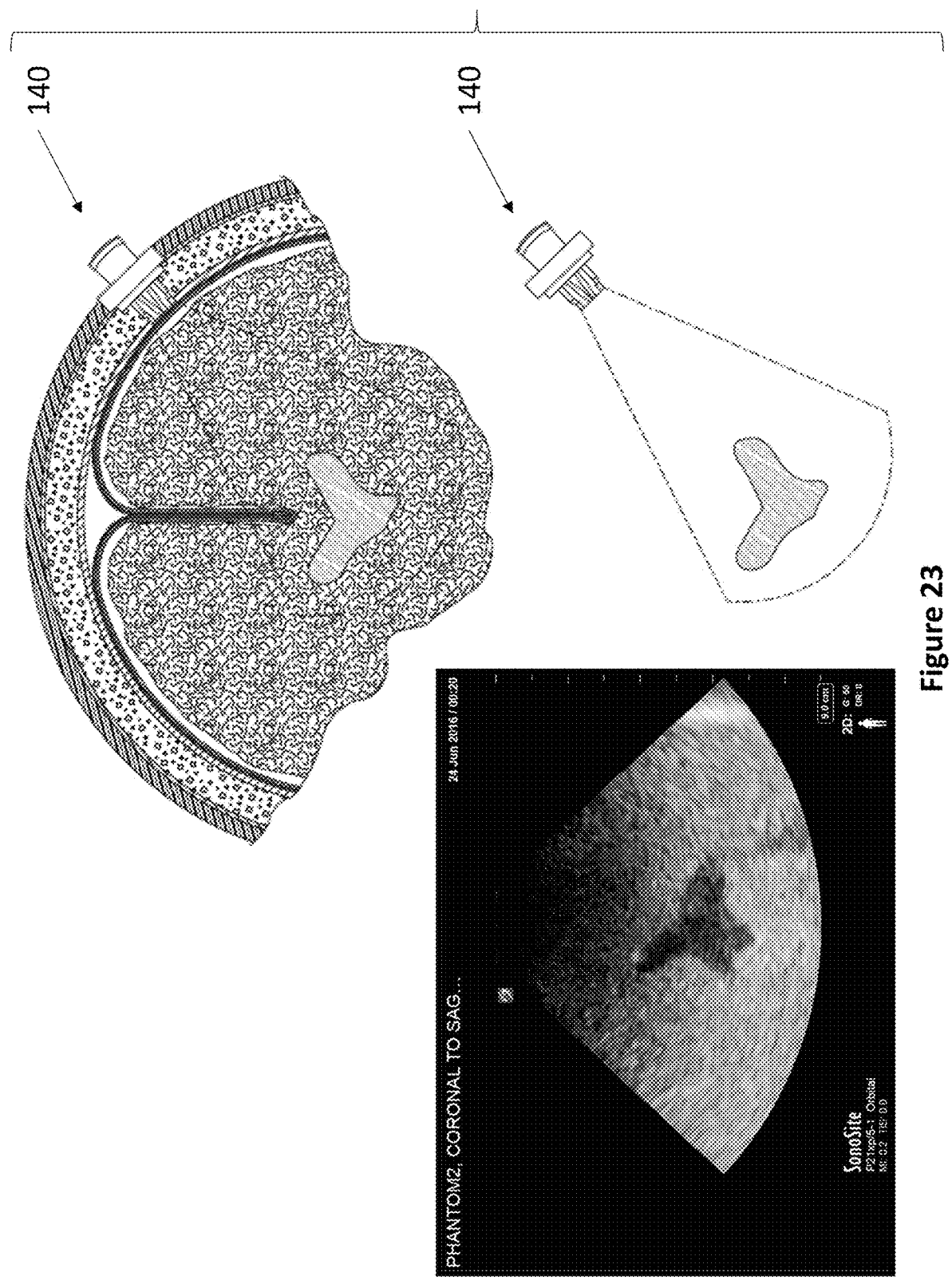

FIG. 23 depicts an exemplary alignment of a device of the present invention to capture a cross-sectional ultrasound image of the ventricles of the brain.

Figure 24:
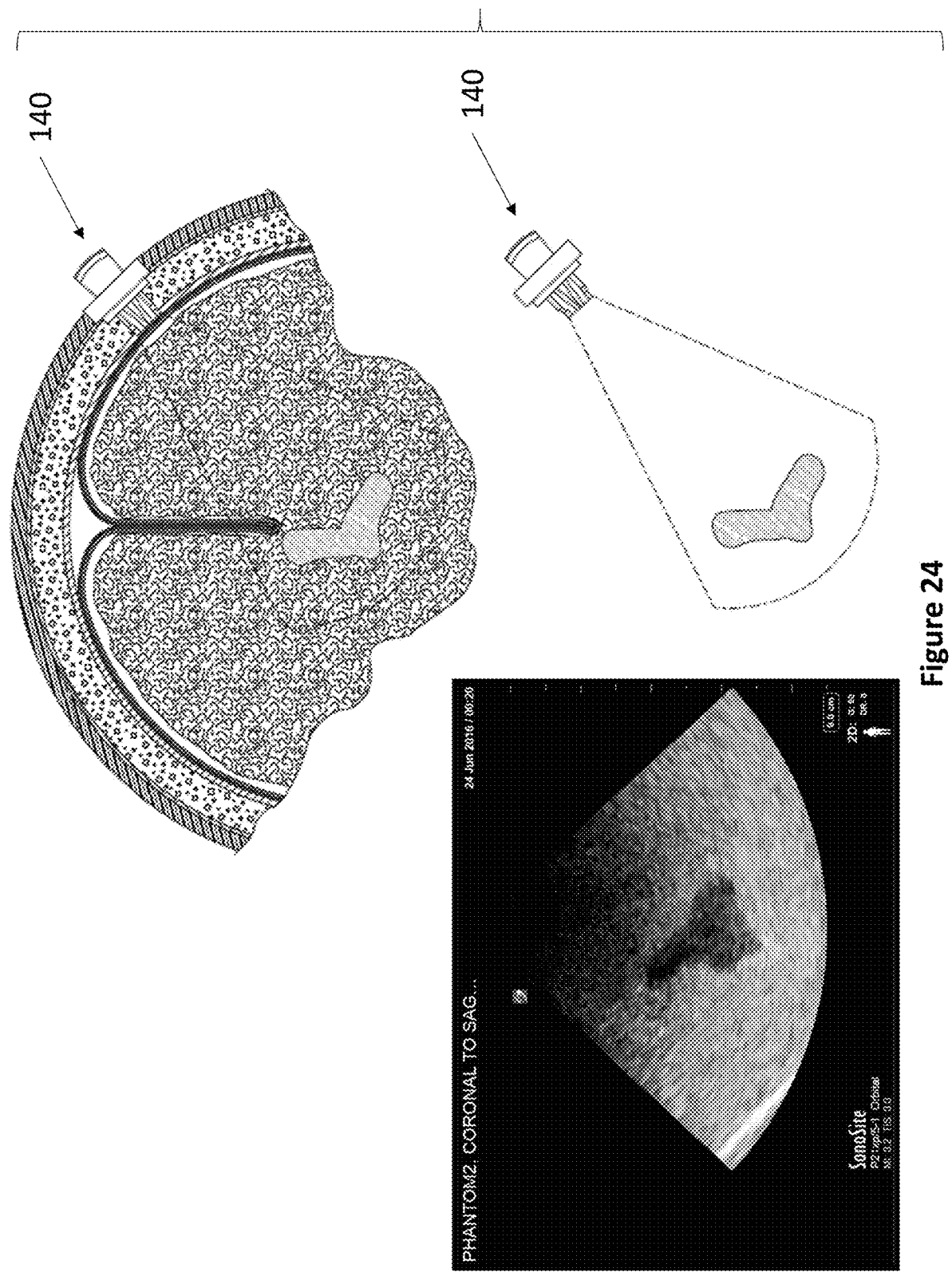

FIG. 24 depicts a device of the present invention actuated slightly from FIG. 23 to capture a second cross-sectional ultrasound image of the ventricles of the brain.

Figure 25:
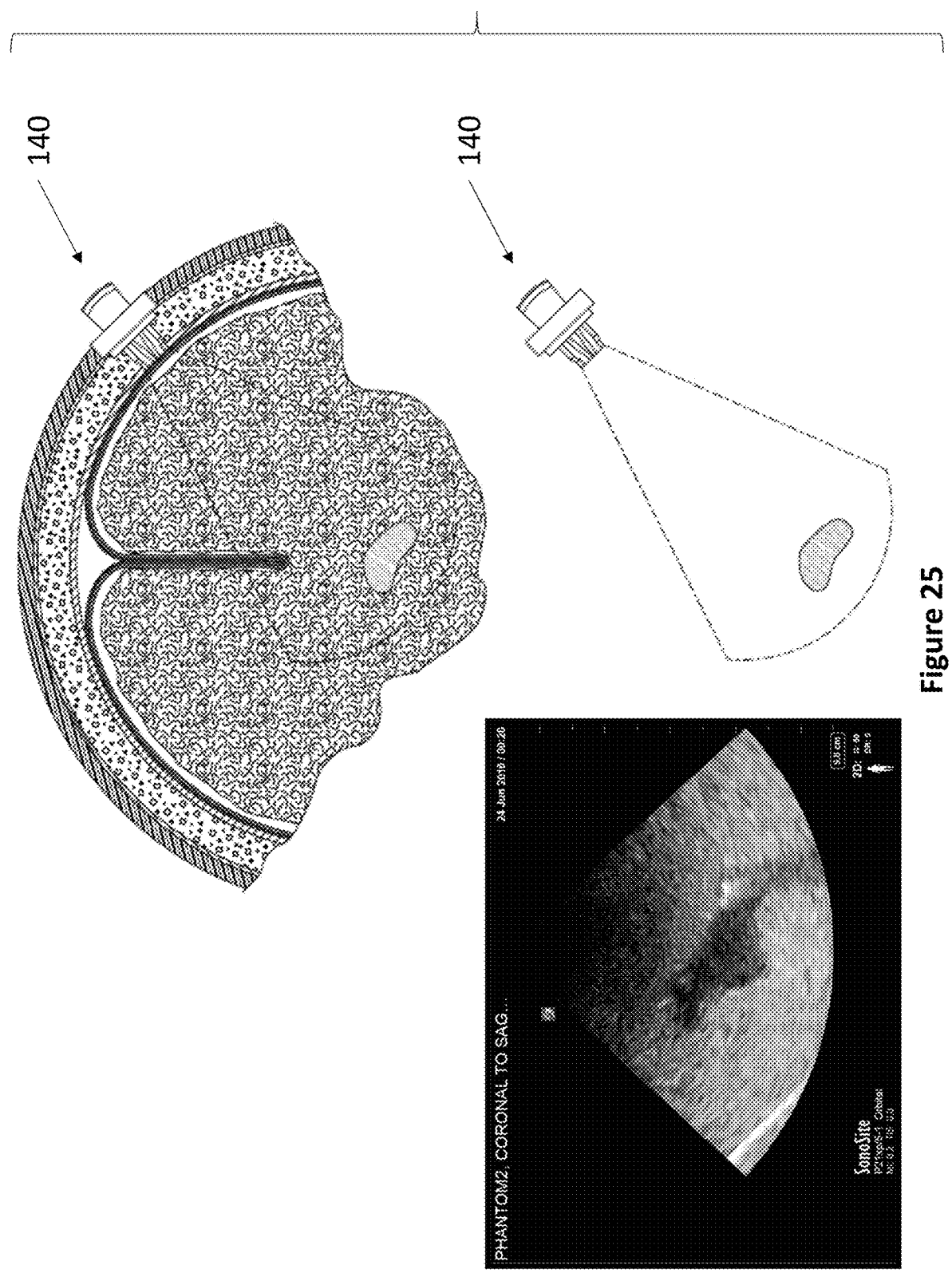

FIG. 25 depicts a device of the present invention actuated slightly from FIG. 23 to capture a third cross-sectional ultrasound image of the ventricles of the brain.

Figure 26:
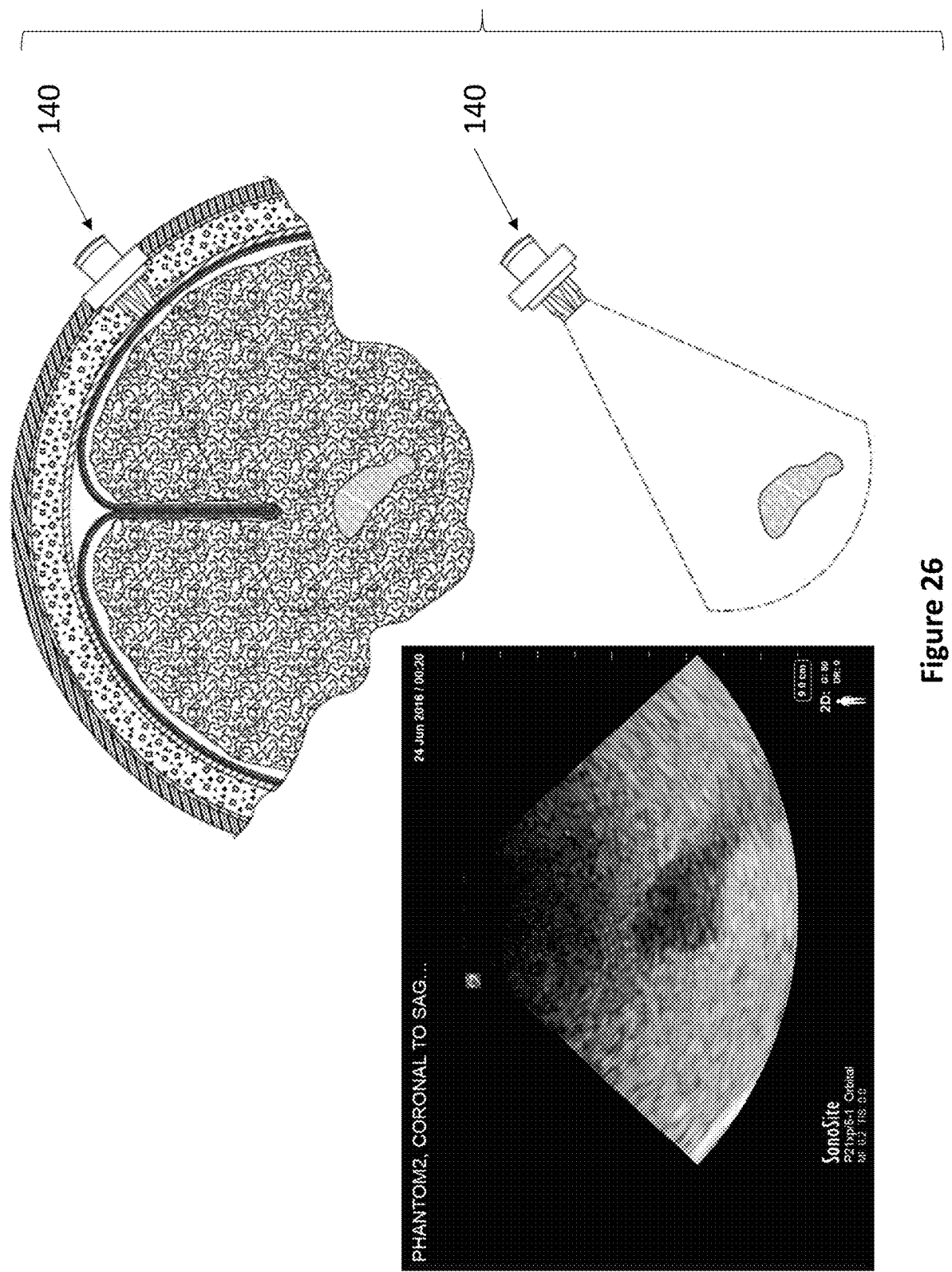

FIG. 26 depicts a device of the present invention actuated slightly from FIG. 23 to capture a fourth and a fifth cross-sectional ultrasound image of the ventricles of the brain.

Figure 27:
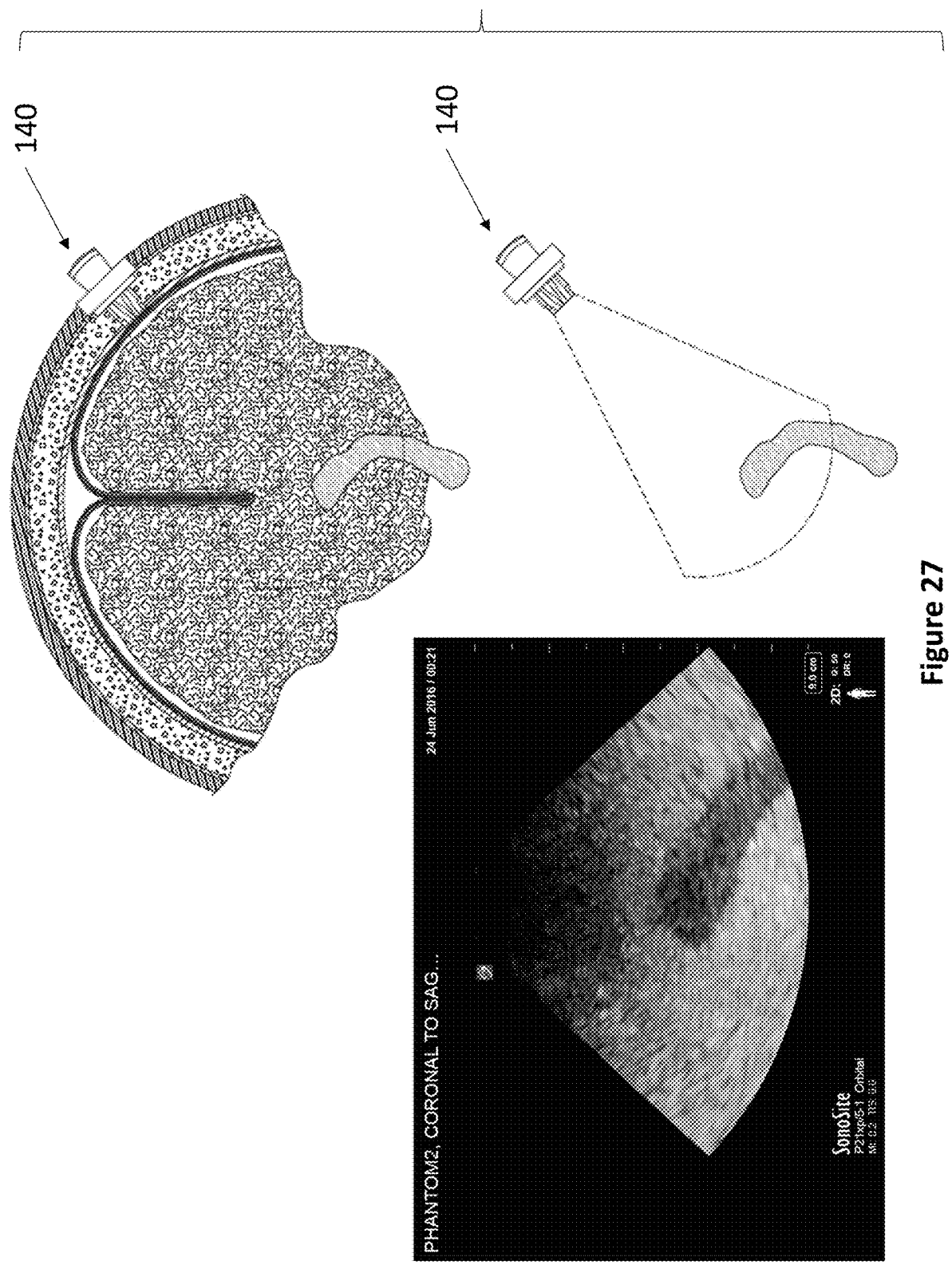

FIG. 27 depicts a device of the present invention actuated slightly from FIG. 23 to capture a sixth cross-sectional ultrasound image of the ventricles of the brain.

Figure 28:
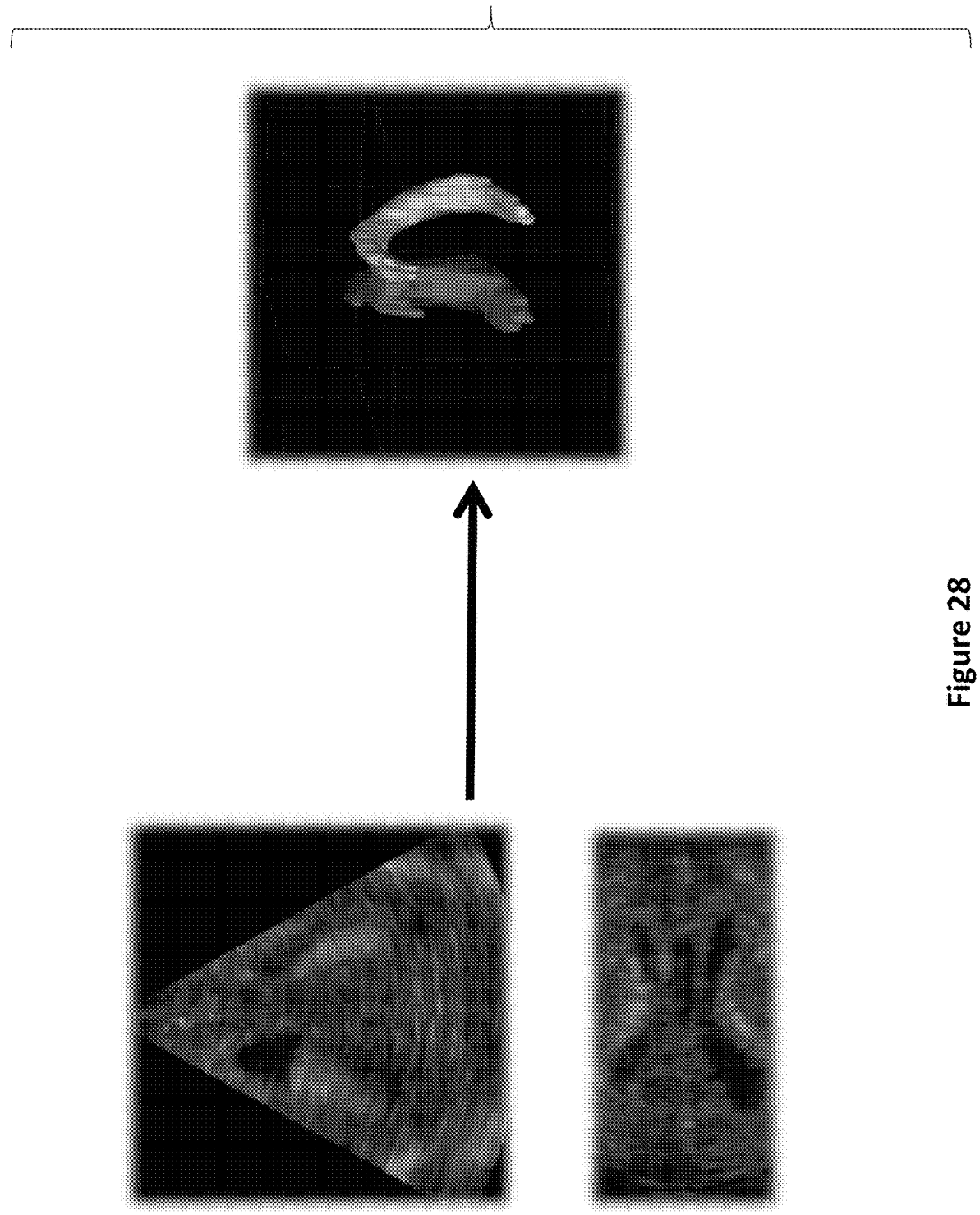

FIG. 28 depicts an exemplary 3D reconstruction of the ventricles of the brain using the ultrasound images captured in FIG. 23 through FIG. 27.

Figure 29:
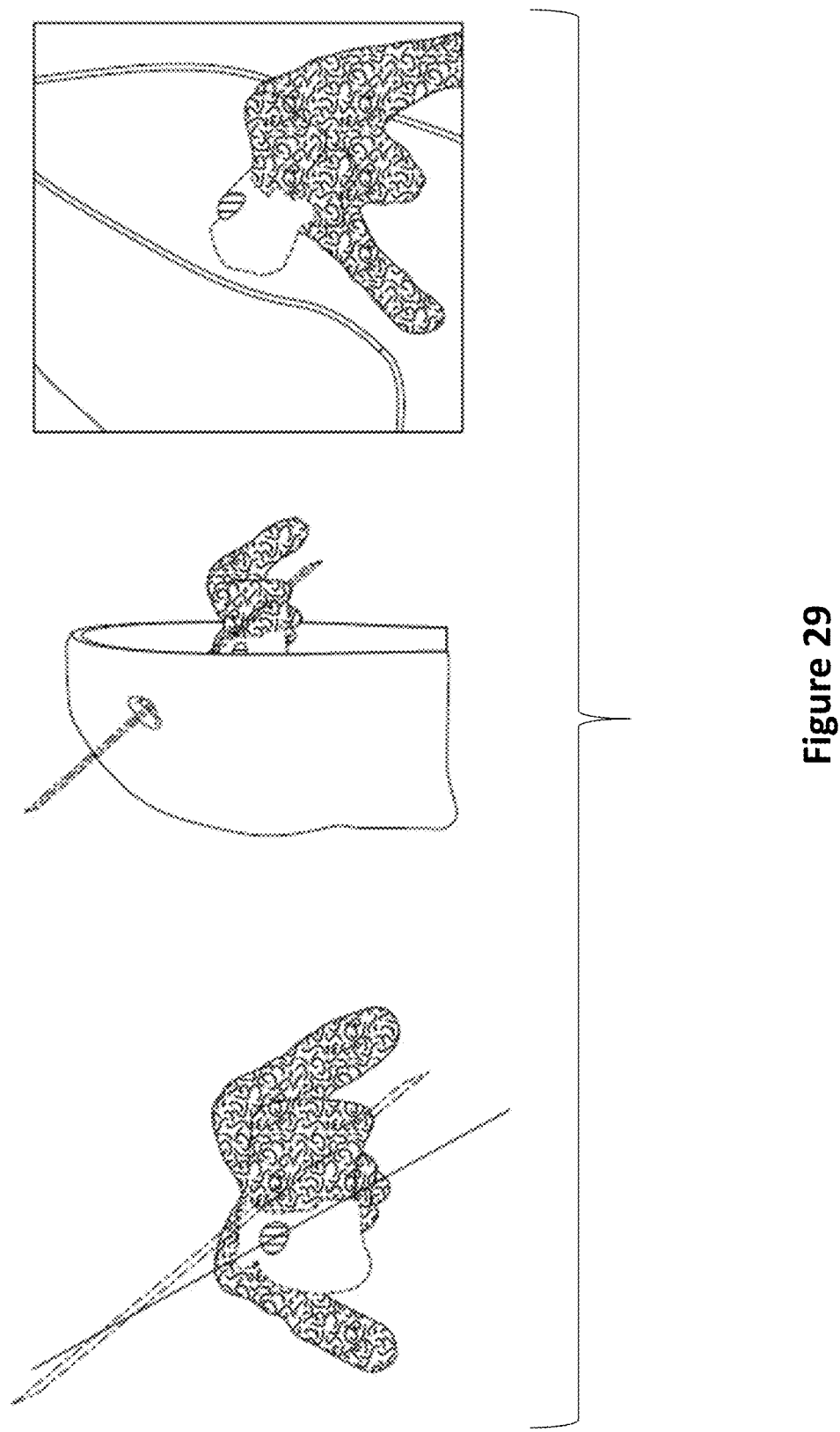

FIG. 29 depicts an exemplary method of determining an ideal angle of entry from the skull perforation performed in FIG. 20 into the ventricles of the brain.

Figure 30:
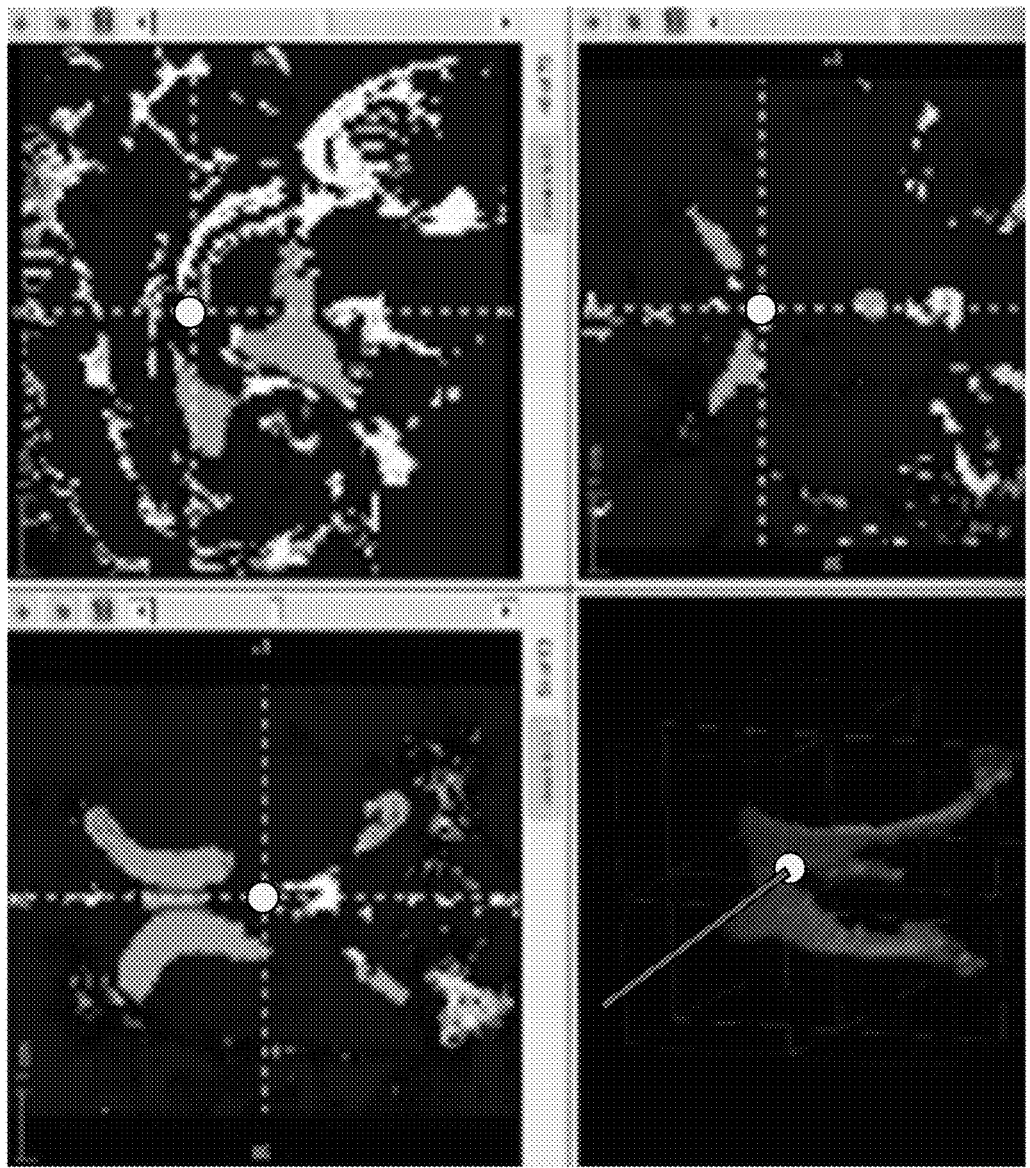

FIG. 30 depicts an exemplary method of targeting a location in the ventricles of the brain using the exemplary 3D reconstruction of the ventricles of the brain in FIG. 28, wherein the targeted location is indicated by the outlined circle, the crosshairs are aimed at the targeted location, and the ultrasound images are supplemented with angle, rotation, and tilt data.

Figure 31:
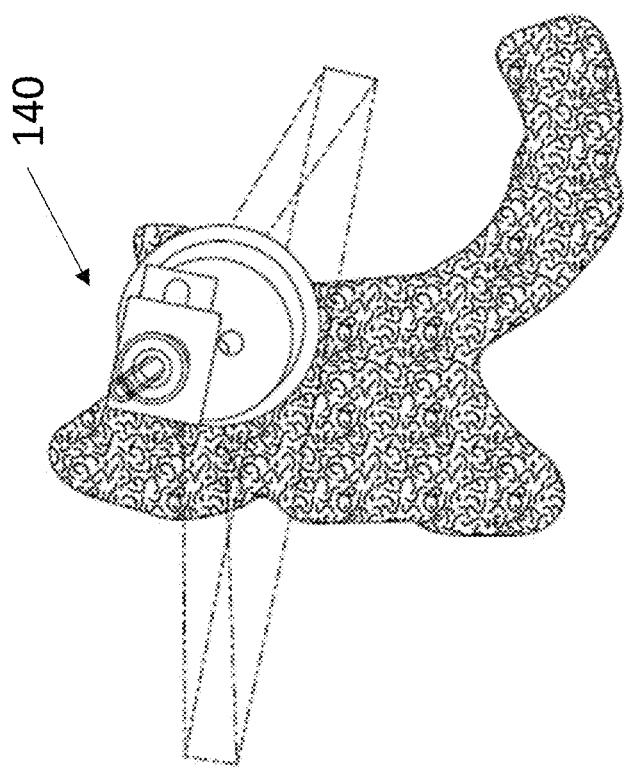

FIG. 31 depicts the alignment of a device of the present invention to match the ideal angle of entry determined in FIG. 29.

Figure 32:
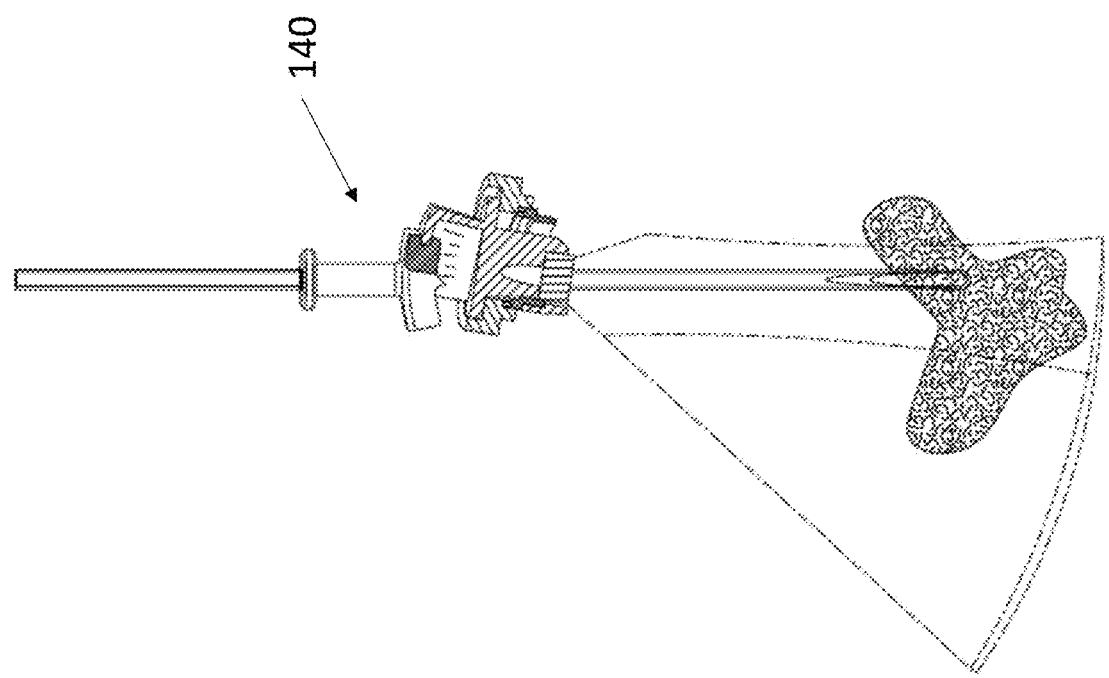

FIG. 32 depicts an exemplary method of accurate insertion of a medical device through a device of the present invention, wherein the location of the medical device is monitored using out-of-plane ultrasound imaging.

FIG. 33 depicts the result of accurately inserting an external ventricular drain using a device of the present invention.

Figure 34:
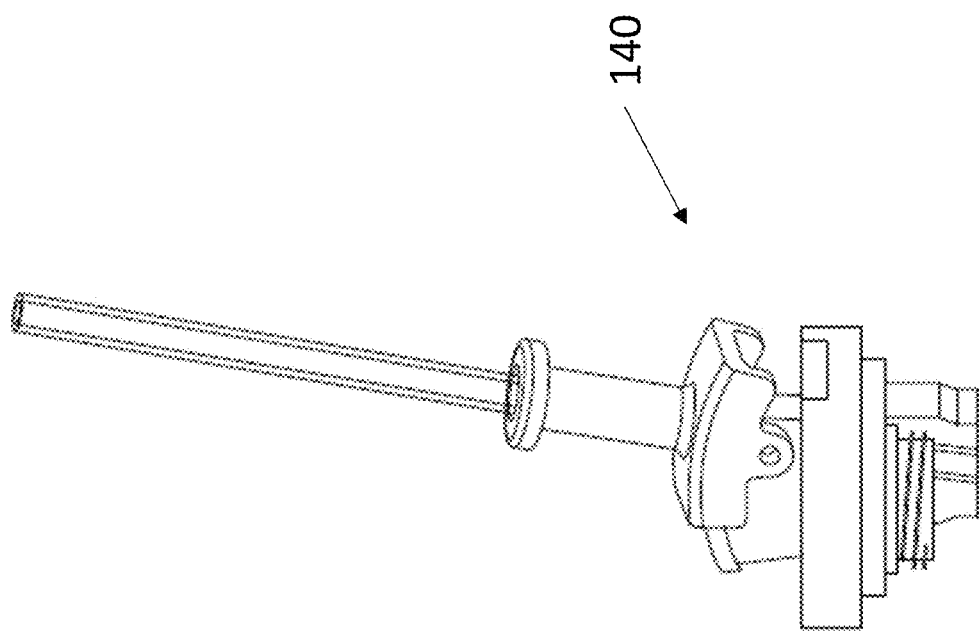

FIG. 34 depicts the removal of a device of the present invention over an inserted medical device, leaving the medical device behind.

Figure 35:
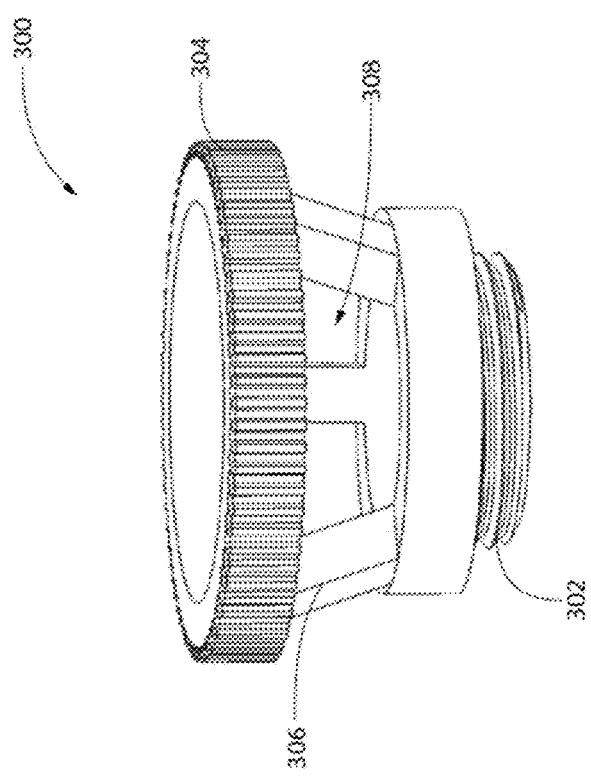

FIG. 35 depicts a bolt anchor with raised pillars according to one embodiment for use with methods described herein.

Figure 36C:
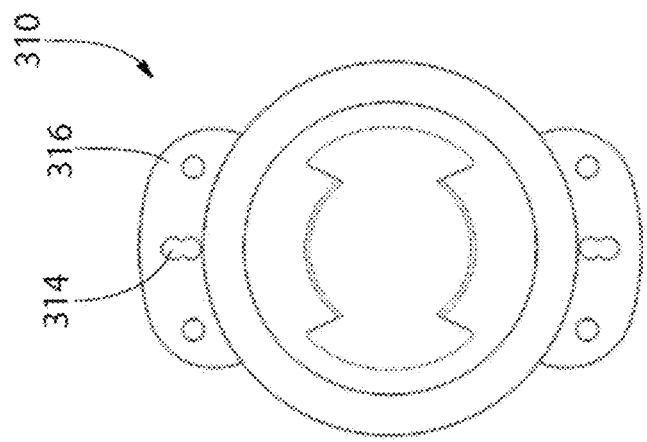
Figure 36B:
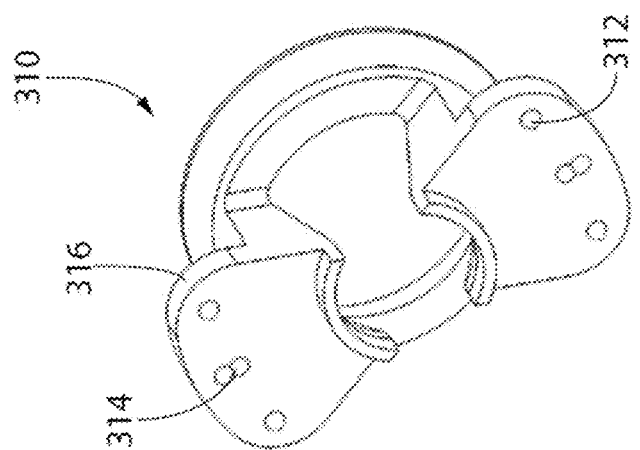
Figure 36A:
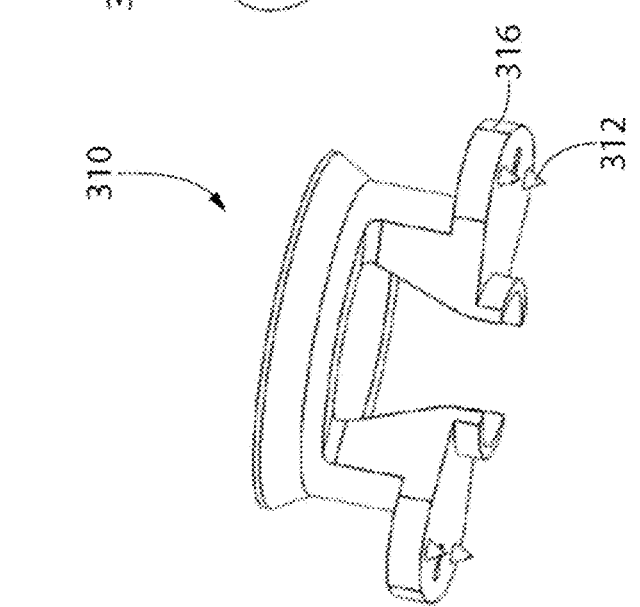

FIG. 36A depicts a side-perspective view of a bolt anchor with raised pillars according to another embodiment for use with the methods described herein.

FIG. 36B depicts a bottom-perspective view of the bolt anchor and FIG. 36C depicts a top view of the bolt anchor.

Figure 37B:
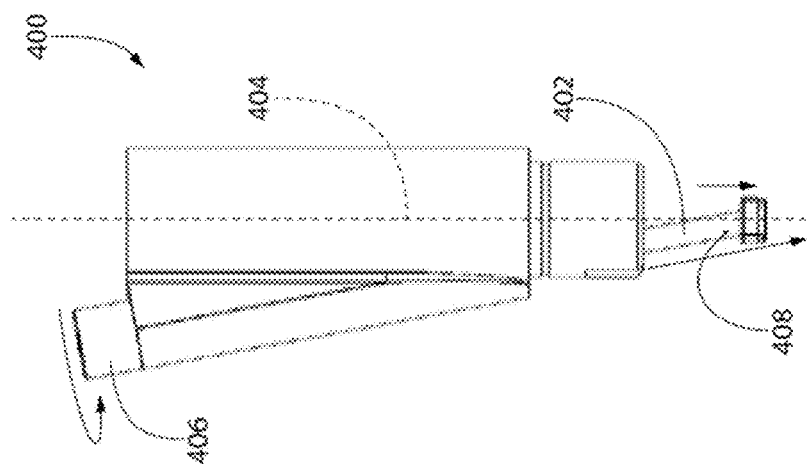
Figure 37A:
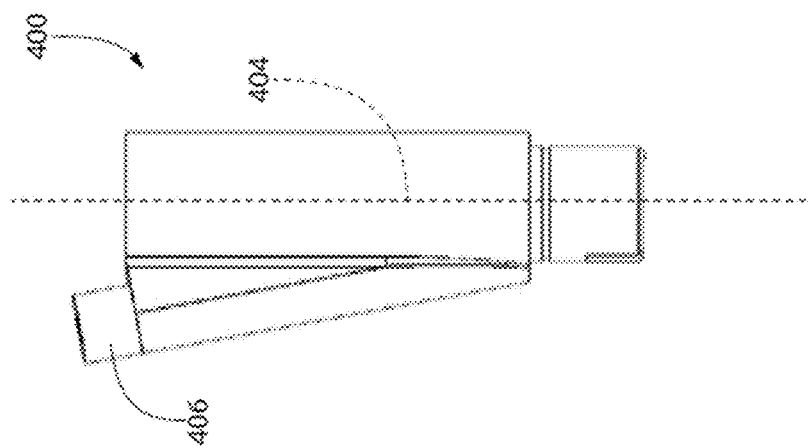
Figure 37D:
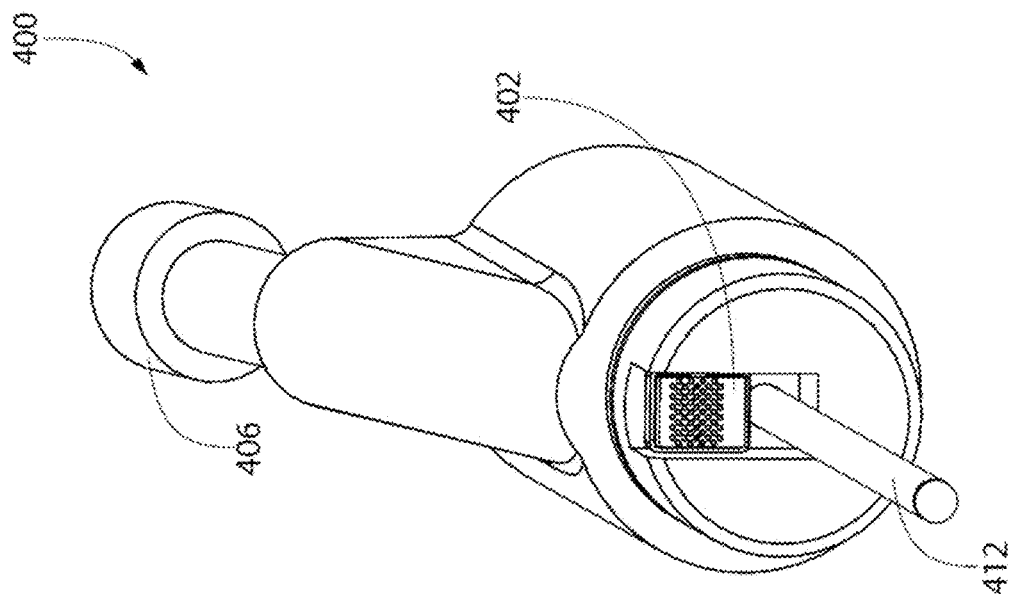
Figure 37C:
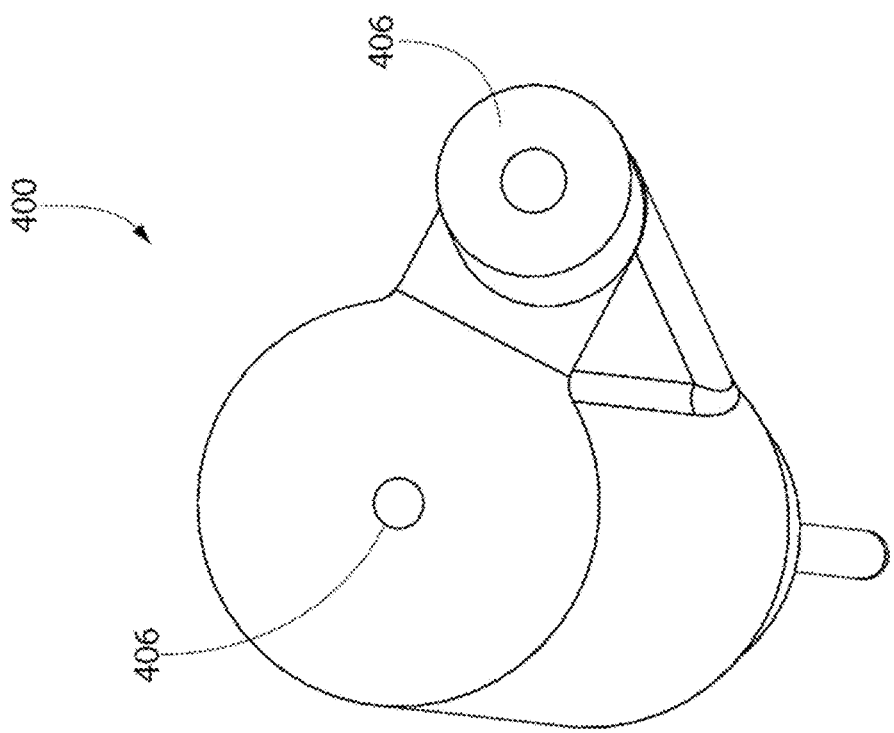

FIG. 37A depicts a side view of an ultrasound probe assembly with the ultrasound probe retracted, and FIG. 37B depicts a side view of an ultrasound probe assembly with the ultrasound probe deployed. FIG. 37C depicts a bottom perspective view of the ultrasound probe assembly and FIG. 37D depicts a top perspective view of the ultrasound probe assembly.

Figure 38A:
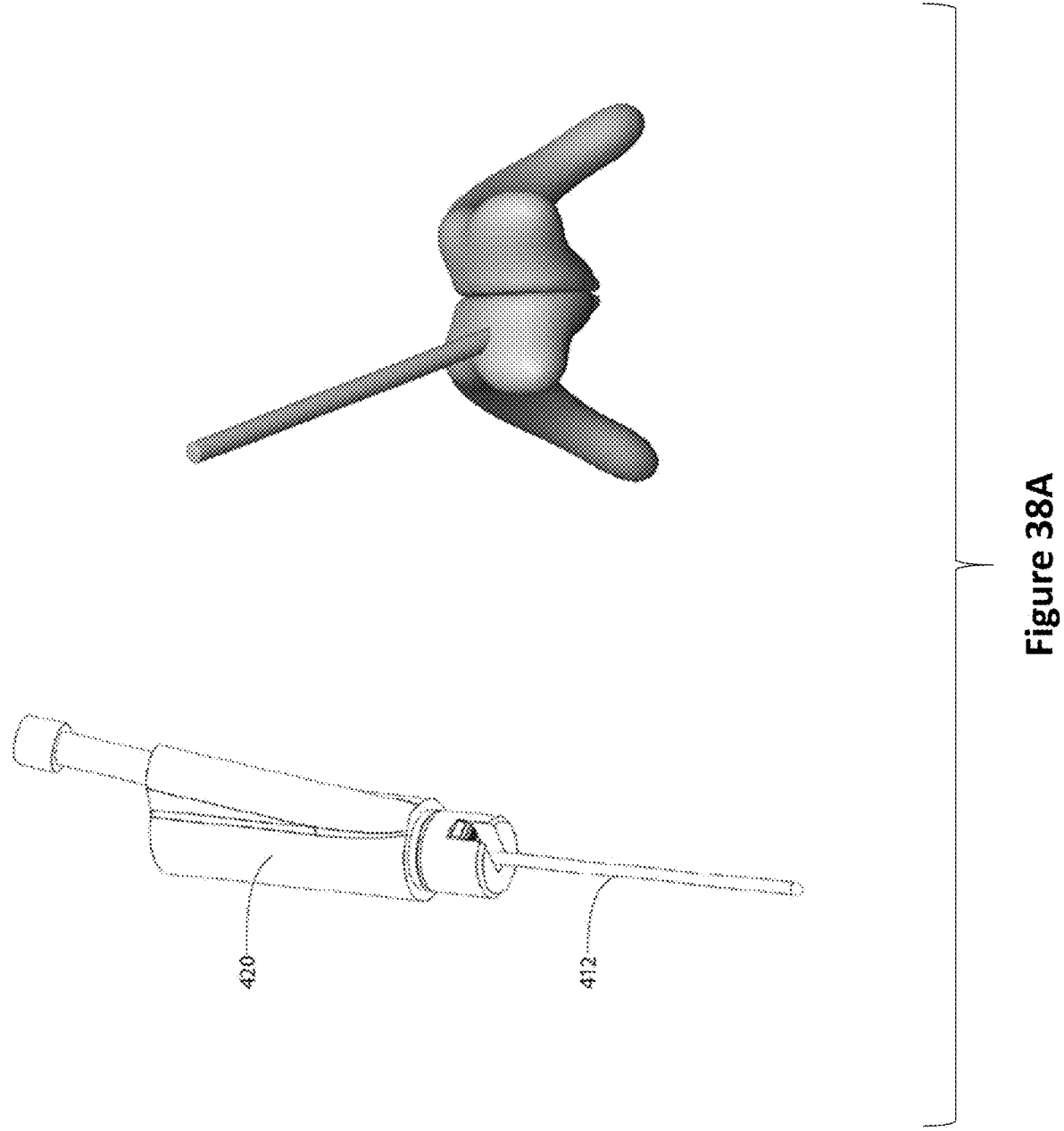

FIG. 38A depicts an ultrasound probe assembly having a linear encoder that will read an encoded EVD (or an EVD stylet) as it is inserted and advanced through the EVD guide tube, along with a representation of the 3D rendered ventricles. FIG. 38B depicts an alternate view of the ultrasound probe assembly and encoded EVD as it is inserted and advanced through the EVD guide tube, along with a representation of the 3D rendered ventricles.

Figure 39A:
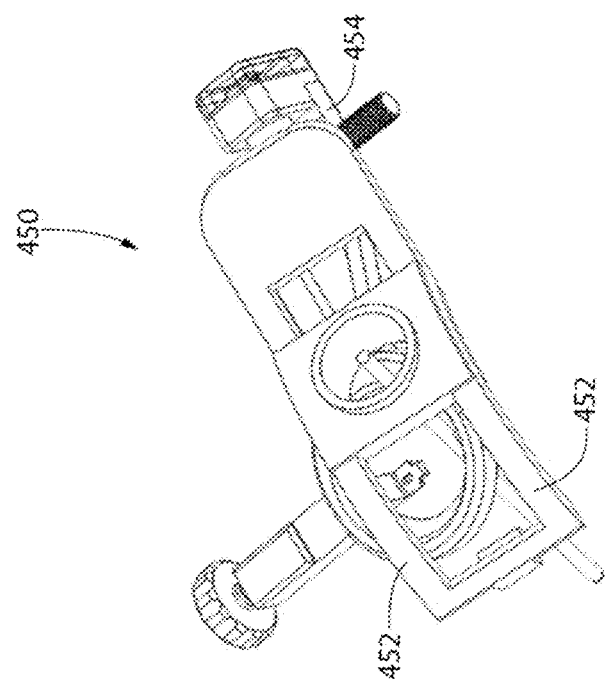
Figure 39B:
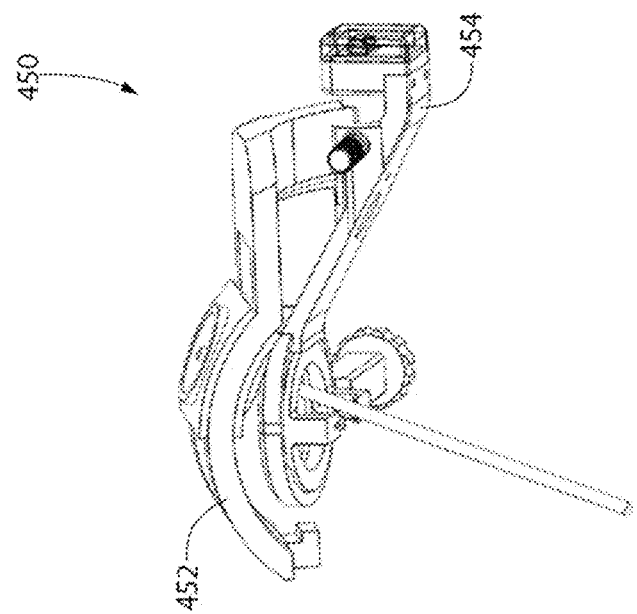
Figure 39C:
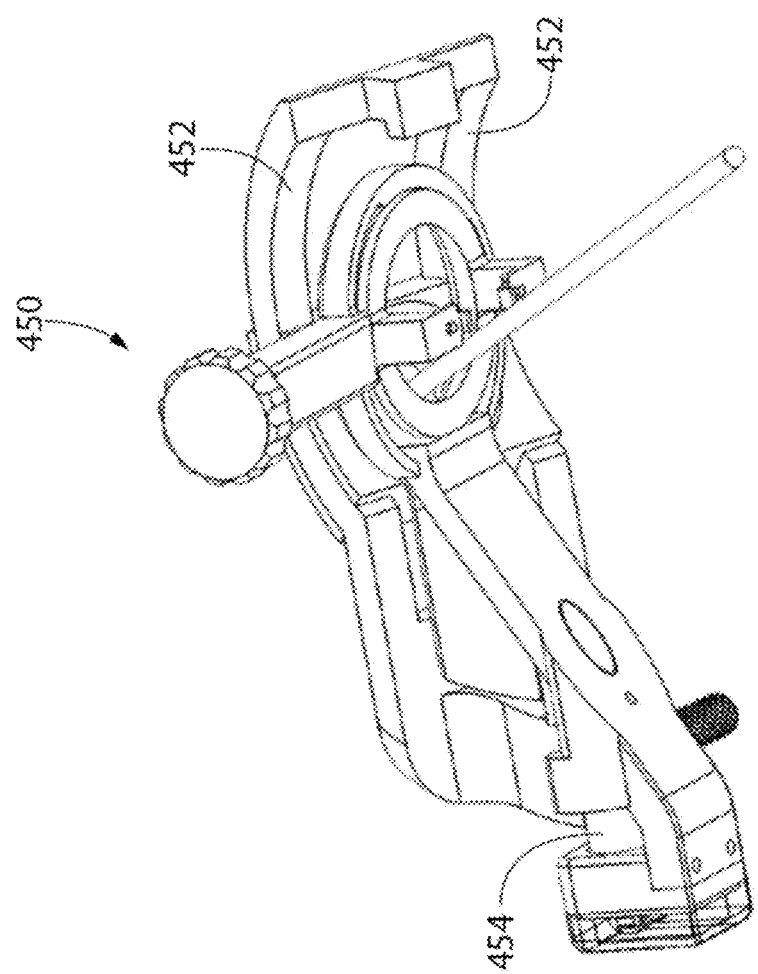

FIG. 39A is a side perspective view of a patient interface device (PID) guide with linear and rotary encoders according to one embodiment. FIG. 39B is a top perspective view of the PID guide and FIG. 39C is an alternate side perspective view of the PID guide.

Figure 40:
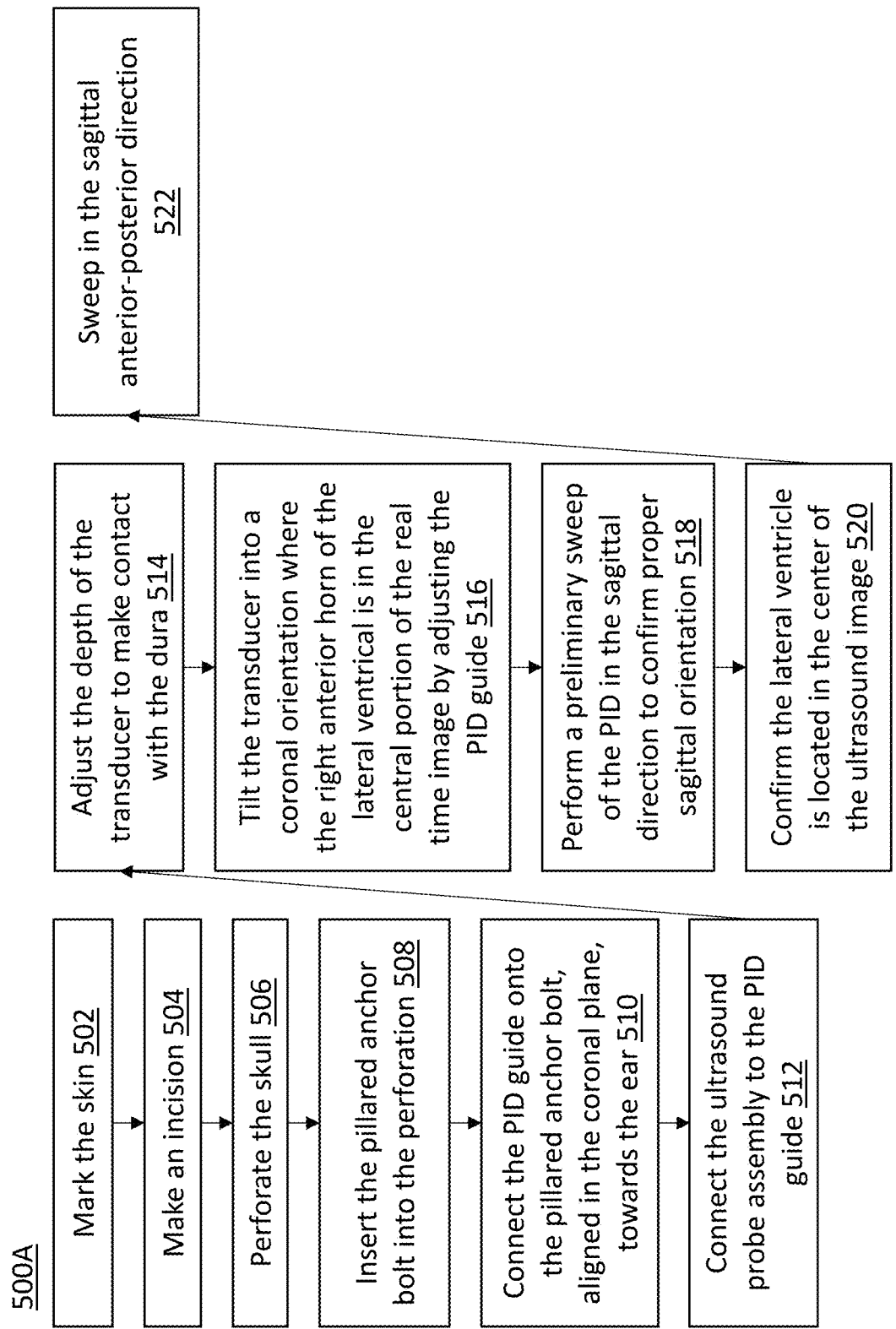

FIG. 40 is a flowchart of an exemplary method of positioning a PID system for insertion of an EVD according to one embodiment.

Figure 41:
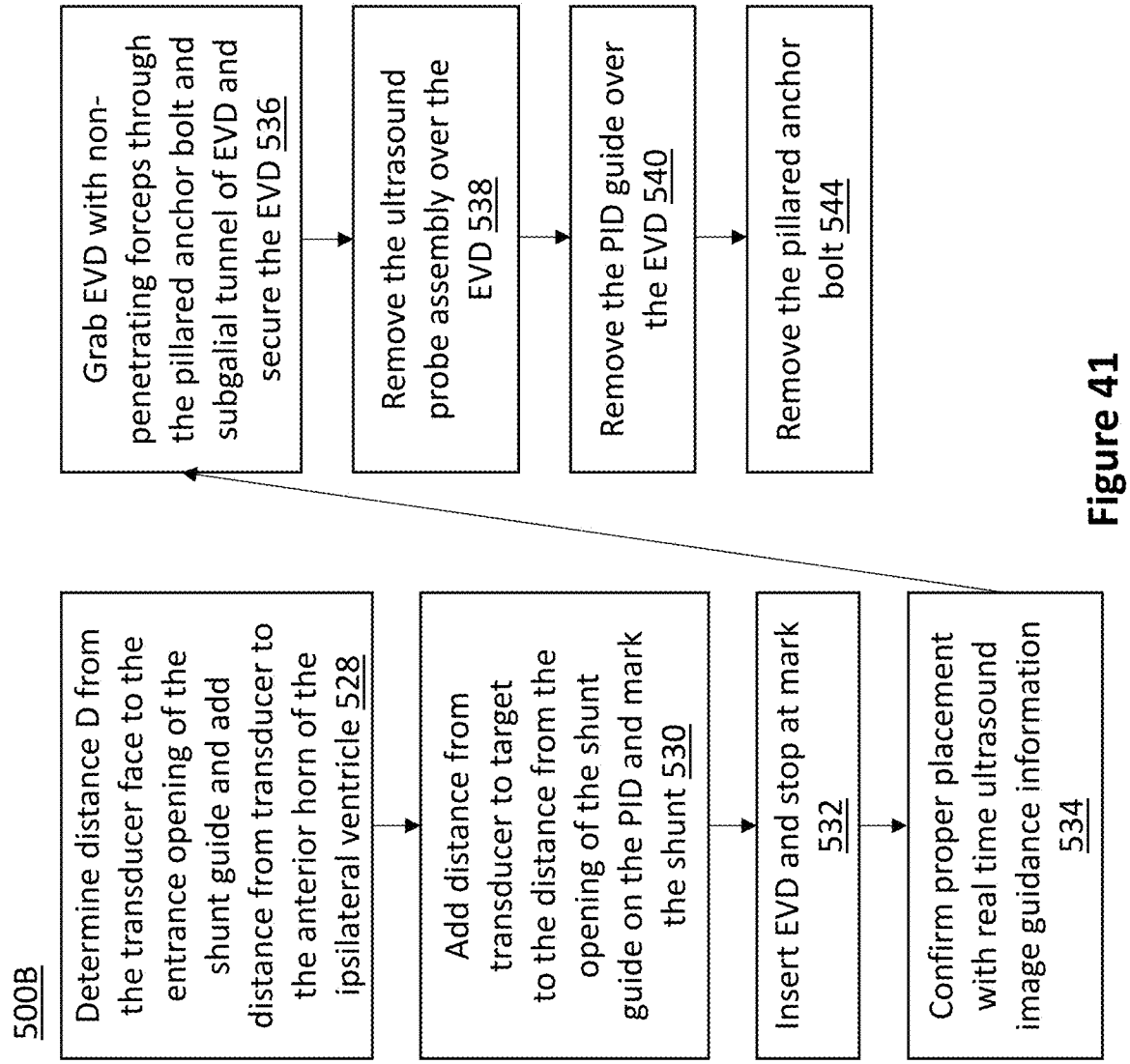

FIG. 41 is a flowchart of an exemplary method of placing an EVD according to one embodiment.

FIG. 42A is a diagram of a pillared anchor bolt threaded into the scull according to one embodiment, and FIG. 42B is an image of a pillared anchor bold threaded into the scull according to one embodiment.

Figure 43:
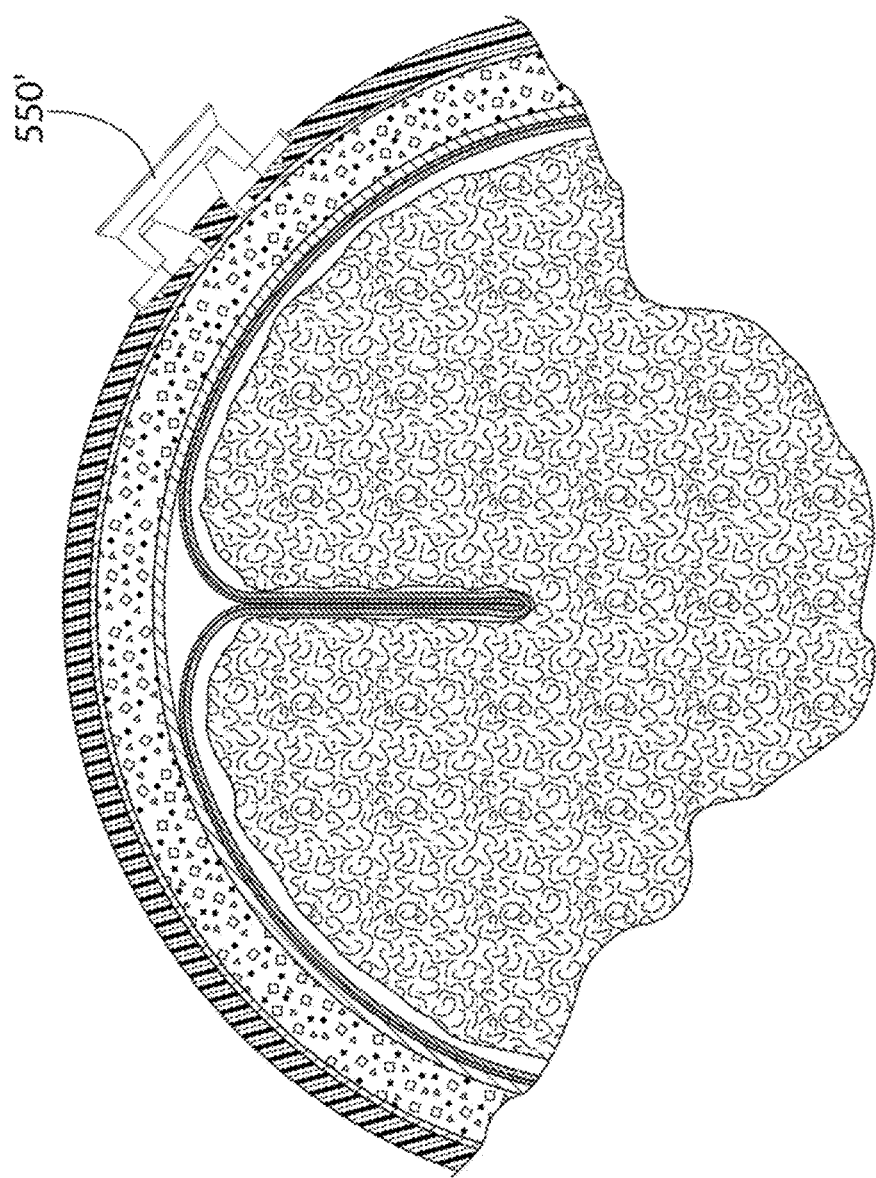

FIG. 43 is a diagram of an alternative pillared anchor bolt threaded into the scull according to one embodiment.

Figure 44:
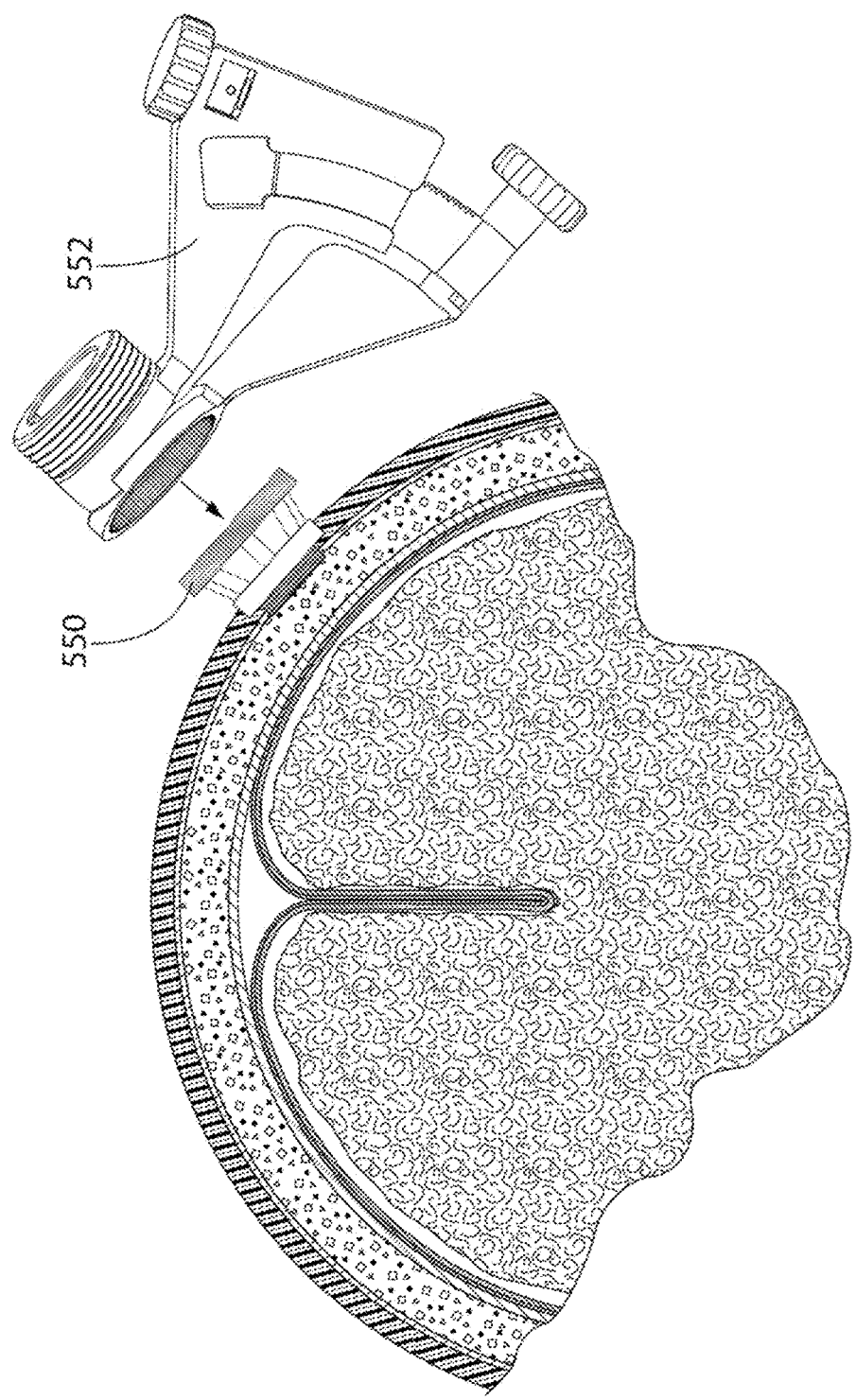

FIG. 44 is a diagram of a PID guide aligned over the pillared anchor bolt according to one embodiment.

Figure 45:
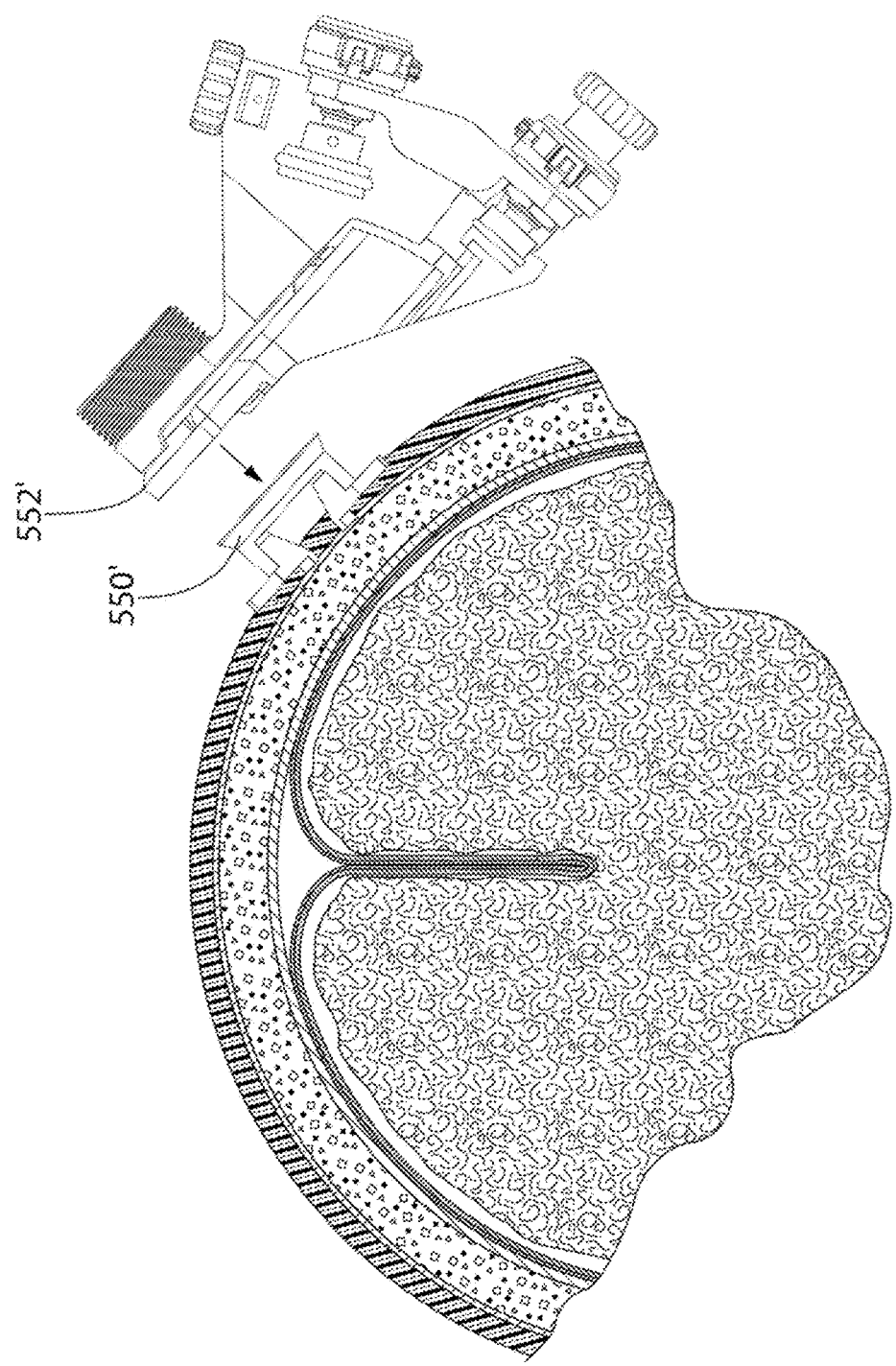

FIG. 45 is a diagram of an encoder based PID guide aligned over an alternative pillared anchor bolt according to one embodiment.

Figure 46:
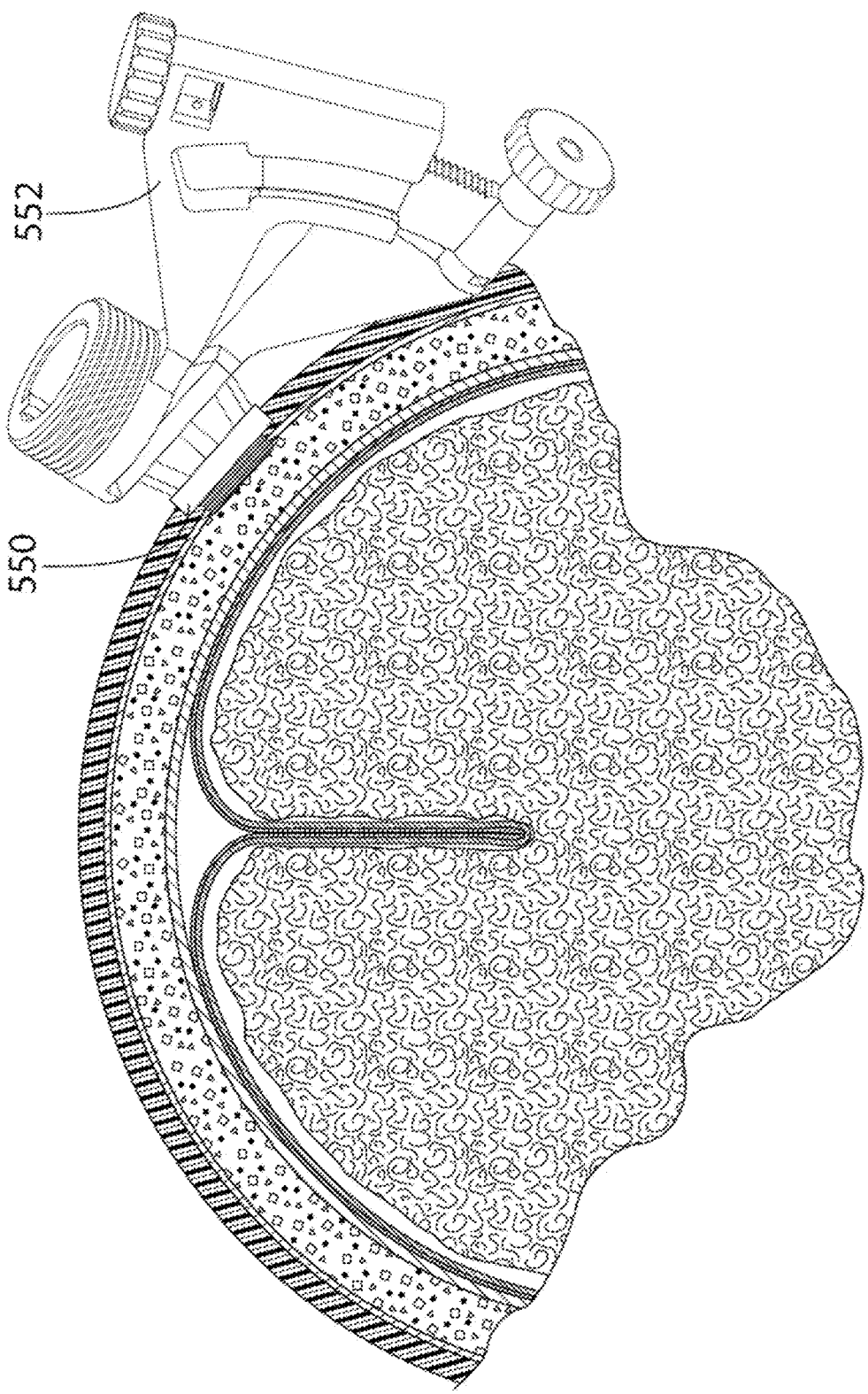

FIG. 46 is a diagram of PID guide connected to an anchor bolt according to one embodiment.

Figure 47:
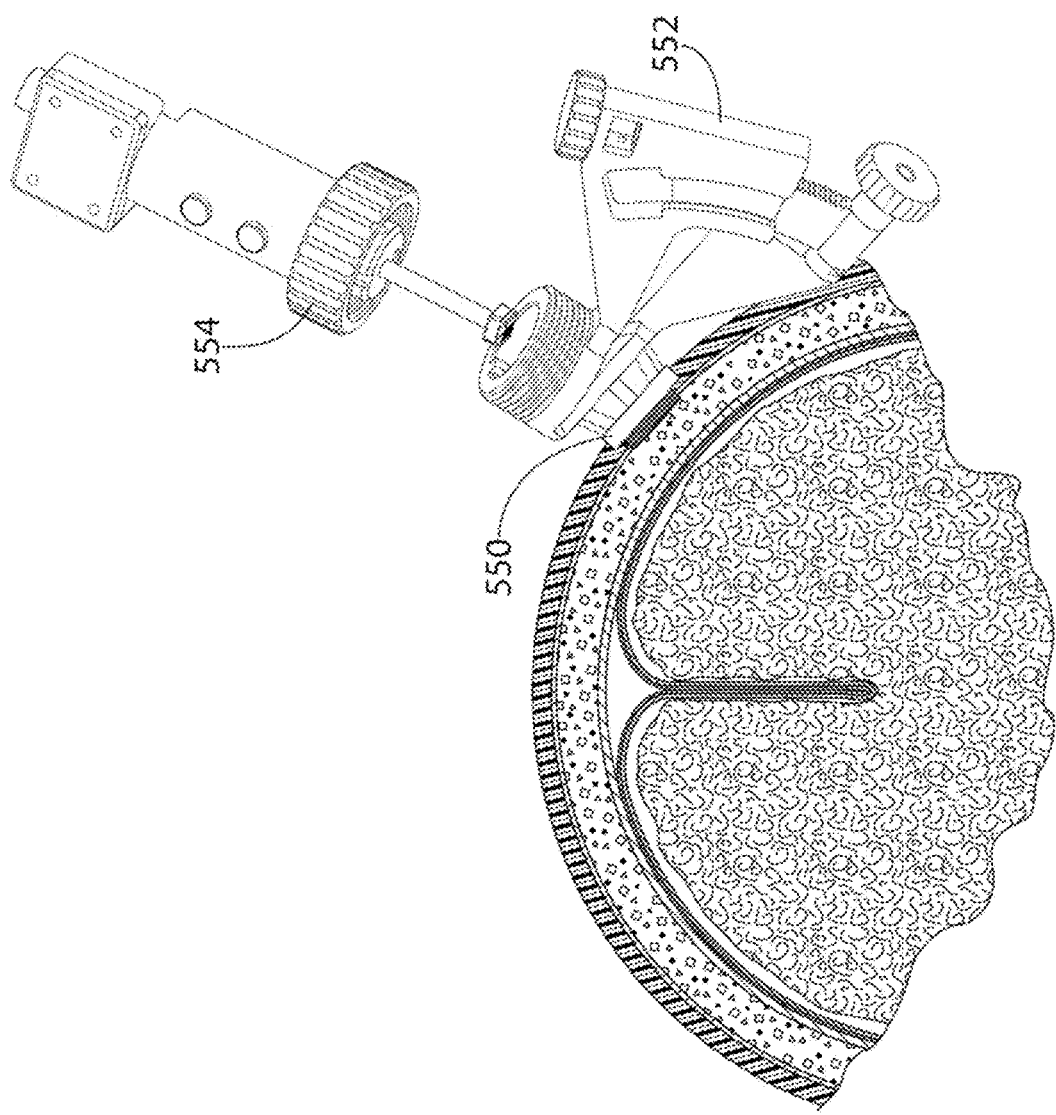

FIG. 47 is a diagram of an ultrasound probe assembly aligned over a PID guide according to one embodiment.

Figure 48:
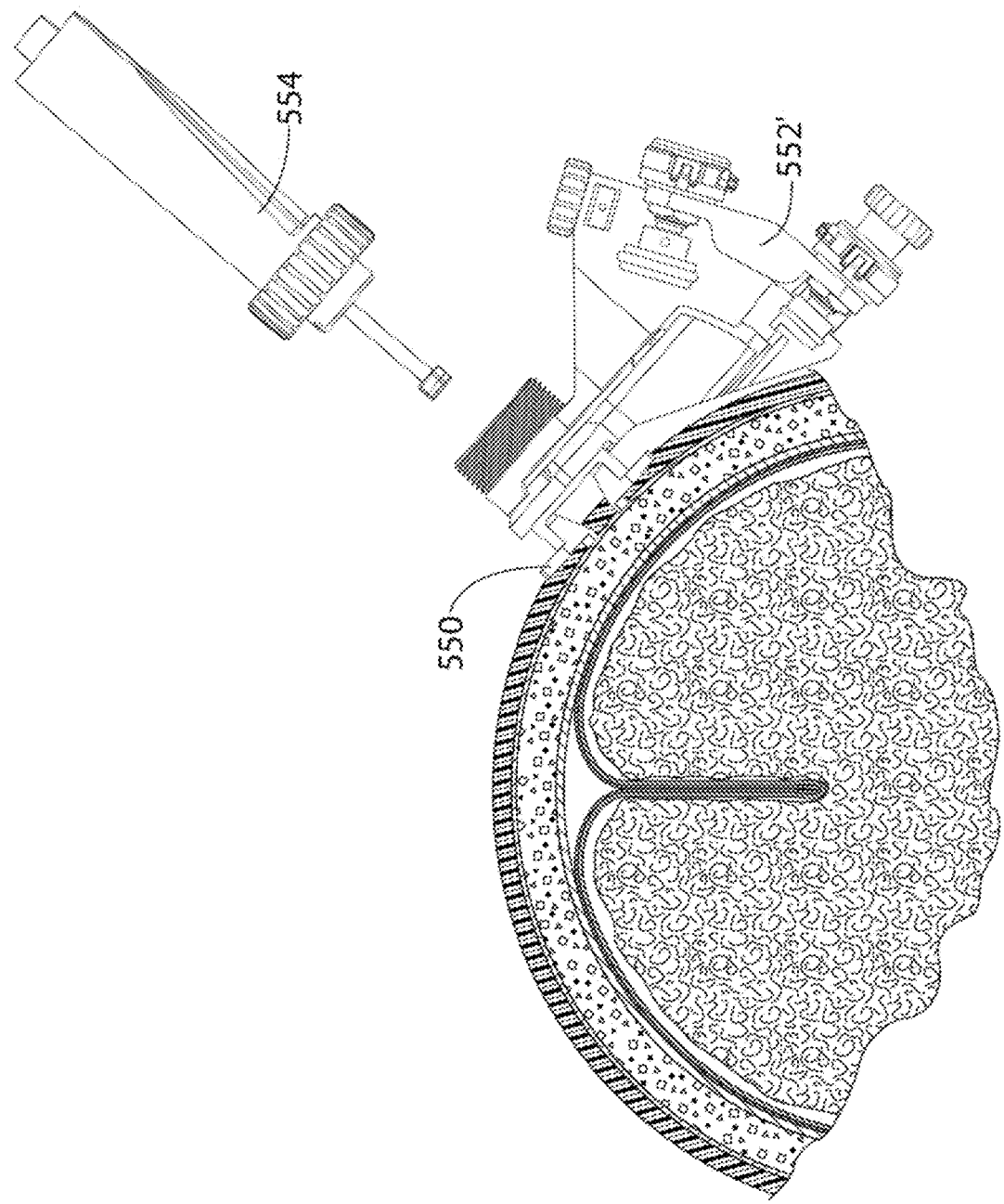

FIG. 48 is a diagram of an ultrasound probe assembly aligned over an encoder based PID guide according to one embodiment.

Figure 49:
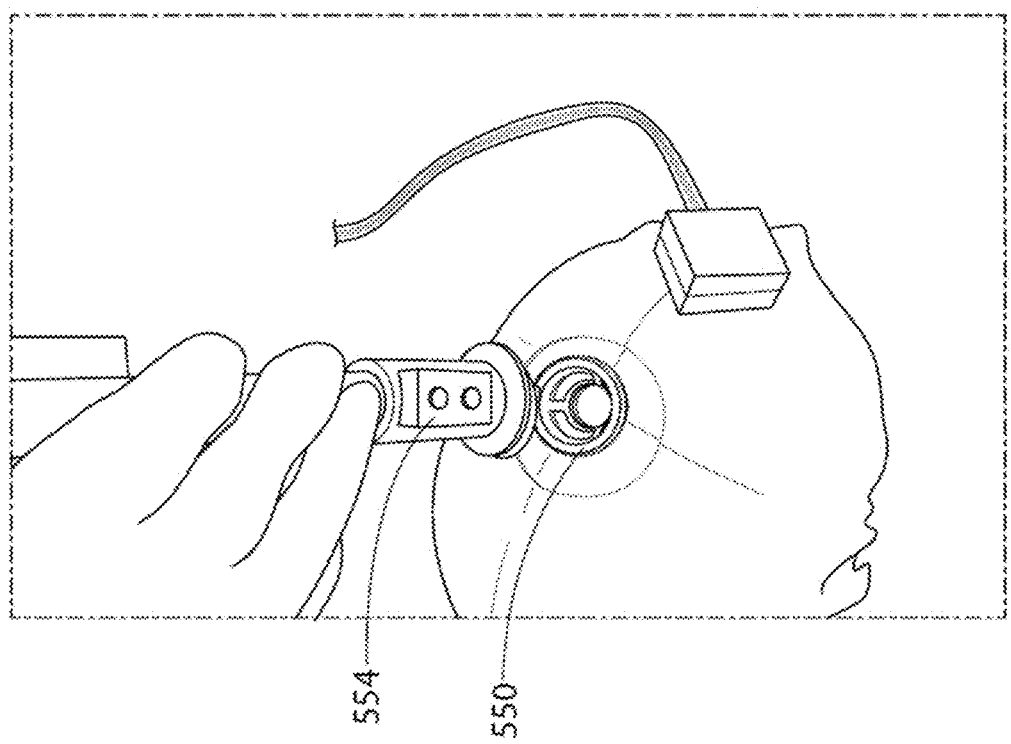

FIG. 49 is an image of an ultrasound probe assembly being inserted into a pillared anchor bolt according to one embodiment.

Figure 50:
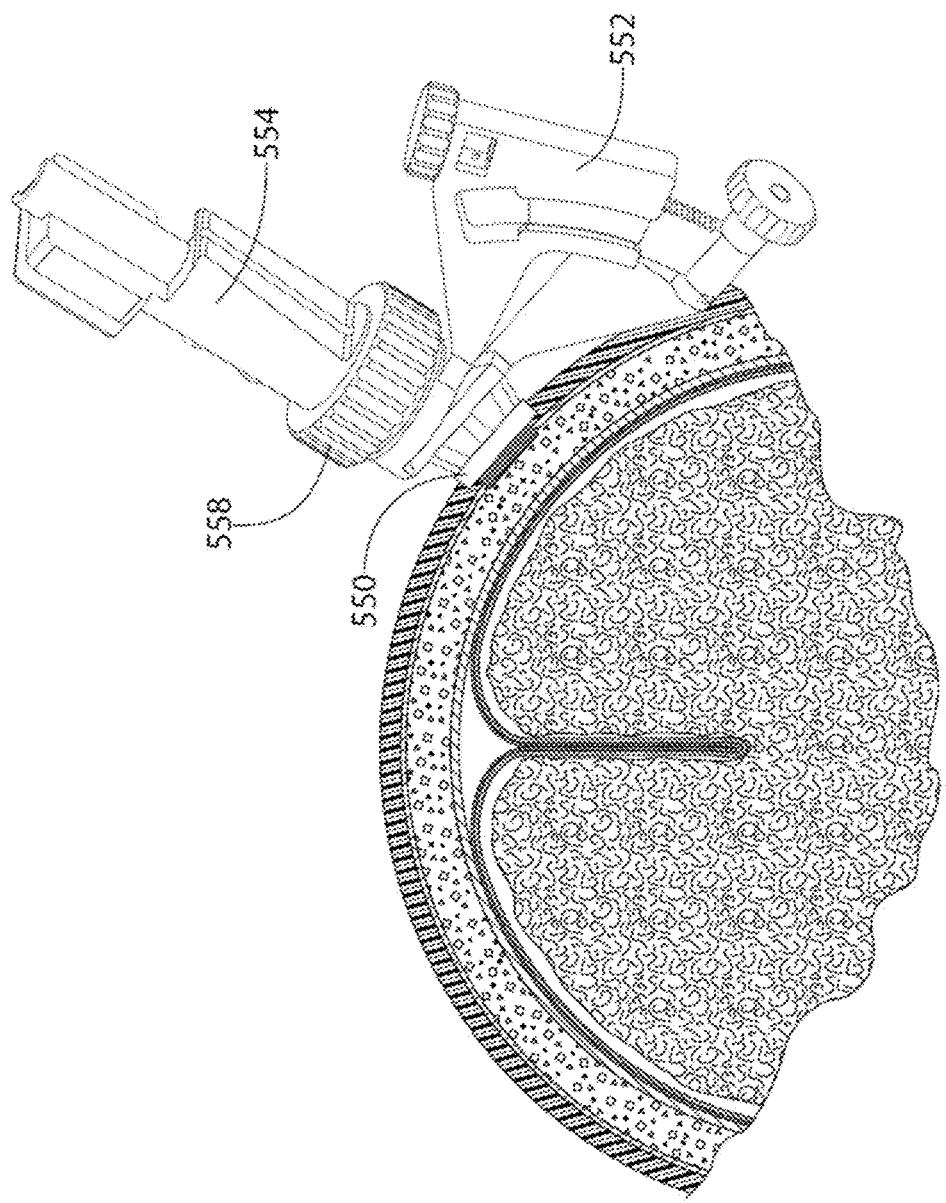

FIG. 50 is a diagram of a fully assembled PID system according to one embodiment.

Figure 51:
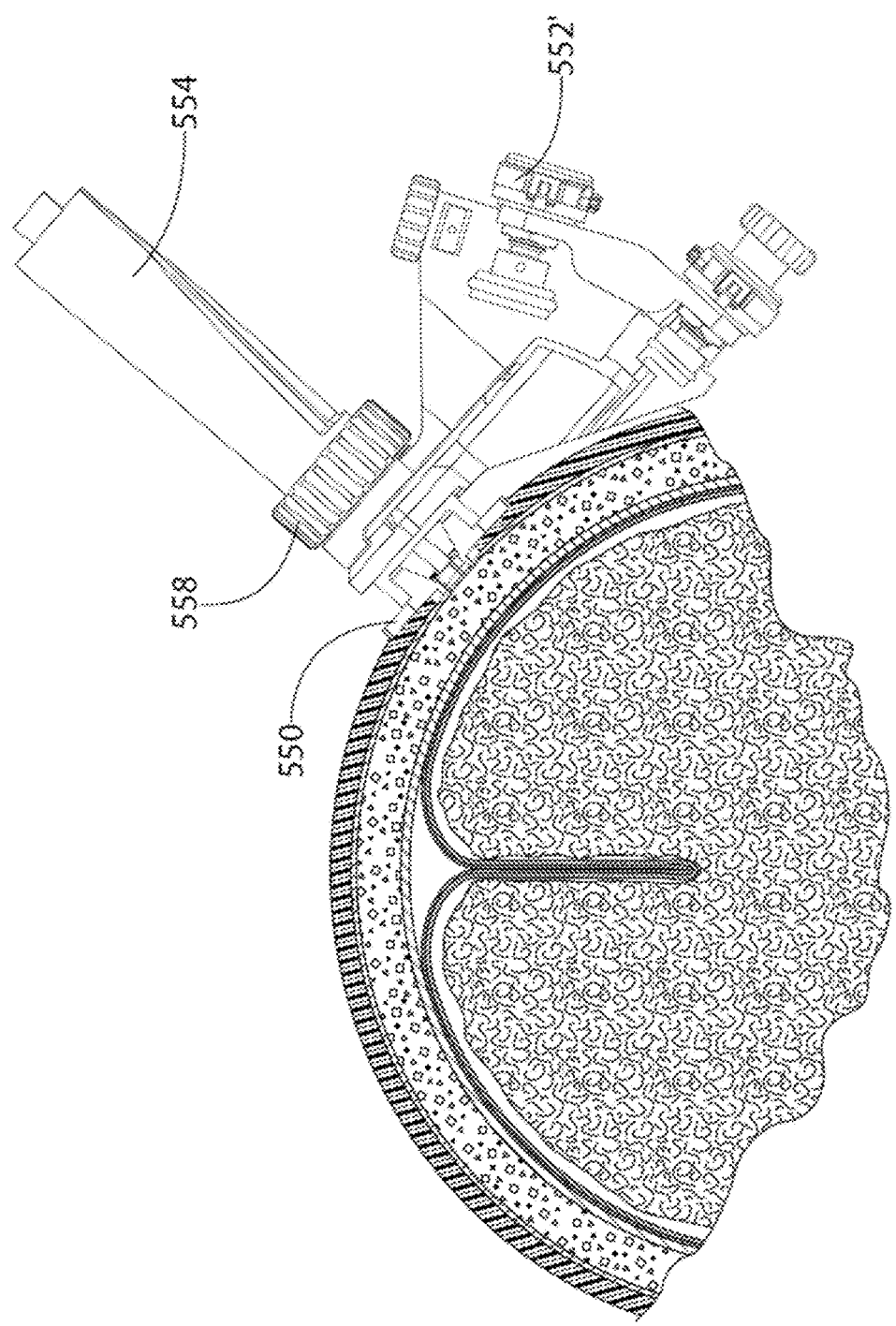

FIG. 51 is a diagram of a fully assembled PID system having an encoder based PID guide according to one embodiment.

Figure 52:
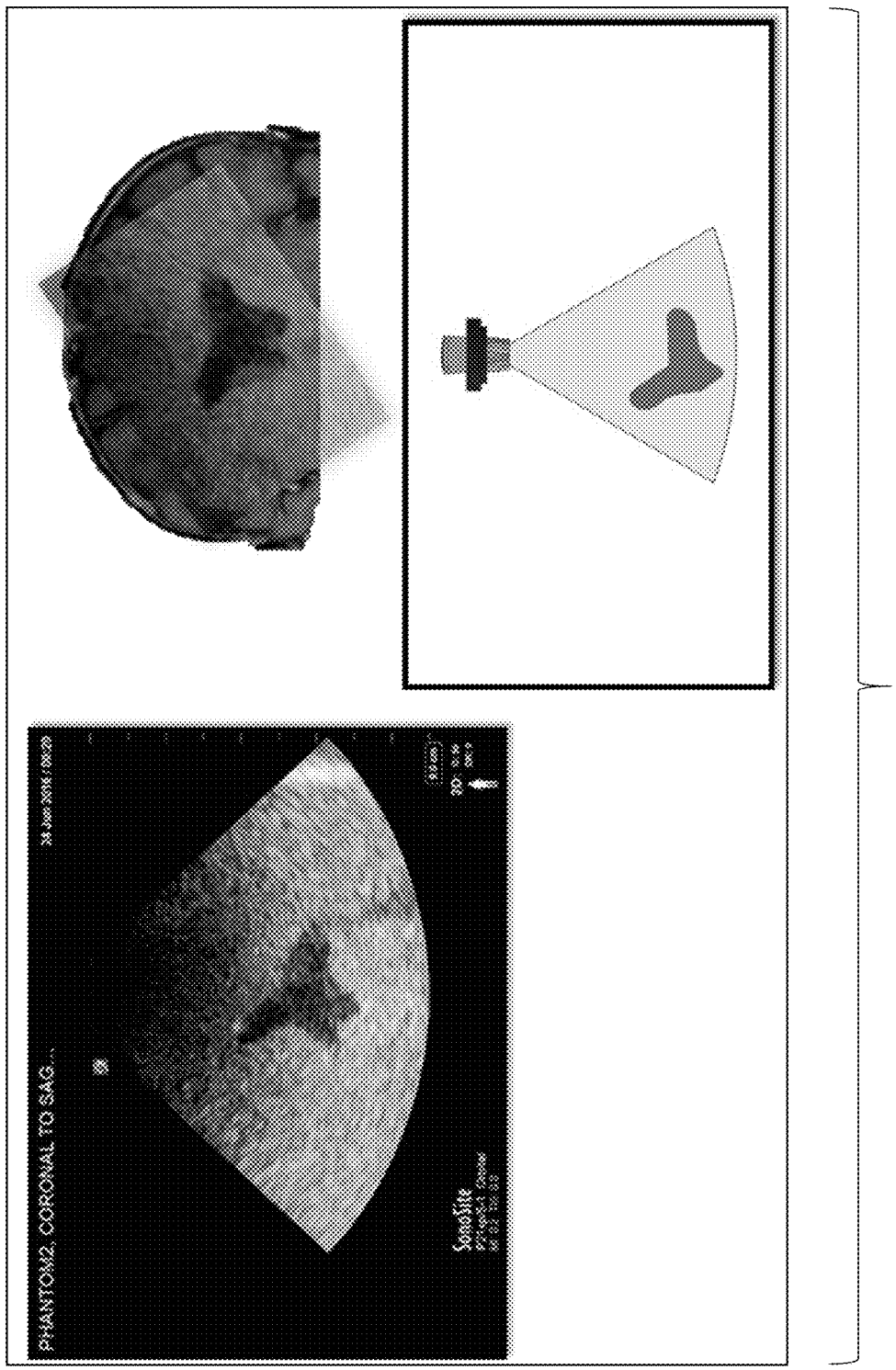

FIG. 52 is an exemplary user interface, illustrating the step of tilting the transducer into the ideal coronal orientation where the right anterior horn of the lateral ventricle is in the central portion of the real time image by adjusting the angle of the PID guide according to one embodiment.

Figure 53:
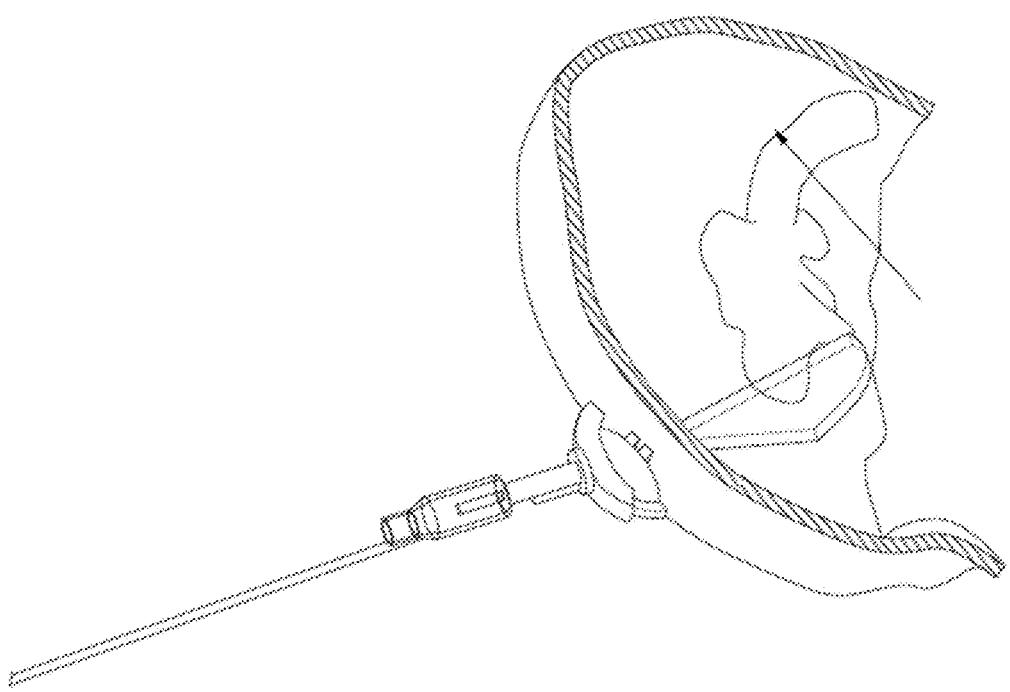

FIG. 53 is a diagram illustrating a sweep of the target location for auto-segmentation according to one embodiment.

Figure 54:
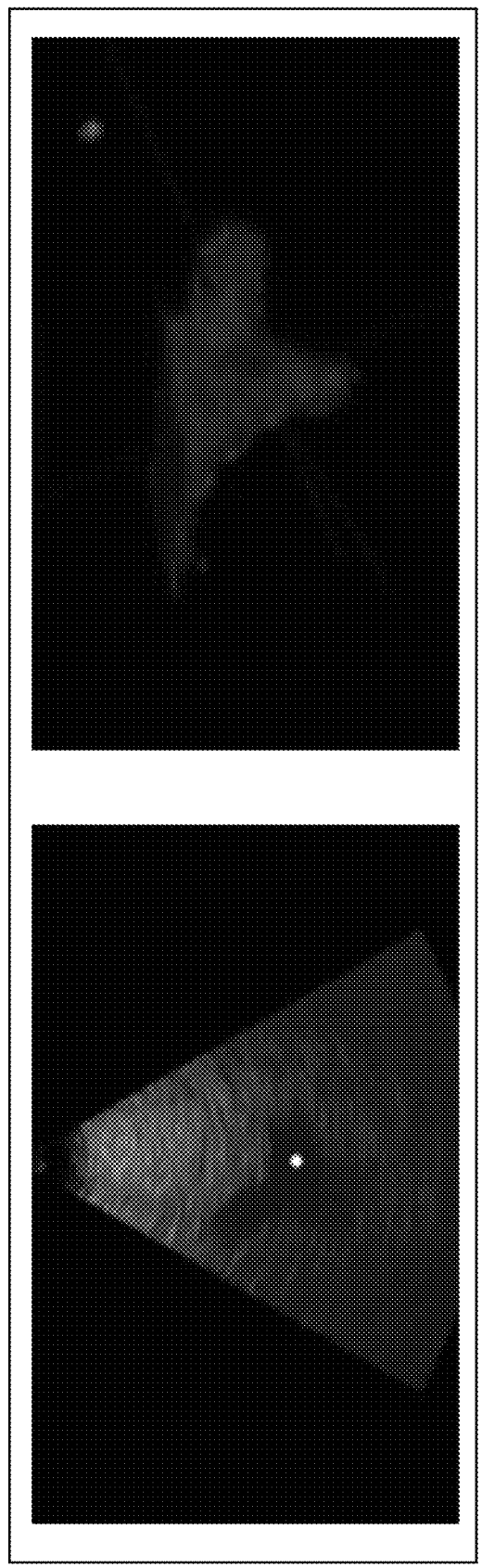

FIG. 54 is an exemplary user interface showing the application of auto-segmentation updated in real time and the 3D model of the ventricle and the avatar which is also updated in real time.

Figure 55:
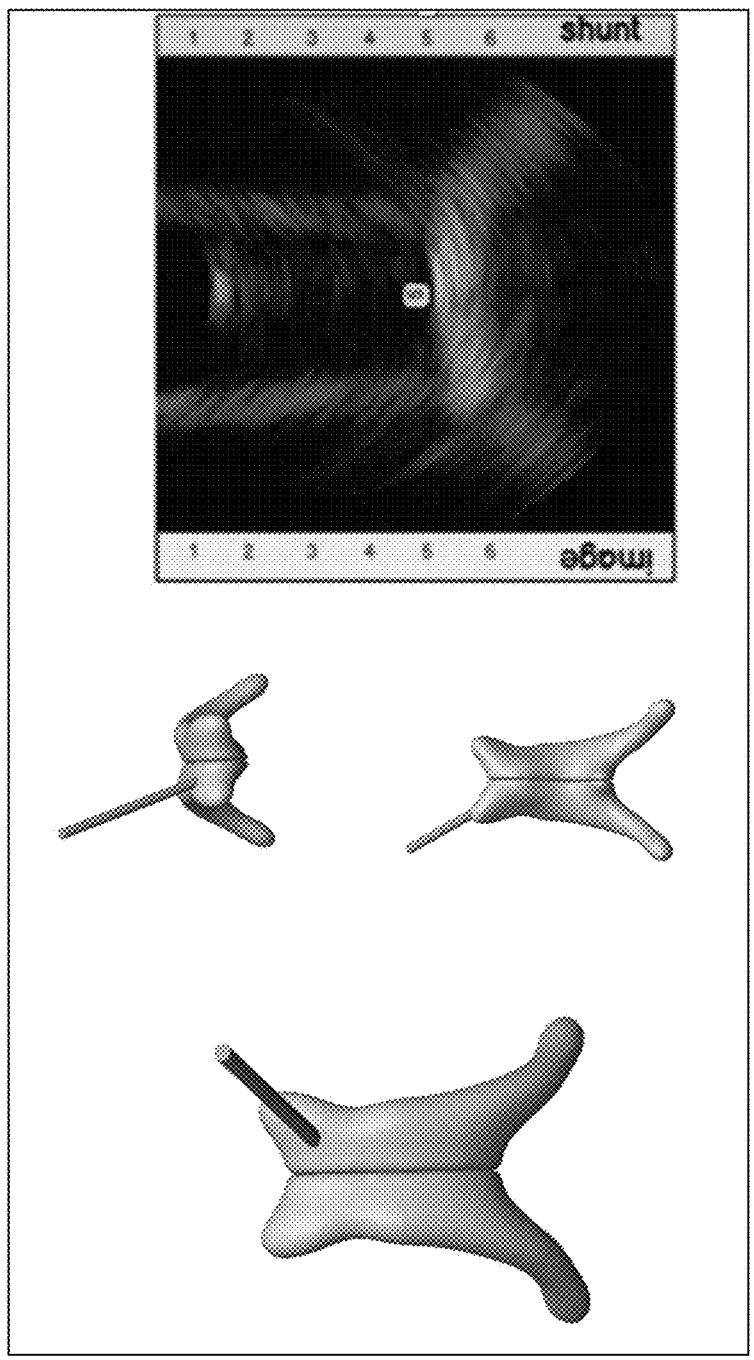

FIG. 55 is an exemplary user interface showing dominant and supportive images according to one embodiment.

Figure 56:
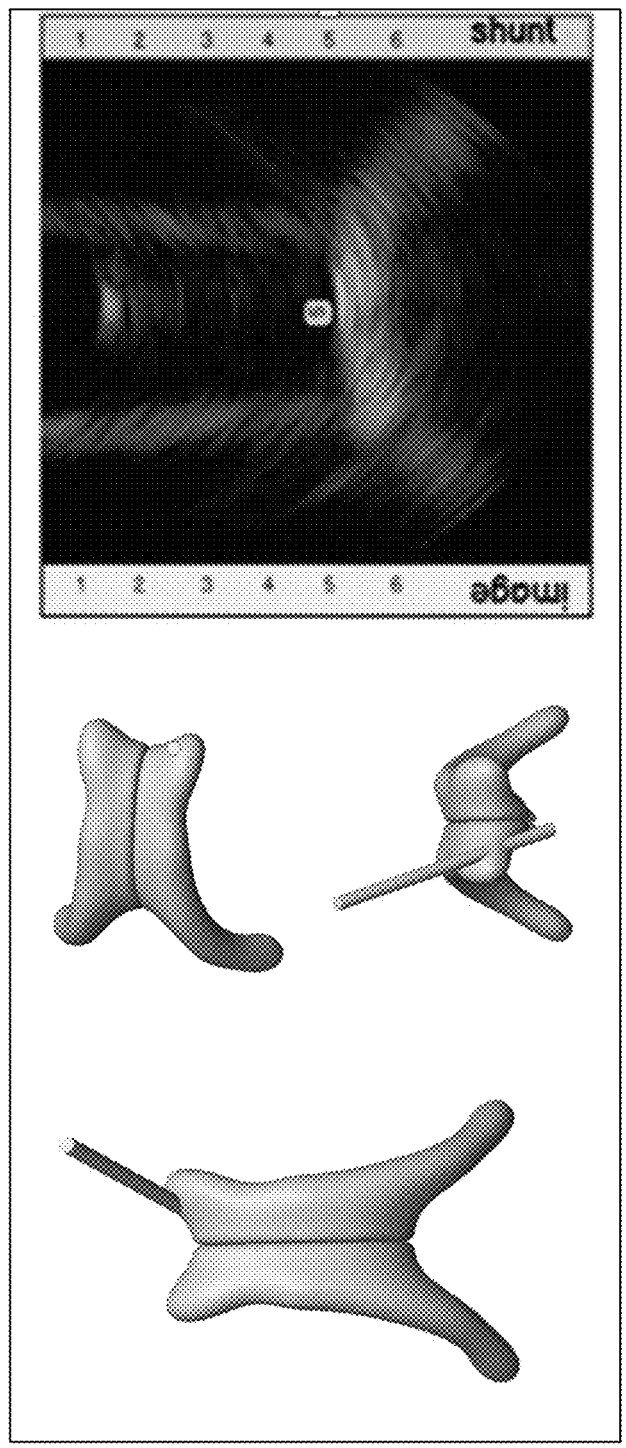

FIG. 56 is an exemplary user interface showing dominant and supportive images according to one embodiment.

Figure 57:
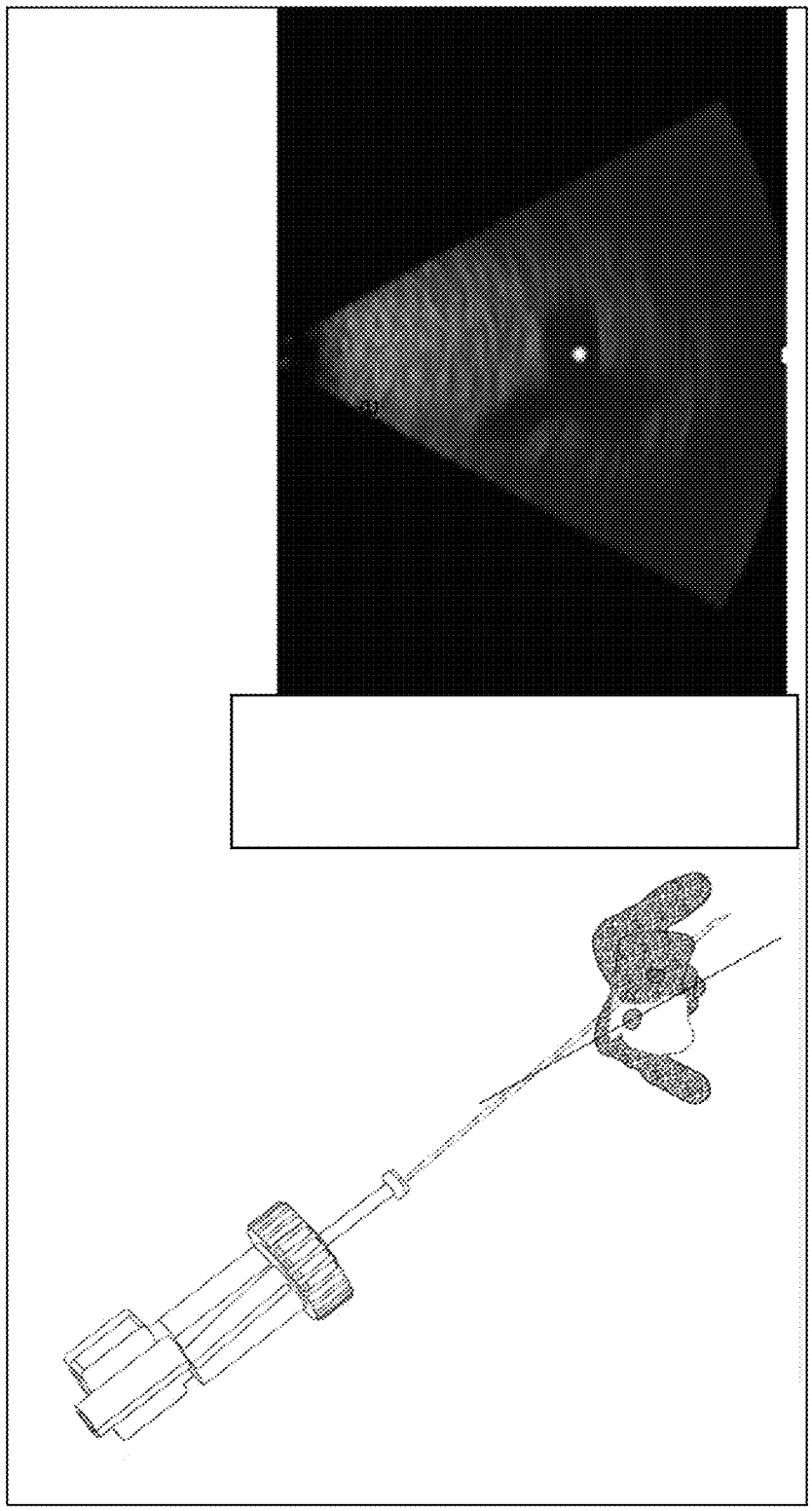

FIG. 57 is an exemplary user interface showing an avatar (overlay) image of the PID projected over the 3d image of the reconstructed lateral ventricle according to one embodiment.

Figure 58:
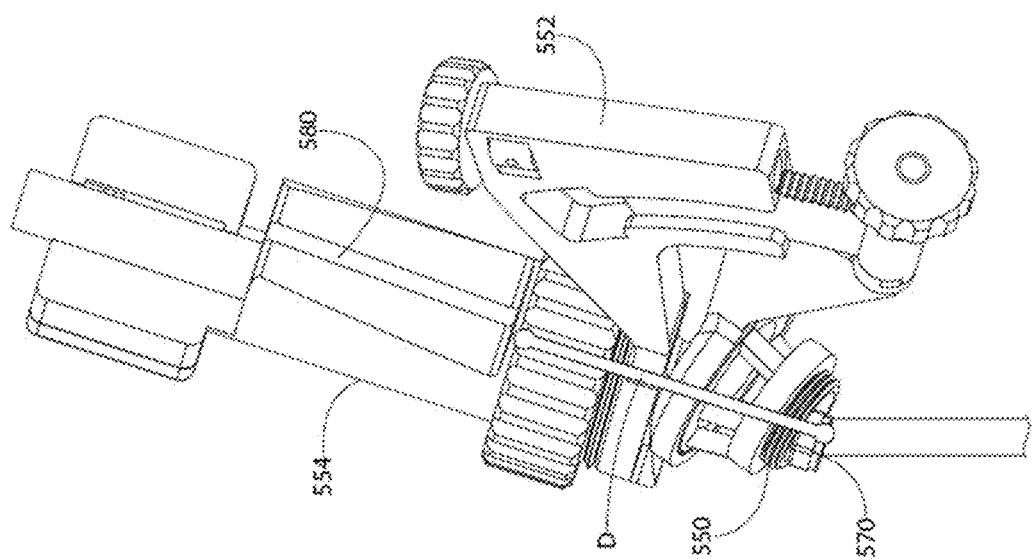

FIG. 58 is a diagram showing a distance between a face of the transducer to the entrance opening to the EVD guide according to one embodiment.

Figure 59:
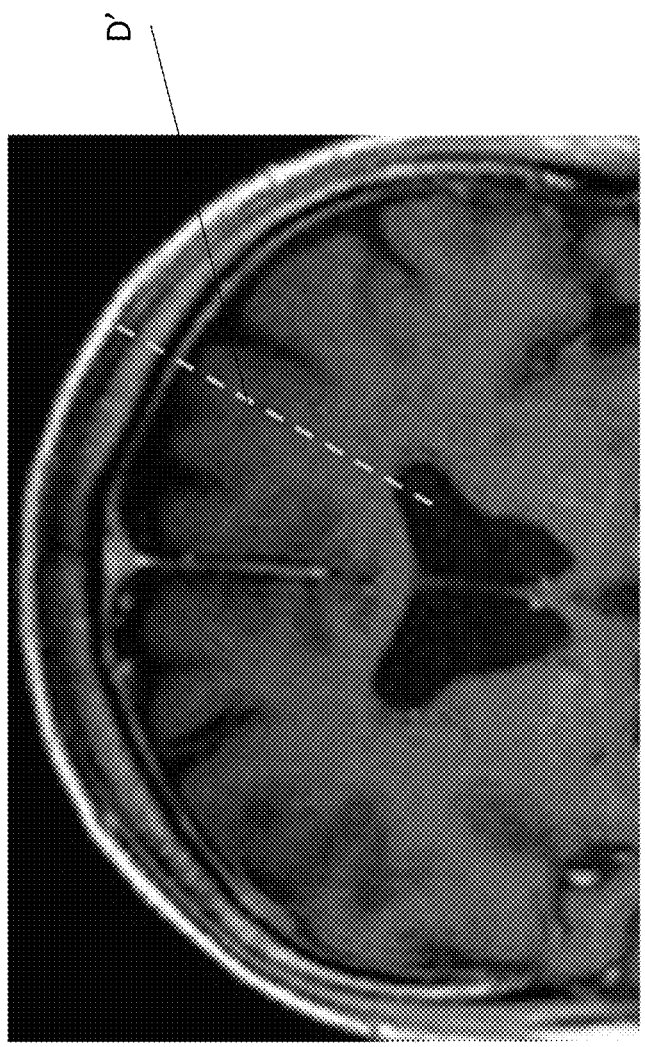

FIG. 59 is a diagram showing a distance from the transducer to the anterior horn of the ipsilateral ventricle according to one embodiment.

Figure 60:
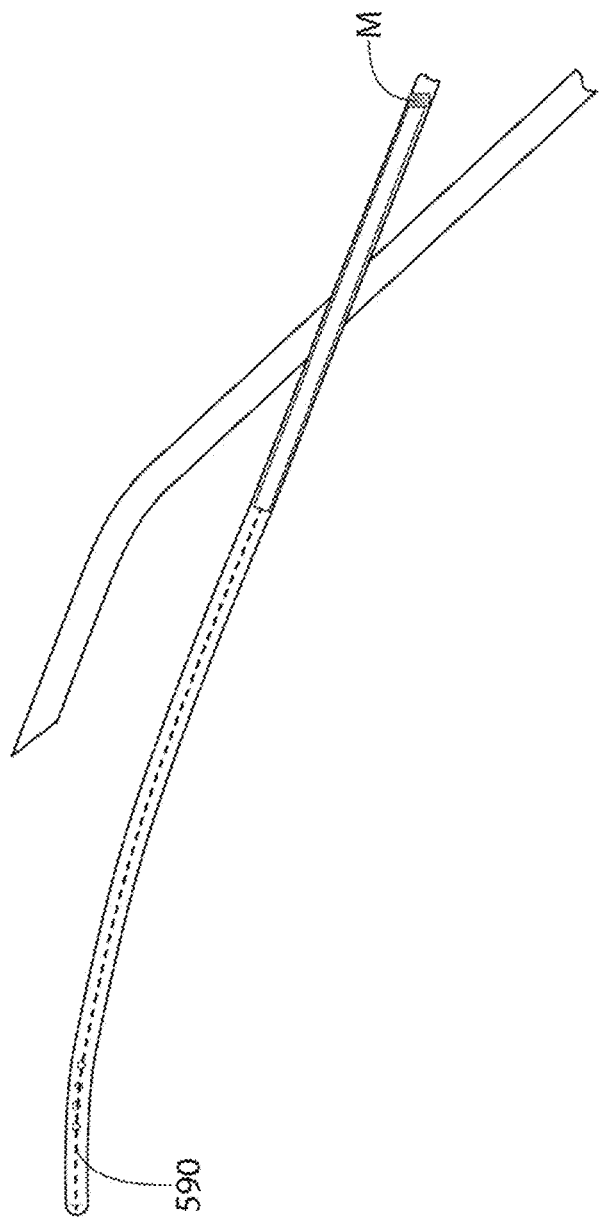

FIG. 60 is a diagram showing a marker on an EVD according to one embodiment.

Figure 61:
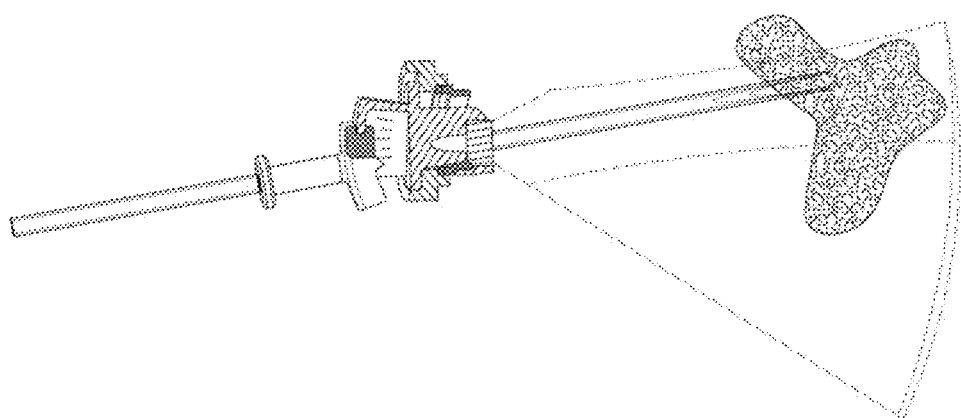

FIG. 61 is a diagram depicting out-of-plane imaging of an EVD entering a ventricle according to one embodiment.

Figure 62:
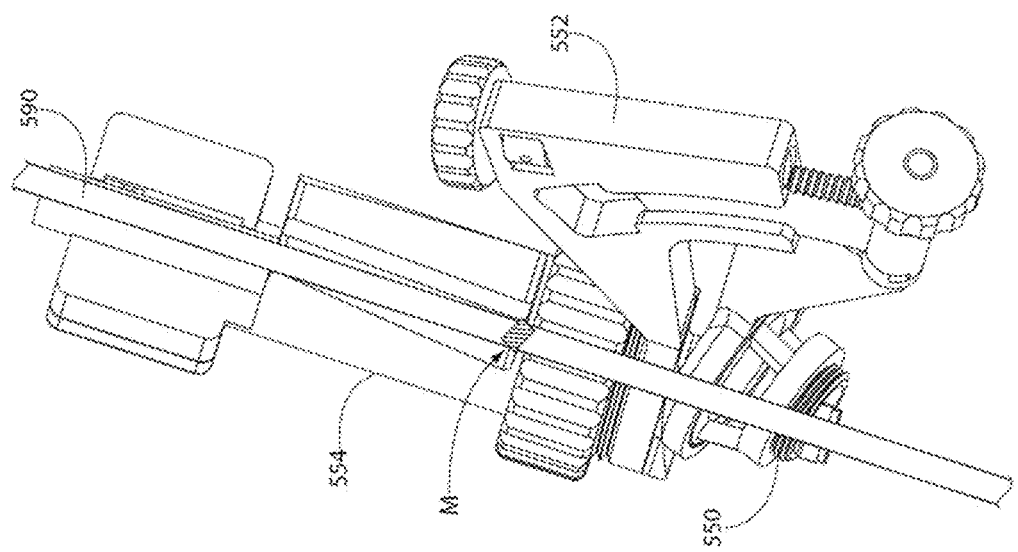

FIG. 62 is a diagram of an EVD inserted through the EVD guide tube and a mark on the EVD that confirms the EVD's proper placement along with the real time ultrasound image guidance information according to one embodiment.

Figure 63:
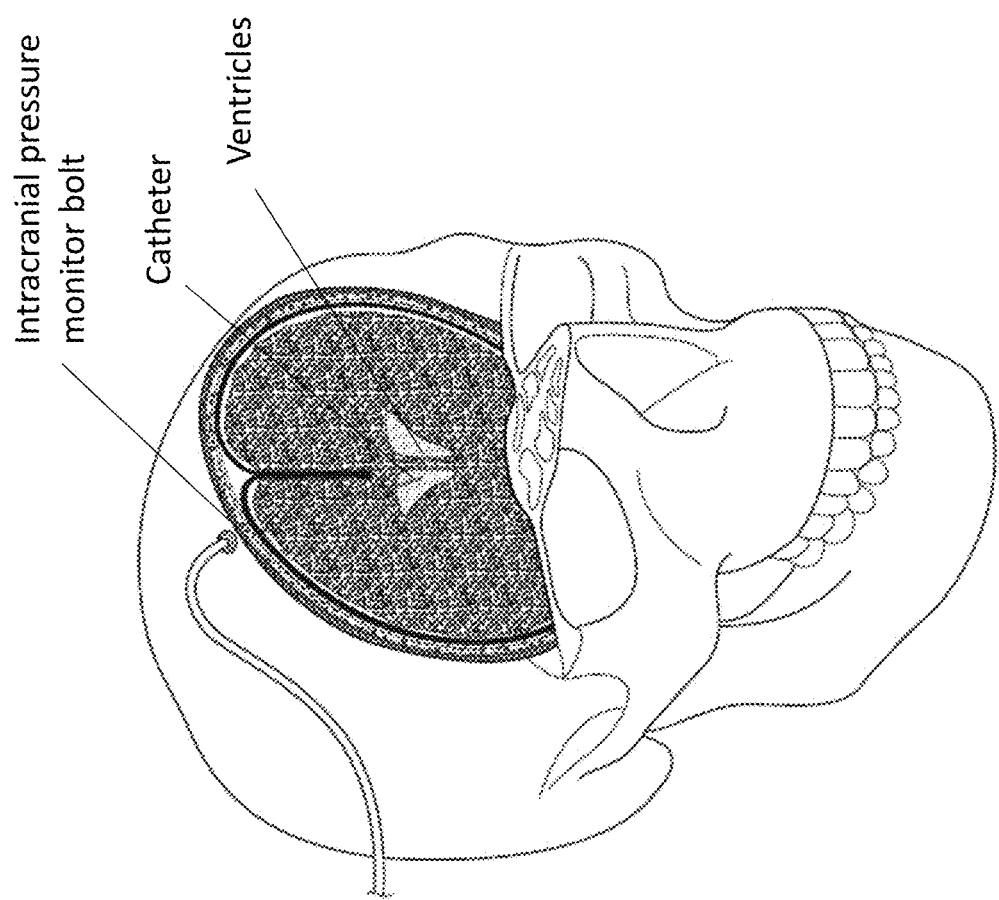

FIG. 63 is a diagram of an EVD in proper location according to one embodiment.

Figure 64:
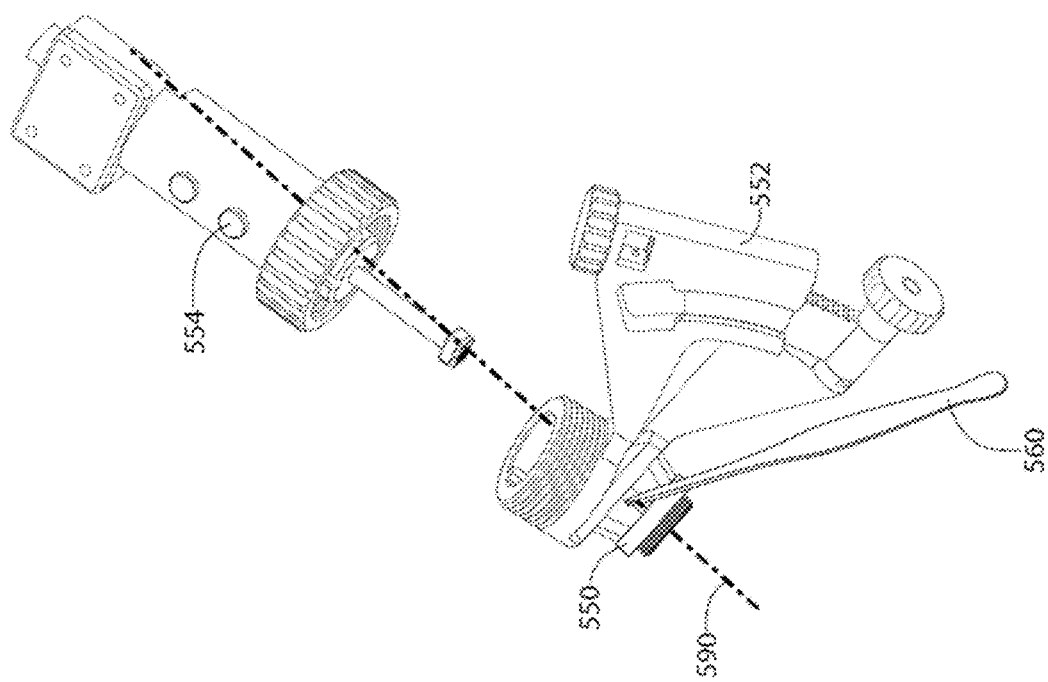

FIG. 64 is a diagram of forceps grabbing the EVD through the opening in the pillared anchor bolt and removing the ultrasound probe assembly over the EVD according to one embodiment.

Figure 65B:
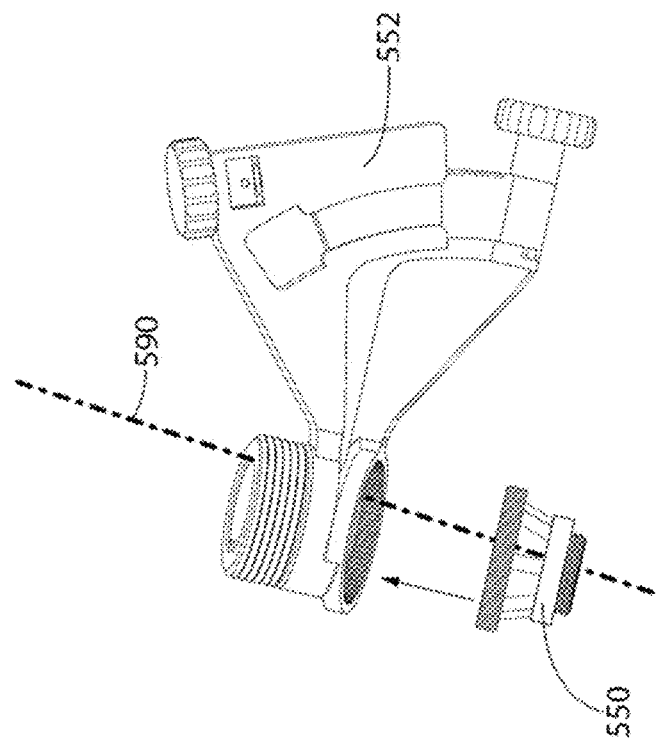
Figure 65A:
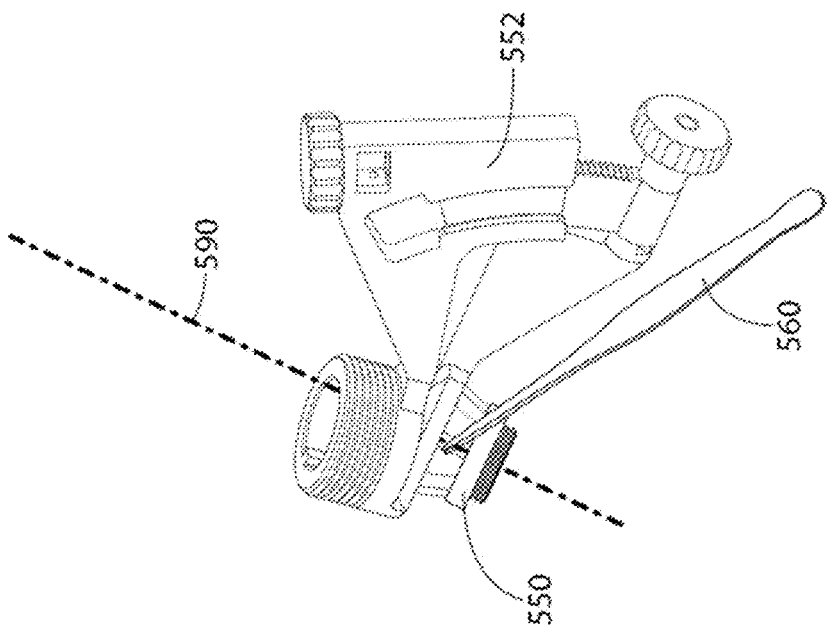

FIGS. 65A and 65B are diagrams of forceps grabbing the EVD through the opening in the pillared anchor bolt (FIG. 65A) and removing the PID guide over the EVD (FIG. 65B) according to one embodiment.

Figure 66:
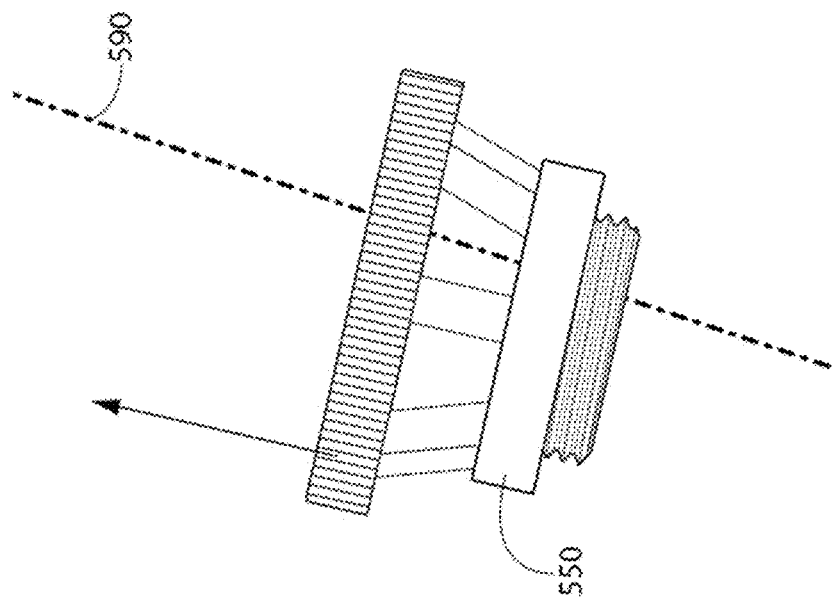

FIG. 66 is a diagram of removing the pillared anchor bolt over the EVD according to one embodiment.

DETAILED DESCRIPTION

The present invention provides fixation devices, locking assemblies, and methods for using the same. The fixation devices of the invention are capable of accurate insertion of medical devices by providing detection means of a patient's internal anatomy to localize a desired target. The devices are capable of at least partially locking into position to maintain accuracy.

Definitions

It is to be understood that the figures and descriptions of the present invention have been simplified to illustrate elements that are relevant for a clear understanding of the present invention, while eliminating, for the purpose of clarity, many other elements found in typical medical devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used herein, "imaging" may include ultrasonic imaging, be it one dimensional, two dimensional, three dimensional, or real-time three dimensional imaging (4D). Two dimensional images may be generated by one dimensional transducer arrays (e.g., linear arrays or arrays having a single row of elements). Three dimensional images may be produced by two dimensional arrays (e.g., those arrays with elements arranged in an n by n planar configuration) or by mechanically reciprocated, one dimensional transducer arrays. The term "imaging" also includes optical imaging, tomography, including optical coherence tomography (OCT), radiographic imaging, photoacoustic imaging, and thermography.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, "sonolucent" is defined as a property wherein a material is capable of transmitting ultrasound pulses without introducing significant interference, such that an acceptable acoustic response can be obtained from the body structure(s) of interest.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Locking Fixation Device

The present invention provides fixation devices, locking assemblies, and methods for using the same. The fixation devices of the invention are capable of accurate insertion of medical devices by providing detection means of a patient's internal anatomy and localizing a desired target. The devices are capable of at least partially locking into position to maintain accuracy.

Figure 1:
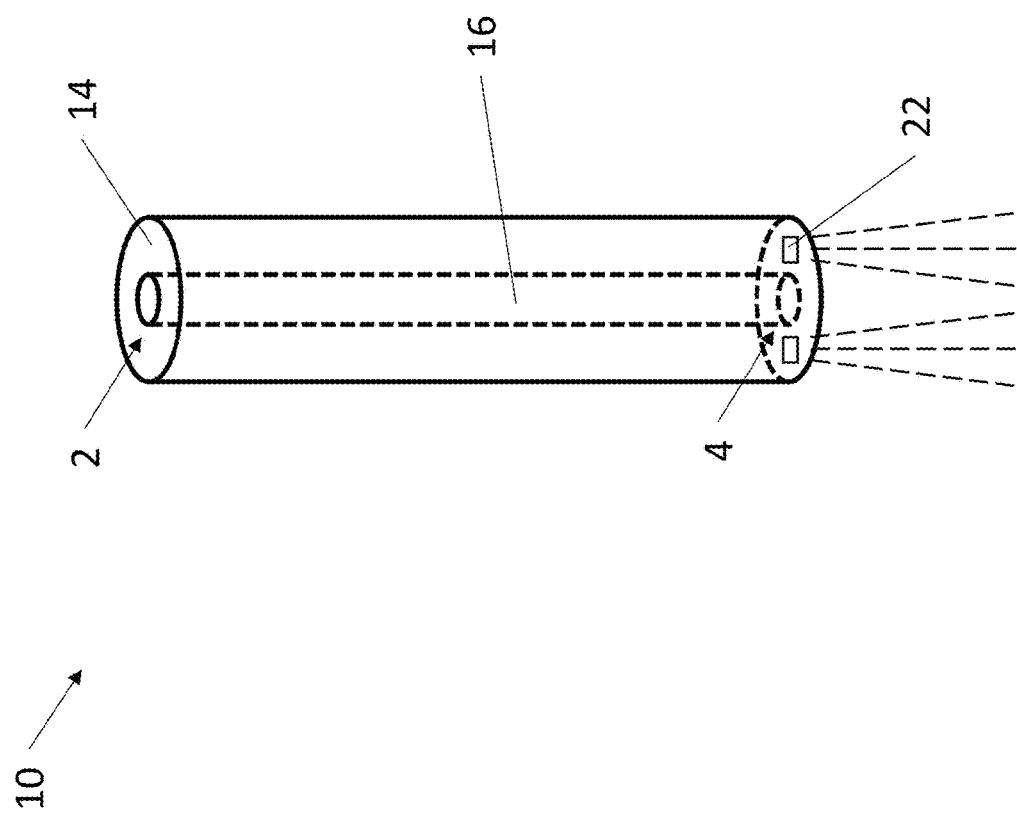
FIG. 1 depicts one embodiment of an exemplary fixation device.

Referring now to FIG. 1, an exemplary fixation device 10 is depicted. Fixation device 10 comprises elongate body 14, lumen 16, proximal end opening 2, distal end opening 4, and a plurality of transducers 22. Elongate body 14 can have any suitable shape. In one embodiment, elongate body 14 is cylindrical. There are no limitations to the particular sizes and dimensions elongate body 14 may have. Elongate body 14 can be made from any suitable material. For example, elongate body 14 can comprise silicones, plastics, polymers, metals, and the like. In one embodiment, elongate body 14 comprises a sonolucent material throughout. In one embodiment, elongate body 14 comprises a sonolucent material only at its distal end.

Elongate body 14 comprises lumen 16 and transducers 22. Lumen 16 extends through the entire length of elongate body 14 and connects proximal opening 2 and distal opening 4. Lumen 16 can have any suitable diameter. In one embodiment, lumen 16 has a diameter of at least 0.1 mm. In one embodiment, lumen 16 has a diameter of 1.2 mm. In various embodiments, lumen 16 has a diameter between 0.5 mm and 10 mm. In one embodiment, lumen 16 is dimensioned to fit a catheter.

Transducers 22 can be any suitable device capable of emitting energy, receiving energy, or both energy emission and reception. In various embodiments, elongate body 14 comprises one, two, three, four, or more transducers 22. Elongate body 14 may also comprise combinations of different transducers 22. For example, elongate body 14 may comprise a combination of emitting transducers and receiving transducers, or a combination of transducers that respond to different types of energy. Non-limiting examples of types of transducers suitable for use with the present invention include: ultrasonic transducers, optical sensors, thermal sensors, electromagnetic sensors, photoelectric transducers, laser diodes, radio transducers, Doppler, x-ray, particle sensors, chemical sensors, piezoelectric sensors, and the like.

Lumen 16 can have any suitable cross-section, such as a cross-section that is circular, elliptical, polygonal, or keyed. Lumen 16 may be centered or off-center in fixation device 10. Lumen 16 of fixation device 10 is amenable to guiding any various types of medical devices. For example, lumen 16 may accommodate additional probes or instruments appropriate for any given medical procedure. Non-limiting examples of additional components include catheters, microforceps, microscalpels, biopsy needles, radiofrequency ablation probes, cryoablation probes, suturing instruments, syringes, and the like. In some embodiments, lumen 16 comprises a circular cross-section and is sized and dimensioned to permit an inserted instrument to rotate.

Figure 2A:
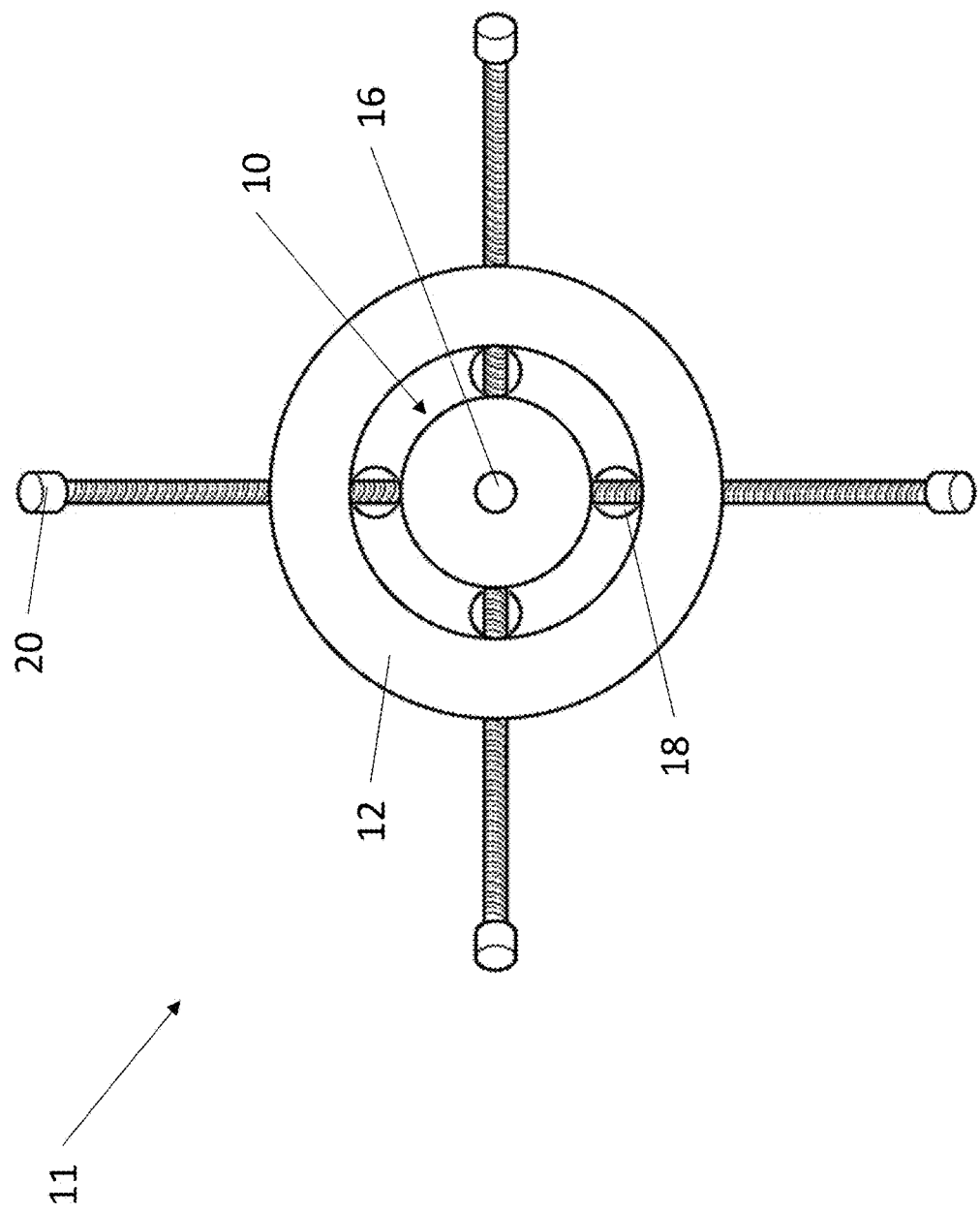
FIG. 2A and FIG. 2B depict an exemplary fixation device coupled with a grommet locking assembly.
Figure 2B:
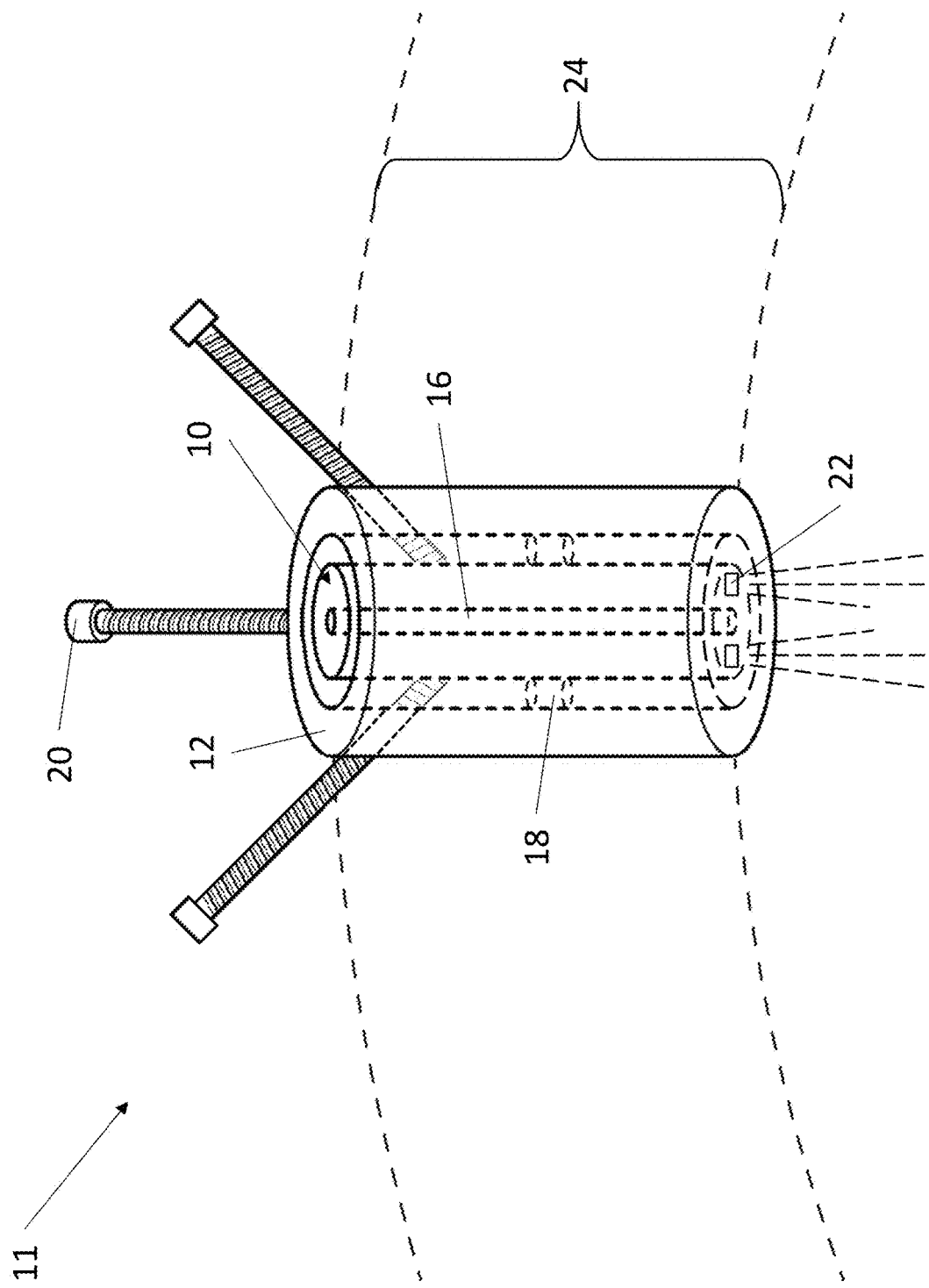

Referring now to FIG. 2A, a top-down view of an exemplary grommet locking assembly 11 is depicted. Grommet locking assembly 11 comprises grommet 12, fixation device 10, fulcrum 18, and locking member 20. Referring now to FIG. 2B, an isometric view of an exemplary grommet locking assembly 11 is depicted. Grommet 12 fits within an opening on a patient to provide access to the interior of a patient's anatomy.

In various embodiments, the exterior surface of grommet 12 can comprise features to enhance the fit of grommet 12 within a patient, such as ridges, flanges, threads, barbs, and the like. Grommet 12 can be made from any suitable biocompatible material, such as stainless steel, cobalt, titanium, aluminum oxide, zirconia, calcium phosphate, silicon, polyethylene, polyvinyl chloride, polyurethane, polylactide, and the like. In one embodiment, grommet 12 comprises a sonolucent material throughout. In one embodiment, grommet 12 comprises a sonolucent material only at its distal end.

Grommet 12 can have any suitable shape. Non-limiting examples of grommet 12 shapes include cylinders, cubes, cuboids, and the like. There are no limitations to the particular sizes and dimensions grommet 12 may have.

Grommet 12 comprises a lumen that extends through the entire length of grommet 12. Within the lumen, grommet 12 comprises a plurality of fulcrums 18. For example, in one exemplary embodiment, grommet 12 comprises at least two fulcrums 18. Fulcrums 18 attach to the lumen of grommet 12 and to the exterior surface of fixation device 10. Fulcrums 18 may be made from any suitable material. In one embodiment, fulcrums 18 are made from a pliable material, such as a biocompatible rubber, polymer, or gel. Fulcrums 18 secure fixation device 10 to grommet 12 while providing fixation device 10 with the ability to move independently from grommet 12. For example, pliable fulcrums 18 are deformable to allow fixation device 10 to be oriented within grommet 12. Fixation device 10 can be oriented by angling to any degree. In one embodiment, fixation device 10 can be oriented by angling up to 20 degrees from vertical. In another embodiment, fixation device 10 can be oriented by angling by up to 45 degrees from vertical. In one embodiment, instead of fulcrums 18, fixation device 10 is attached to grommet 12 by a pliable membrane.

Grommet 12 further comprises at least one locking member 20. Locking member 20 can be any suitable locking member, including but not limited to: a screw, a bolt, a pin, an adhesive, and a clamp. For example, in one exemplary embodiment, a grommet locking assembly 11 may comprise locking members 20 that are screws that pass through grommet 12 to contact fixation device 10. The screws may be screwed in or out of grommet 12 to vary and lock the orientation of fixation device 10. In other embodiments, the locking member 20 may be mechanical, electro-mechanical, magnetic, or adhesive.

Referring now to FIG. 3, a side view cross section of an exemplary cup locking assembly 30 is depicted. Cup locking assembly 30 comprises fixation device 10 and cup 32. Fixation device 10 further comprises ball adapter 36. Cup 32 fits within an opening on a patient to provide access to the interior of a patient's anatomy.

In various embodiments, the exterior surface of cup 32 can comprise features to enhance the fit of cup 32 within a patient, such as ridges, flanges, threads, barbs, and the like. Cup 32 can be made from any suitable biocompatible material, such as stainless steel, cobalt, titanium, aluminum oxide, zirconia, calcium phosphate, silicon, polyethylene, polyvinyl chloride, polyurethane, polylactide, and the like. In one embodiment, cup 32 comprises a sonolucent material throughout. In one embodiment, cup 32 comprises a sonolucent material only at its distal end.

Cup 32 comprises a base member and perimeter sidewalls forming an open top. The base member comprises at least one opening 34. Cup 32 can have any suitable shape. In some embodiments, cup 32 has the shape of a conical frustum with wide diameter facing away from the patient and a narrow diameter facing towards the patient. Cup 32 can have any suitable dimensions. For example, cup 32 can have a height of 5 to 50 mm, and a diameter of 5 to 50 mm.

The interior of cup 32 is dimensioned to fit ball adapter 36 of fixation device 10. Ball adapter 36 is able to rotate freely within cup 32, like a ball joint, to provide fixation device 10 with an orientation. Fixation device 10 can be oriented by angling to any degree. In one embodiment, fixation device 10 can be oriented by angling up to 20 degrees from vertical. In another embodiment, fixation device 10 can be oriented by angling up to 45 degrees from vertical.

Cup 32 further comprises locking member 20. Locking member 20 can be any suitable locking member, including but not limited to: a screw, a bolt, a pin, an adhesive, and a clamp. For example, in one embodiment, locking member 20 is a screw. The screw may be screwed in or out of cup 32 such that when the screw contacts ball adapter 36, the screw arrests the movement of ball adapter 36, thereby locking the orientation of fixation device 10. In other embodiments, the locking member 20 may be mechanical, electro-mechanical, magnetic, or adhesive.

Figure 4A:
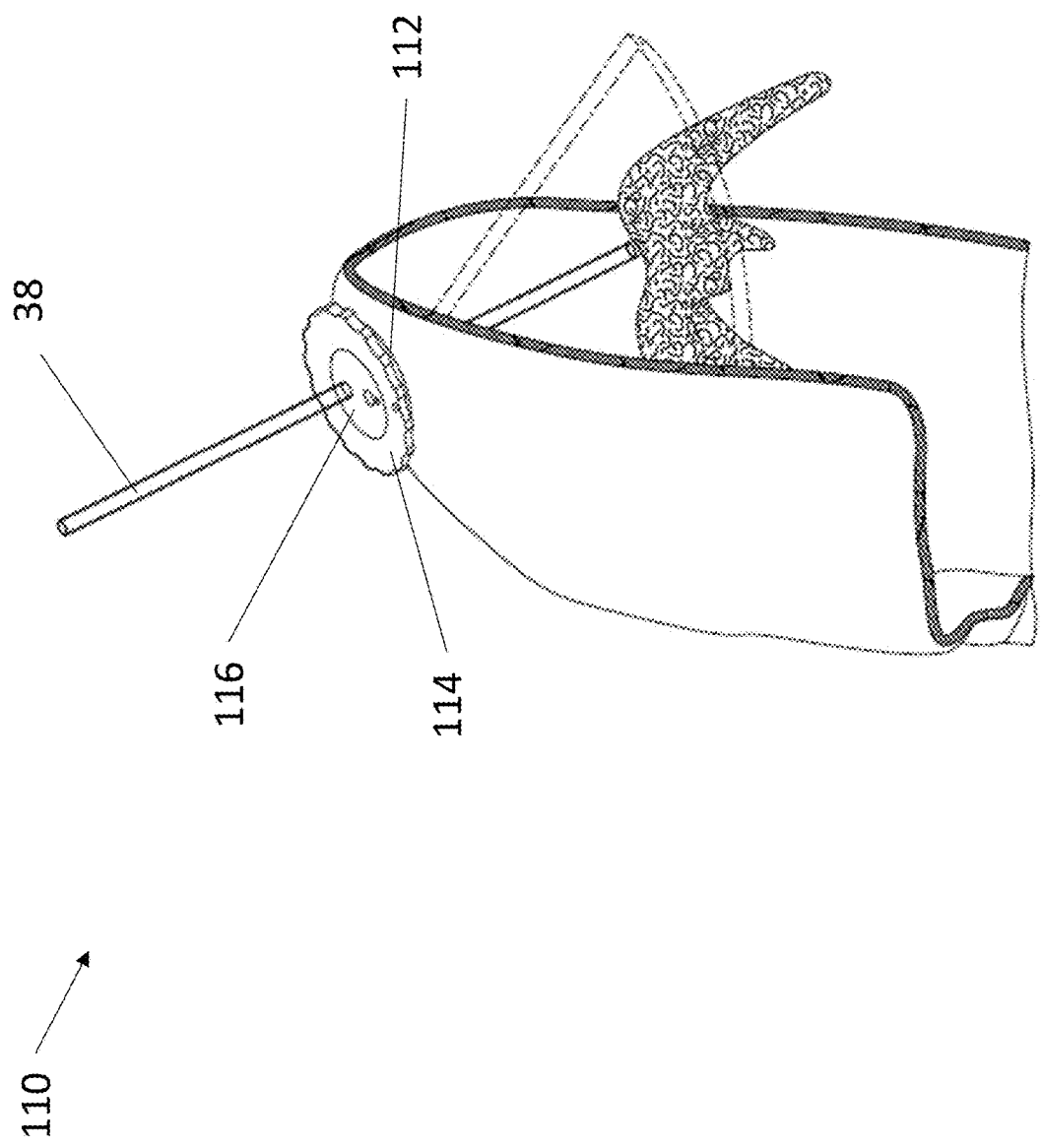
FIG. 4A and FIG. 4B depict an exemplary single shim 3 Degrees of Freedom (DoF) device.
Figure 4B:
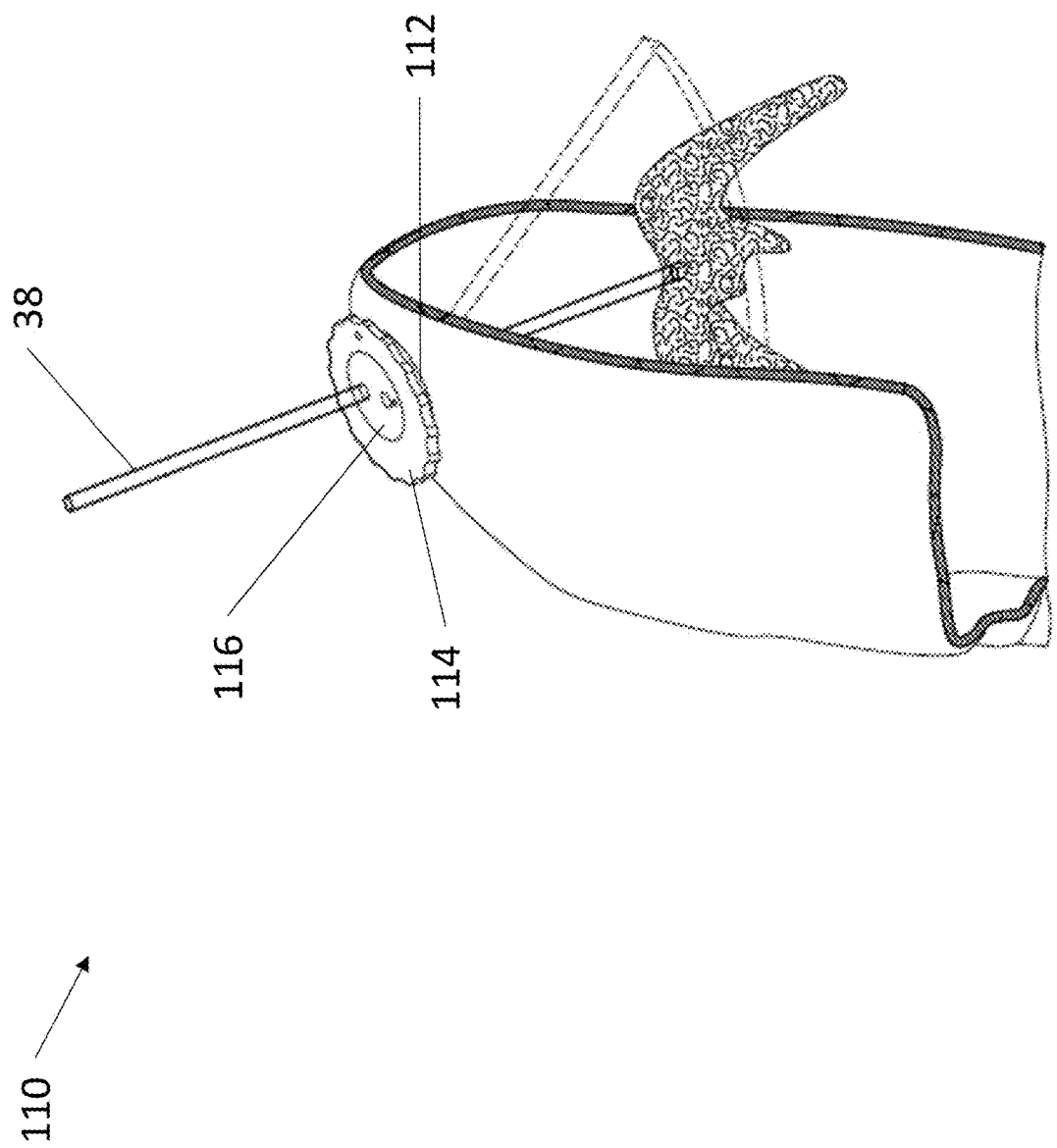

In various embodiments, the present invention relates to fixation devices having fixed degrees of freedom for precise movement. Referring now to FIG. 4A and FIG. 4B, an exemplary single shim 3 Degrees of Freedom (DoF) fixation device 110 is depicted. Device 110 comprises anchor 112, rotating shim 114, and rotating transducer housing 116. Anchor 112 is secured within a burr hole, such as that of a skull depicted in FIG. 4A and FIG. 4B. Rotating shim 114 fits within anchor 112. In various embodiments, rotating shim 114 comprises an angle, wherein the angle can be any suitable angle between 1 and 10 degrees. Rotating shim 114 comprises a space at its center for accepting rotating transducer housing 116. Transducer housing 116 comprises at least one ultrasonic transducer and at least one aperture for accepting a medical instrument 38. The first DoF of device 110 is the vertical travel of medical instrument 38. The second DoF is the rotation of transducer housing 116. The third DoF is the rotation of shim 114.

Figure 5:
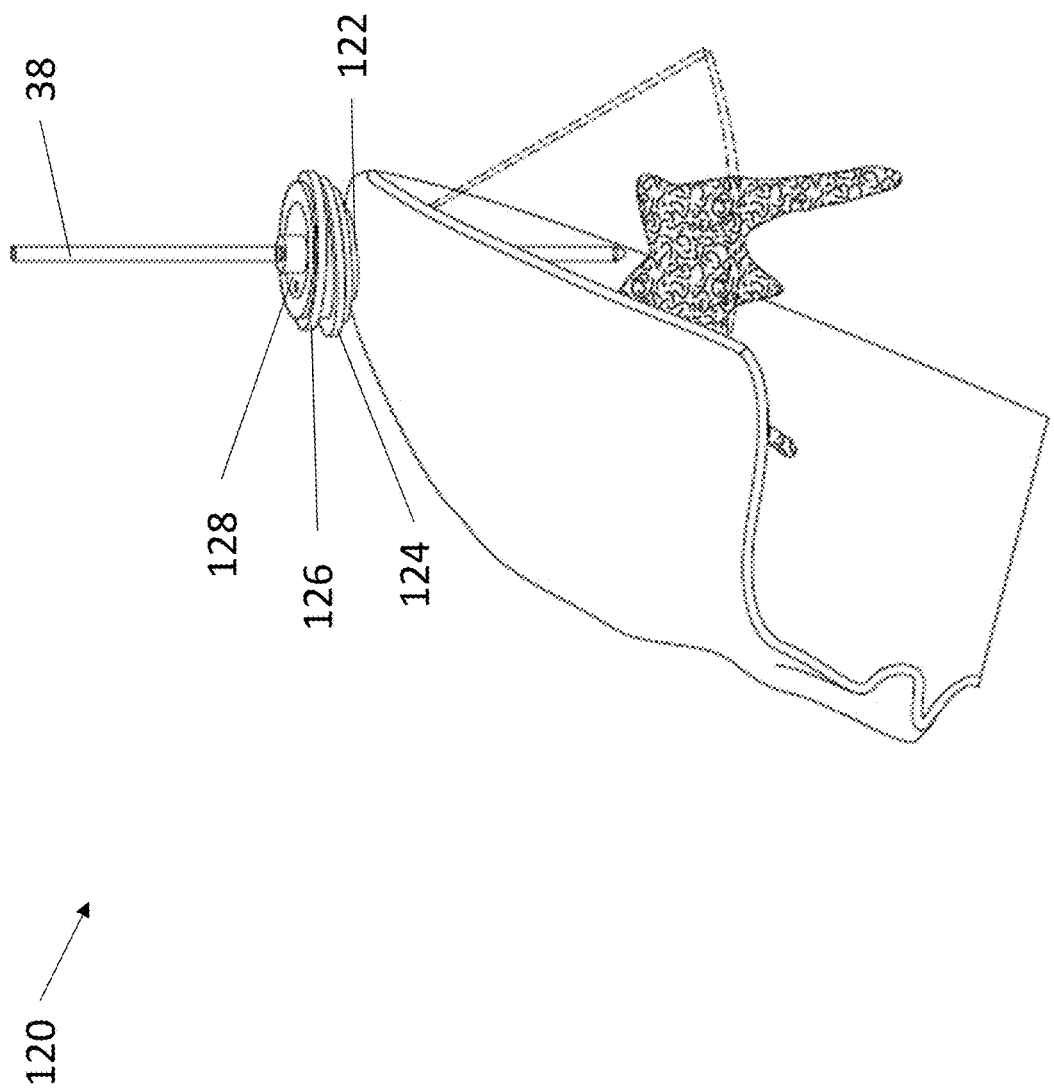
FIG. 5 depicts an exemplary double shim 3 DoF device.

Referring now to FIG. 5, an exemplary double shim 3 DoF fixation device 120 is depicted. Device 120 comprises anchor 122, a first rotating shim 124, a second rotating shim 126, and a rotating transducer housing 128. Similarly to the components of device 110, anchor 122 secures within a burr hole, wherein anchor 122 holds a first rotating shim 124. The second rotating shim 126 fits on top of the first rotating shim 124, and the second rotating shim 126 comprises a space at its center for accepting rotating transducer housing 128. In various embodiments, transducer housing 128 comprises at least one ultrasonic transducer and at least one aperture for accepting a medical instrument 38. The first rotating shim 124 and the second rotating shim 126 each comprise an angle, wherein the angle can be any suitable angle between 1 and 10 degrees. In various embodiments, the first rotating shim 124 can have the same angle or a different angle than the second rotating shim 126. The first DoF of device 120 is the vertical travel of medical instrument 38. The second DoF of device 120 is the rotation of transducer housing 128. The third DoF of device 120 is the rotation of first shim 124, second shim 126, or both.

Figure 6:
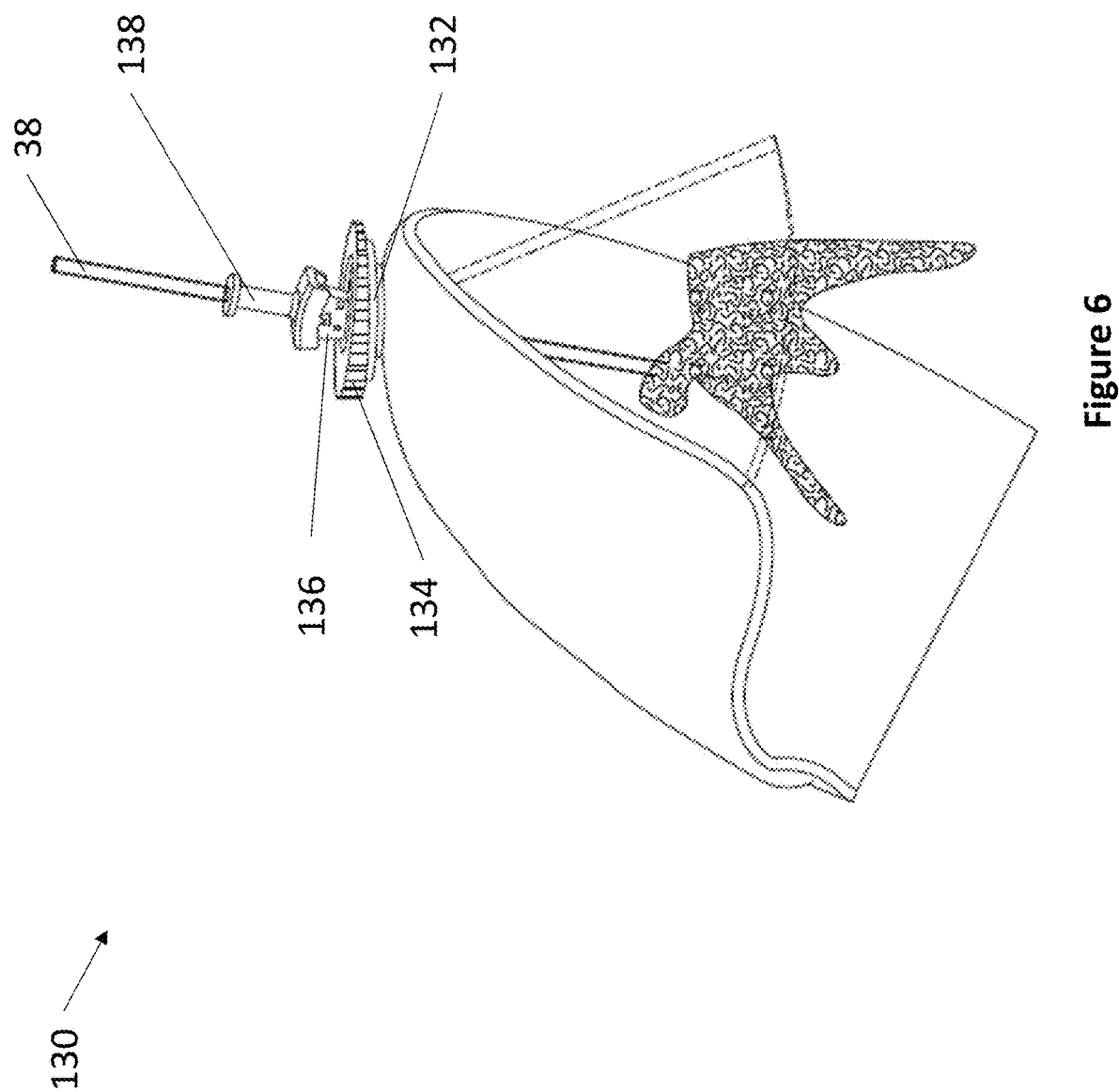
FIG. 6 depicts an exemplary single shim 4 DoF device.

Referring now to FIG. 6, an exemplary single shim 4 DoF fixation device 130 is depicted. Device 130 comprises anchor 132, rotating shim 134, transducer housing 136, and lever 138. As described elsewhere herein, anchor 132 secures within a burr hole. Rotating shim 134 fits within anchor 132. In various embodiments, rotating shim 134 comprises an angle, wherein the angle can be any suitable angle between 1 and 10 degrees. Rotating shim 134 comprises a space at its center for accepting transducer housing 136. Transducer housing 136 comprises at least one ultrasonic transducer and a lever housing, whereupon lever 138 actuates. The lever housing may comprise regularly spaced markings to indicate the relative position of lever 138. In various embodiments, lever 138 may be angled between 5 and 15 degrees from vertical. Lever 138 comprises at least one aperture for accepting a medical instrument 38. The first DoF of device 130 is the vertical travel of medical instrument 38. The second DoF of device 130 is the angulation of lever 138. The third DoF of device 130 is the rotation of transducer housing 136. The fourth DoF of device 130 is the rotation of shim 134.

Figure 7A:
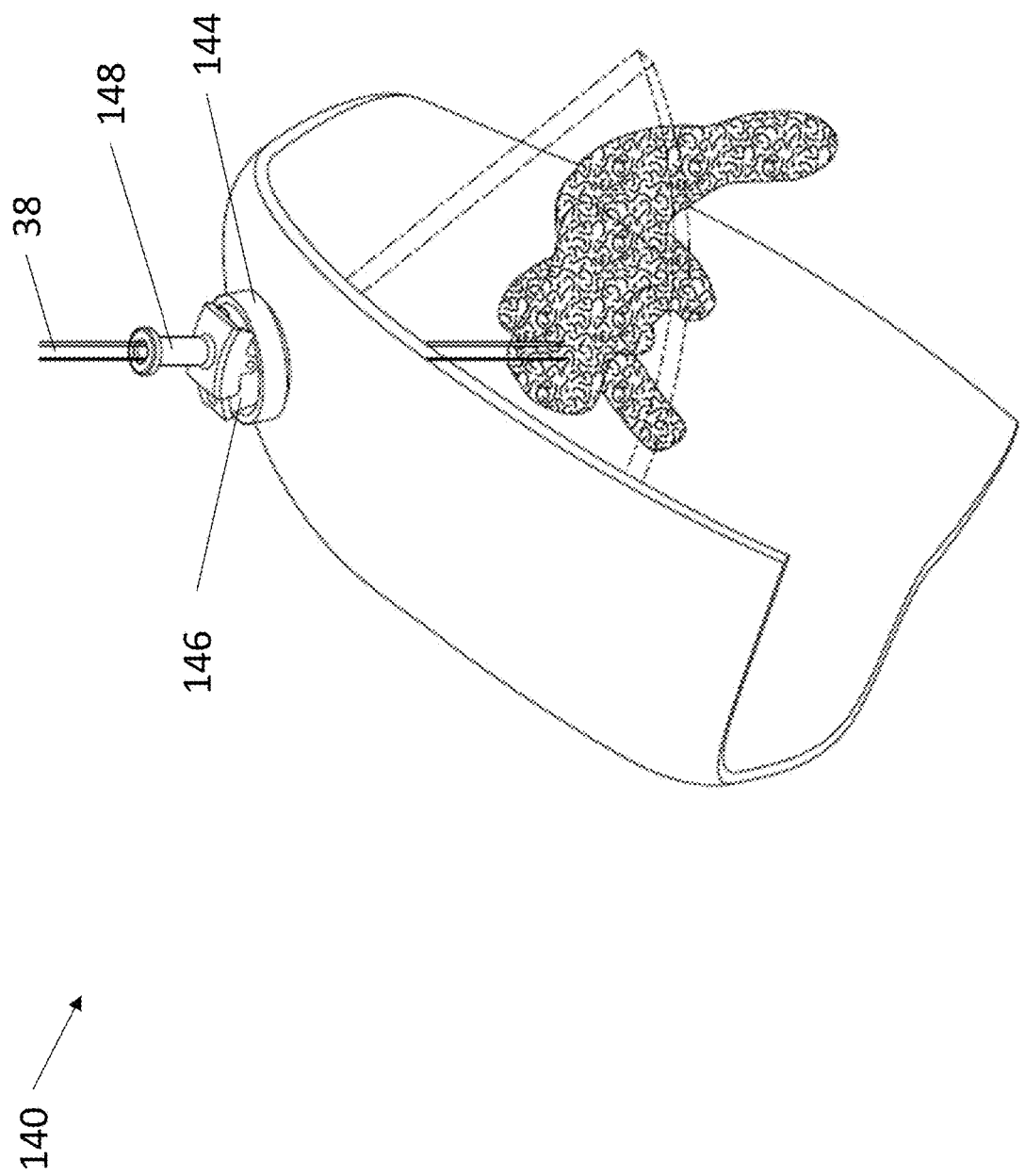
FIG. 7A through FIG. 7C depict an exemplary levered 3 DoF device.
Figure 7B:
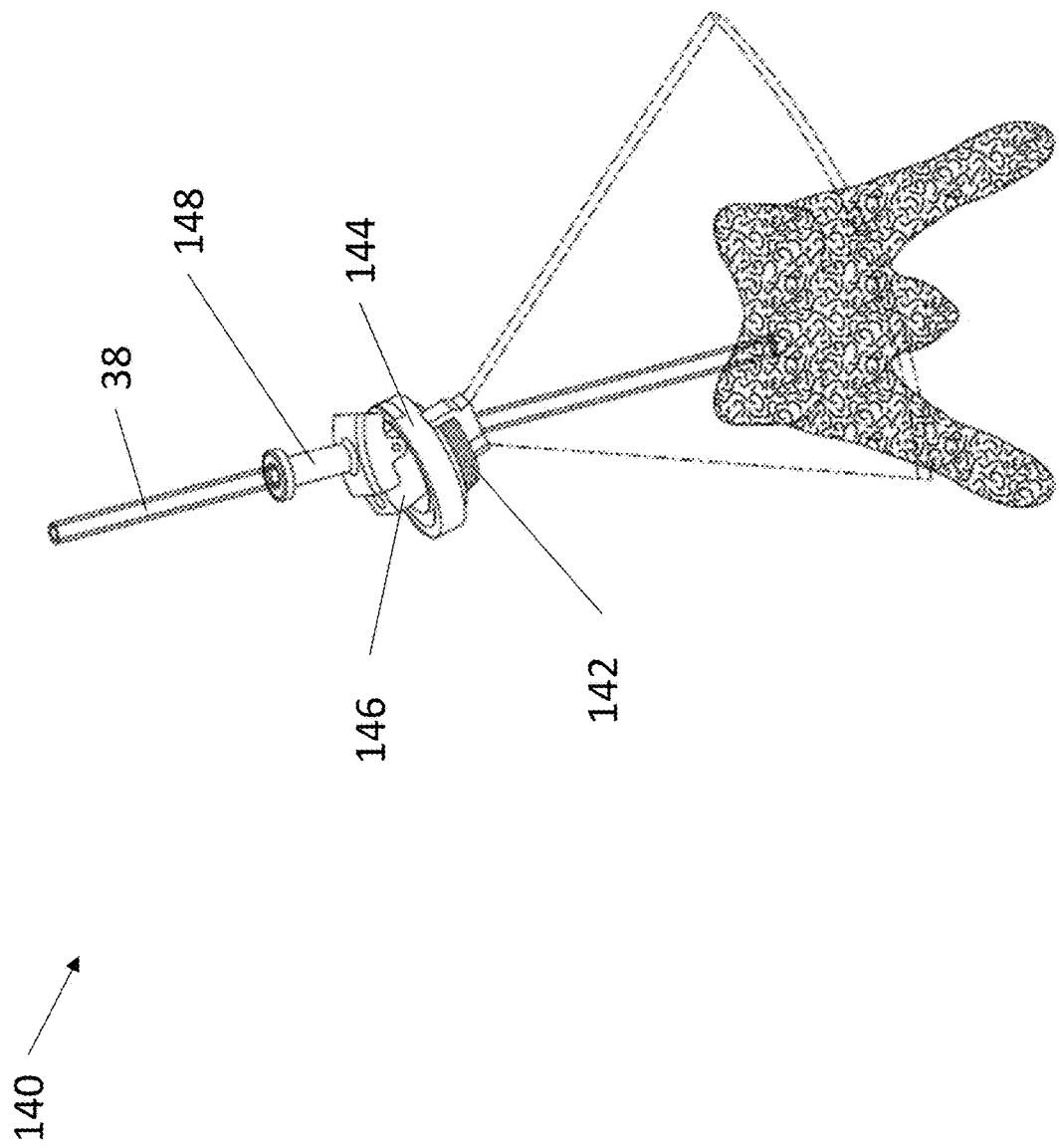
Figure 7C:
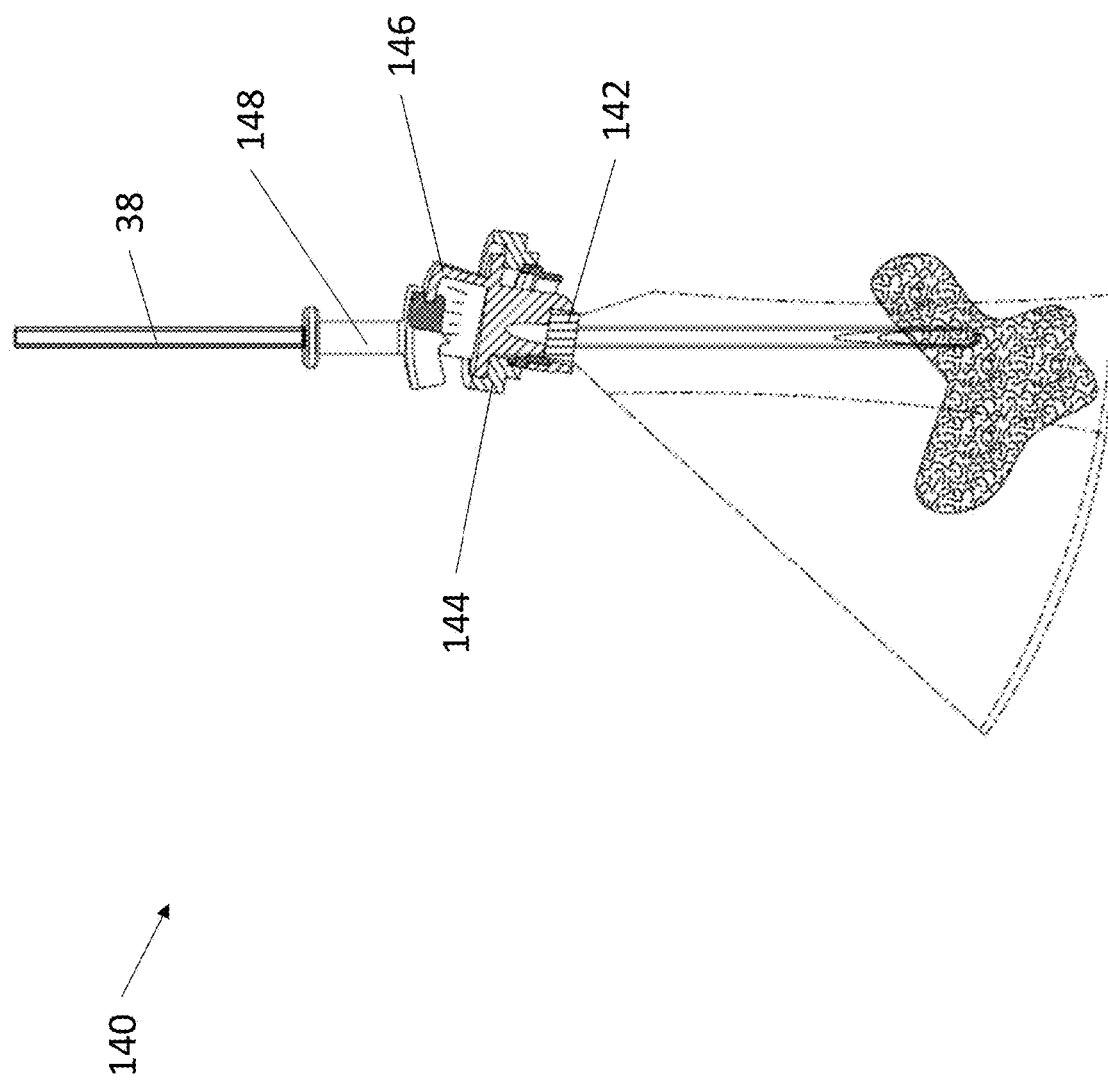

Referring now to FIG. 7A through FIG. 7B, an exemplary levered 3 DoF fixation device 140 is depicted. Device 140 comprises anchor 142, rotatable housing 144, transducer housing 146, and lever 148. As described elsewhere herein, anchor 142 secures within a burr hole, and articulating component 144 fits within anchor 142. Rotatable housing 144 comprises a space at its center for accepting transducer housing 146. Transducer housing 146 comprises at least one ultrasonic transducer and a lever housing, whereupon lever 148 actuates. The lever housing may comprise regularly spaced markings to indicate the relative position of lever 148. In various embodiments, lever 148 may be angled between 5 and 15 degrees from vertical. Lever 148 comprises at least one aperture for accepting a medical instrument 38. The first DoF of device 140 is the vertical travel of medical instrument 38. The second DoF of device 140 is the angulation of lever 148. The third DoF of device 140 is the rotation of transducer housing 146.

Figure 8A:
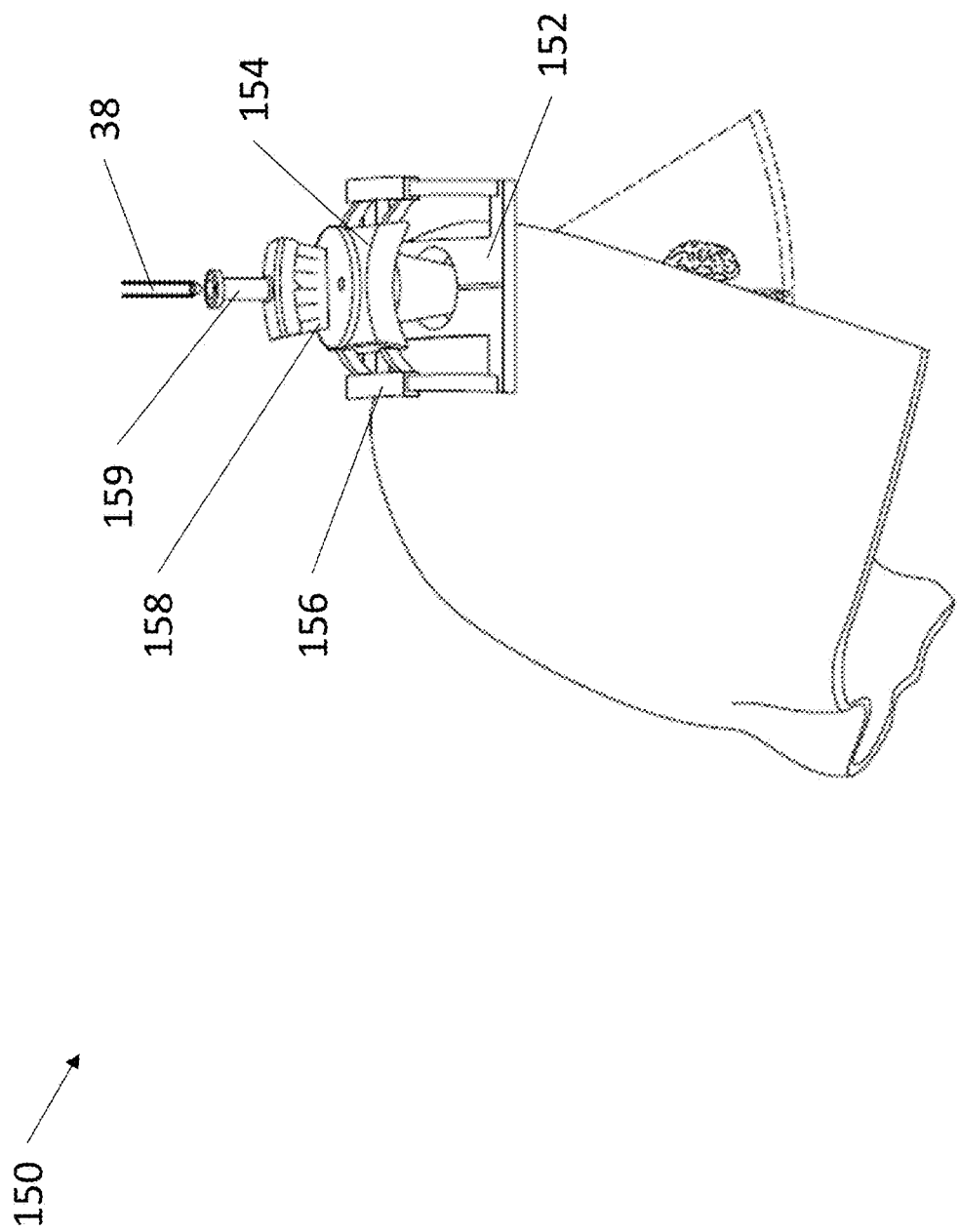
FIG. 8A and FIG. 8B depict an exemplary 5 DoF device.
Figure 8B:
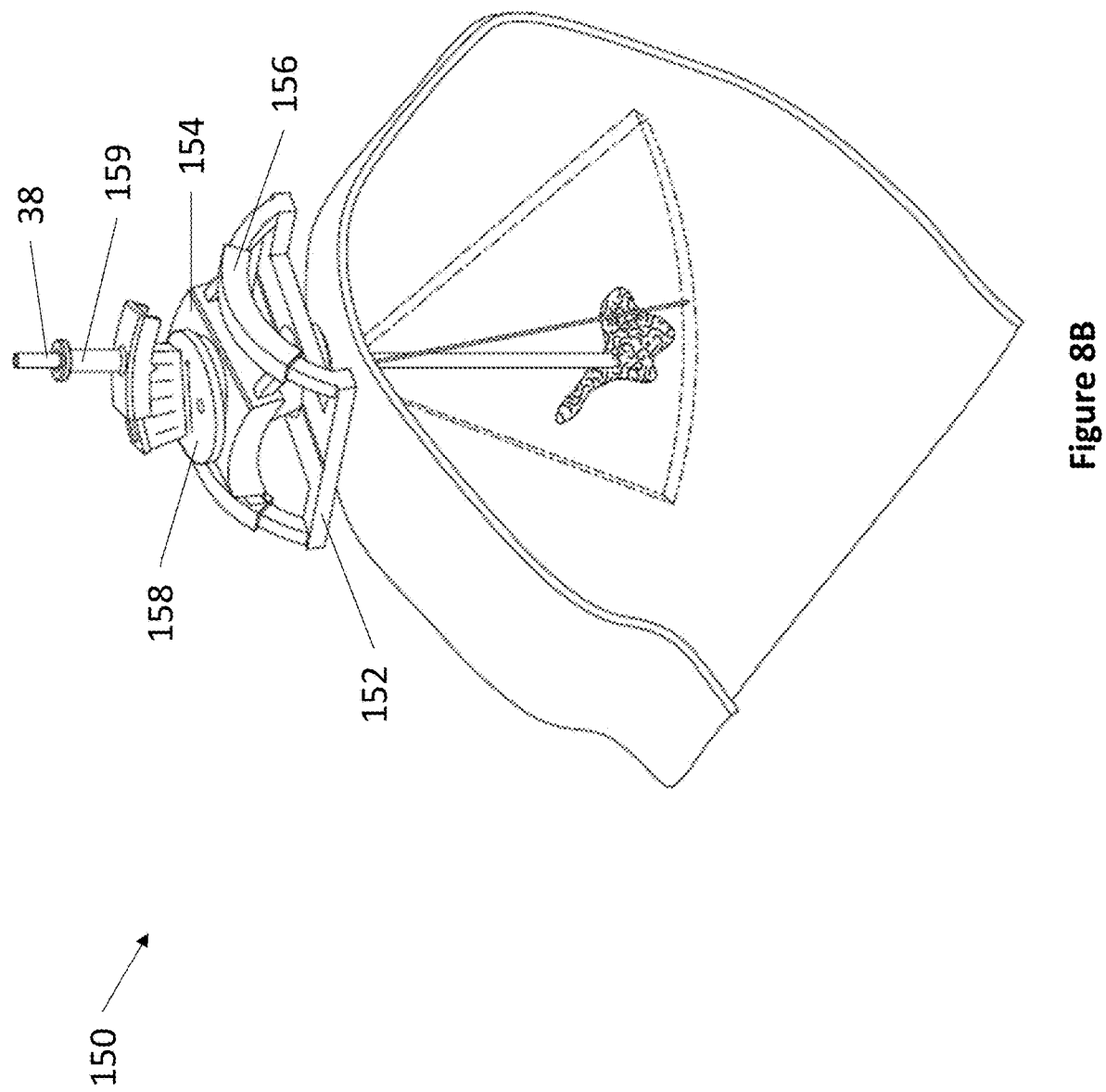

Referring now to FIG. 8A and FIG. 8B, an exemplary 5 DoF fixation device 150 is depicted. Device 150 comprises cranial interface component 152, anterior-posterior angle control 154, lateral angle control 156, transducer housing 158, and lever 159. Cranial interface component 152 is at least partially secured into a burr hole. Cranial interface component 152 features a frame and at least two angular rails for guiding the movement of anterior-posterior angle control 154. Anterior-posterior angle control 154 in turn comprises at least two angular rails for guiding the movement of lateral angle control 156. Lateral angle control 156 comprises a space at its center for accepting transducer housing 158. Transducer housing 158 comprises at least one ultrasonic transducer located within a conical region that fits within cranial interface component 152, wherein the conical region serves as a pivot point while the orientation of transducer housing 158 is adjusted. Transducer housing 158 comprises a lever housing, whereupon lever 159 actuates. The lever housing may comprise regularly spaced markings to indicate the relative position of lever 159. In various embodiments, lever 159 may be angled between 5 and 15 degrees from vertical. Lever 159 comprises at least one aperture for accepting a medical instrument 38. The first DoF of device 150 is the vertical travel of medical instrument 38. The second DoF of device 150 is the angulation of lever 159. The third DoF of device 150 is the rotation of transducer housing 158. The fourth DoF of device 150 is the angulation of lateral angle control 156. The fifth DoF of device 150 is the angulation of anterior-posterior angle control 154.

Referring now to FIG. 9A through FIG. 9D, an exemplary compact 4 DoF fixation device 160 is depicted. Device 160 comprises anchor 162, hemispheric cap 164, and transducer housing 166. Anchor 162 is at least partially secured into a burr hole and comprises a hemispheric top with track 168 on its surface, track 168 spanning the diameter of anchor 162. Hemispheric cap 164 sits on top of anchor 162 and moves along track 168. Hemispheric cap 164 comprises track 169 on its surface, track 169 being perpendicular to track 168 and spanning the diameter of hemispheric cap 164. Both anchor 162 and hemispheric cap 164 comprise an open space at their centers to fit transducer housing 166. Transducer housing 166 sits on top of hemispheric cap 164 and moves along track 169. Transducer housing 166 comprises at least one ultrasonic transducer and at least one aperture for accepting a medical instrument 38.

In various embodiments, the fixation devices of the present invention may be sterilized or autoclaved. In certain embodiments, the fixation devices of the present devices may be partially disposable. For example, certain components enclosing transducers 22 and any associated circuitry and electronics may be detachable and cleaned between uses, while other components may be discarded and replaced between uses.

The fixation devices of the present invention can be combined with additional components to facilitate their use in various applications. The additional components may include features that help automate the use of the fixation devices, such as actuators for mechanical movement and adjustment of the fixation device. The actuators may comprise position sensors to record positional orientations of the fixation device. For example, the fixation devices of the present invention may further include encoders, multi-degree of freedom mems devices (e.g., Bosch BNO055 9 degrees of freedom absolute orientation sensor), or any other suitable device for sensing, communicating, and recording data relating to the position, angle, and rotation of the transducer. In some embodiments, the position, angle, and rotation data may be mapped to a specific image set to correspond to the orientation of the fixation device when the image set was taken. The position, angle, and rotation data may be used to generate a 3D map from a series of image sets, to calculate volume rendering, to determine orientation parameters for a particular angle of entry, and the like. In certain embodiments, the sensing, communicating, and recording may be activated and deactivated by a remote switch, such that a user may choose when to begin and when to terminate the collection of location data. The remote switch enables a user to capture data in an efficient manner. The positional data may, for example, be later conveyed to the actuators such that a fixation device may quickly reacquire the positional orientation needed to find a target site, with subsequent emissions from the transducers to confirm accurate targeting.

In one embodiment, the additional component is an anchoring patch. For example, as depicted in FIG. 10A, cup locking assembly 30 may be adhered to anchoring patch 52 to form fixation device patch 50. Fixation device patch 50 is useful in applications where guided accurate insertion of medical instruments is required but the surrounding tissue is too soft to secure a cup locking assembly 30. As shown in FIG. 10B, anchoring patch 52 provides cup locking assembly 30 with a stable substrate to anchor into. Cup locking assembly 30 is then able to image, for example, the interior of the calf between the tibia and the fibula and accurately insert medical instrument 38 as depicted in FIG. 10B.

Anchoring patch 52 may be made from any suitable material, including plastics, polymers, metals, gels, and the like. In one embodiment, anchoring patch 52 may be flexible. In another embodiment, anchoring patch 52 may be rigid. Anchoring patch 52 may comprise an adhesive on the surface that contacts a patient. Cup locking assembly 30 may be adhered to anchoring patch 52 in any suitable way, such as by an adhesive or by friction. In one embodiment, anchoring patch 52 may comprise a rigid housing having features such as screw threads, clips, latches, and the like to connect to cup locking assembly 30.

In some embodiments, the devices of the present invention may operate in conjunction with a computer platform system, such as a local or remote executable software platform, or as a hosted internet or network program or portal. In certain embodiments, portions of the system may be computer operated, or in other embodiments, the entire system may be computer operated. As contemplated herein, any computing device as would be understood by those skilled in the art may be used with the system, including desktop or mobile devices, laptops, desktops, tablets, smartphones or other wireless digital/cellular phones, televisions or other thin client devices as would be understood by those skilled in the art.

The computer platform is fully capable of sending and interpreting device emissions signals as described herein throughout. For example, the computer platform can be configured to control emissions parameters such as frequency, intensity, amplitude, period, wavelength, pulsing, and the like, depending on the emissions type. The computer platform can also be configured to control the actuation of the device, such as angulation and partial locking. The computer platform can be configured to record received emissions signals, and subsequently interpret the emissions. For example, the computer platform may be configured to interpret the emissions as images and subsequently transmit the images to a digital display. The computer platform may further perform automated calculations based on the received emissions to output data such as density, distance, temperature, composition, imaging, and the like, depending on the type of emissions received. The computer platform may further provide a means to communicate the received emissions and data outputs, such as by projecting one or more static and moving images on a screen, emitting one or more auditory signals, presenting one or more digital readouts, providing one or more light indicators, providing one or more tactile responses (such as vibrations), and the like. In some embodiments, the computer platform communicates received emissions signals and data outputs in real time, such that an operator may adjust the use of the device in response to the real time communication. For example, in response to a stronger received emission, the computer platform may output a more intense light indicator, a louder auditory signal, or a more vigorous tactile response to an operator, such that the operator may adjust the device to receive a stronger signal or the operator may partially lock the device in a position that registers the strongest signal. In a further example, the computer platform may display image overlays to represent an inserted medical device in relation to a displayed ultrasound image or volume rendering (3D reconstruction) on screen.

In some embodiments, the computer platform is integrated into the devices of the present invention. For example, in some embodiments, at least one component of the computer platform described elsewhere herein is incorporated into a fixation device of the present invention, such as emissions parameter controlling means, emissions recording and interpretation means, communication means for the received emissions and data outputs, and one or more features for displaying the received emissions, data, and images. Fixation devices having at least one integrated computer platform component may be operable as a self-contained unit, such that additional computer platform components apart from the device itself are not necessary. Self-contained units provide a convenient means of using the devices of the present invention by performing a plurality of functions related to the devices. Self-contained units may be swappable and disposable, improving portability and decreasing the risk of contamination.

The computer operable component(s) may reside entirely on a single computing device, or may reside on a central server and run on any number of end-user devices via a communications network. The computing devices may include at least one processor, standard input and output devices, as well as all hardware and software typically found on computing devices for storing data and running programs, and for sending and receiving data over a network, if needed. If a central server is used, it may be one server or, more preferably, a combination of scalable servers, providing functionality as a network mainframe server, a web server, a mail server and central database server, all maintained and managed by an administrator or operator of the system. The computing device(s) may also be connected directly or via a network to remote databases, such as for additional storage backup, and to allow for the communication of files, email, software, and any other data formats between two or more computing devices. There are no limitations to the number, type or connectivity of the databases utilized by the system of the present invention. The communications network can be a wide area network and may be any suitable networked system understood by those having ordinary skill in the art, such as, for example, an open, wide area network (e.g., the internet), an electronic network, an optical network, a wireless network, a physically secure network or virtual private network, and any combinations thereof. The communications network may also include any intermediate nodes, such as gateways, routers, bridges, internet service provider networks, public-switched telephone networks, proxy servers, firewalls, and the like, such that the communications network may be suitable for the transmission of information items and other data throughout the system.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a manager, expert, researcher, or other professional of the particular results. Further embodiments of such mechanisms are described elsewhere herein or may standard systems understood by those skilled in the art.

Methods of Use

The invention provides methods for using the fixation device and locking assemblies of the present invention. The methods of using the fixation device and locking assemblies provide accurate insertion of various medical devices by providing detection means of a patient's internal anatomy and at least partially locking the orientation and position of the fixation device.

Figure 11:
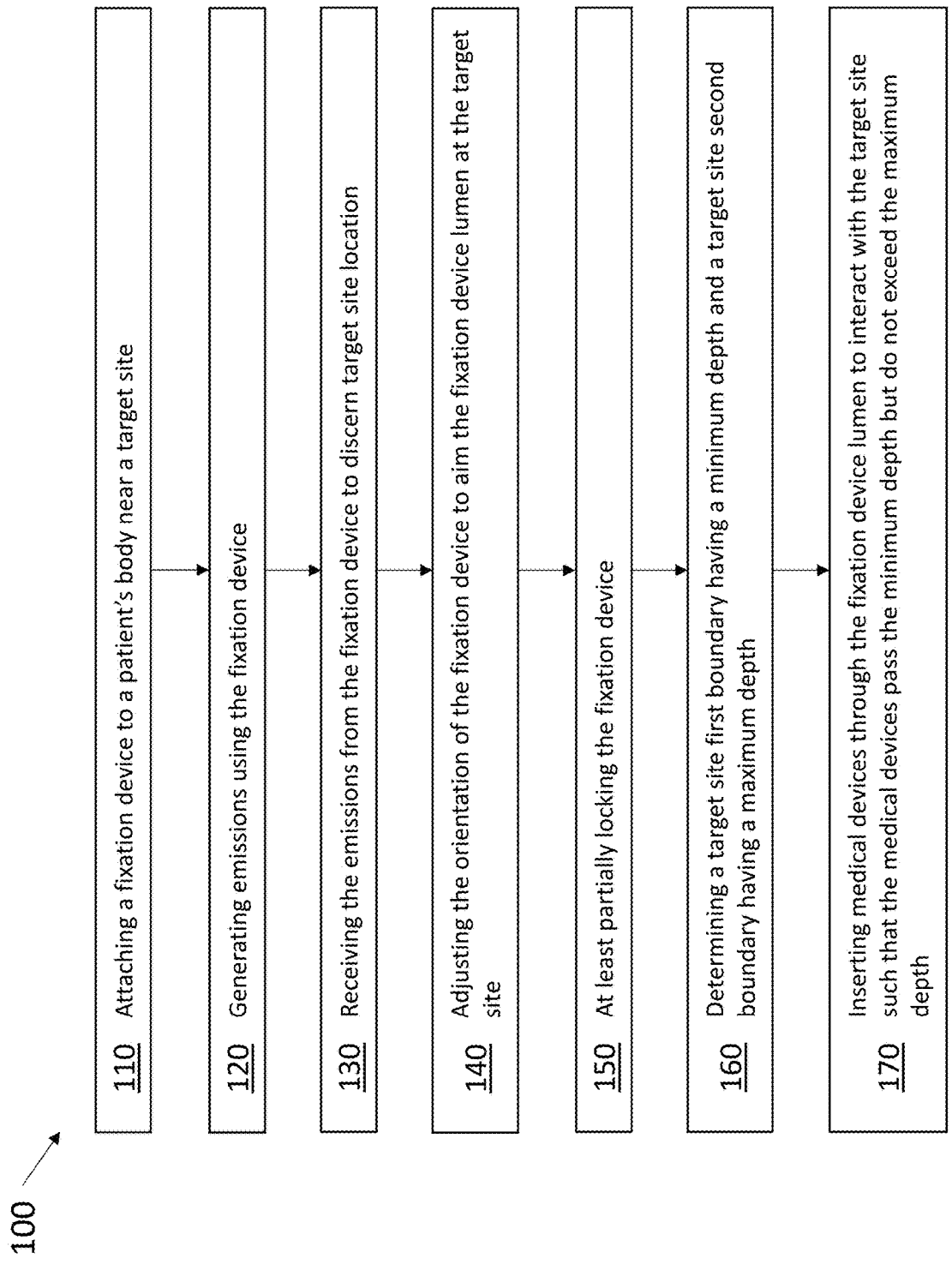
FIG. 11 is a flowchart for an exemplary method of using a fixation device.

In one embodiment, a single fixation device with transducers having energy emission means and energy reception means is used to provide detection means of a patient's internal anatomy for the accurate insertion of medical devices. Referring now to FIG. 11, an exemplary method 100 begins with step 110 of attaching a single fixation device to the patient's body near a target site within the patient's anatomy. In step 120, the single fixation device generates emissions, and in step 130, at least some emissions are received by the single fixation device to determine the location of the target site within the patient's anatomy. In step 140, the orientation of the single fixation device is adjusted such that the lumen of the fixation device is pointed at the target site, and in step 150, the single fixation device is at least partially locked. In step 160, a target site first boundary having a minimum depth is determined, and a target site second boundary having a maximum depth is determined. Finally, in step 170, medical devices may then be accurately inserted through the single fixation device lumen to interact with the target site as needed, wherein the medical devices pass the minimum depth but do not exceed the maximum depth.

Figure 12B:
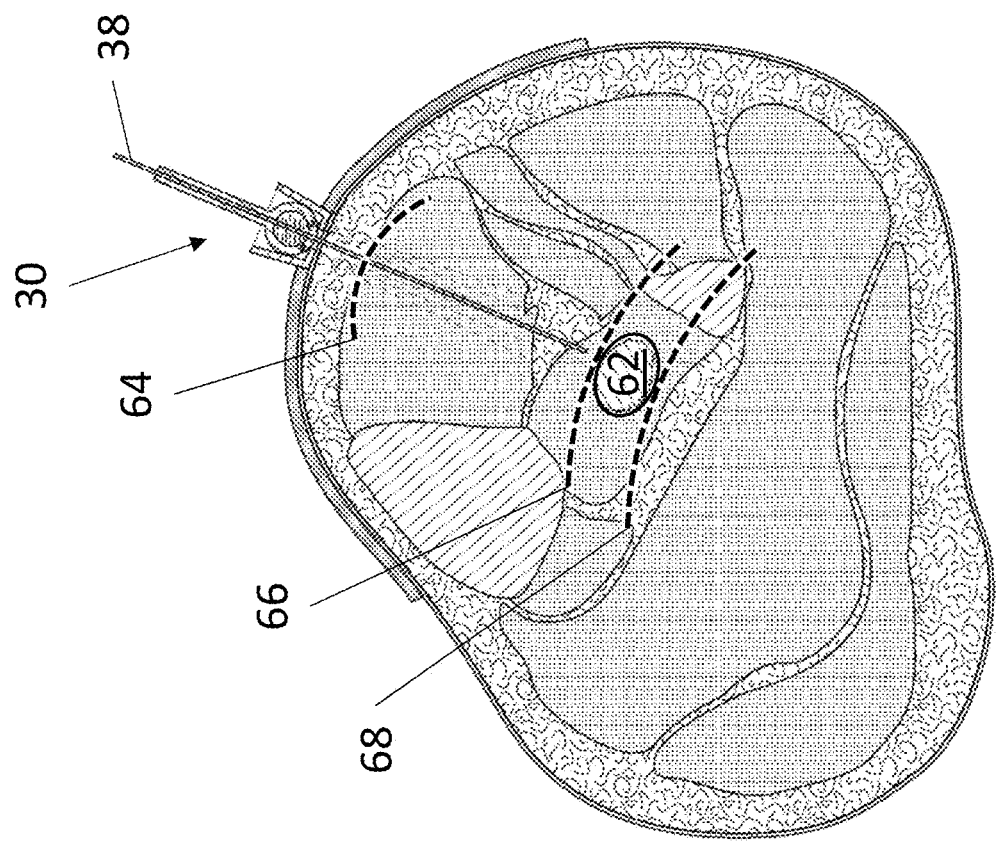
FIG. 12A and FIG. 12B depict an exemplary method of using a fixation device for accurate depth determination.
Figure 12A:
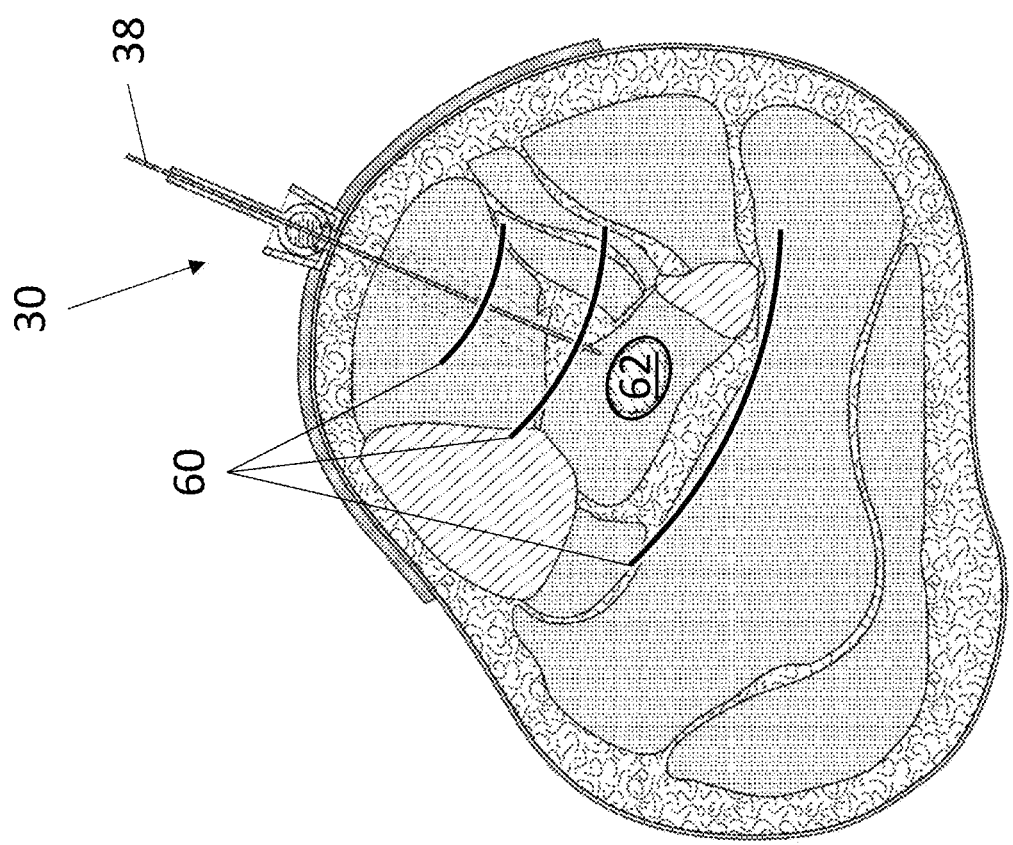

Referring now to FIG. 12A and FIG. 12B, the method step of determining a target site first boundary and a target site second boundary is depicted. In FIG. 12A, a plurality of emissions 60 are emitted from fixation device 30 in the direction of target site 62. In FIG. 12B, at least a portion of the plurality of emissions 60 are reflected back and received by fixation device 30. For example, reflected emission 64 indicates the depth of a fat-muscle boundary interface. Reflected emission 66 indicates the depth of the target site first boundary having a minimum depth, which is the location of the target site that is closest to fixation device 30. Reflected emission 68 indicates the depth of the target site second boundary having a maximum depth, which is the location of the target site that is furthest from fixation device 30. Medical device 38 may then be inserted into target site 62 with accuracy by passing the minimum depth and not exceeding the maximum depth.

In some embodiments, depth of insertion may be determined by measuring the length of medical device 38 as it passes through fixation device 30. Medical device 38 will have reached the correct depth once the measured length is between the minimum depth and the maximum depth. In other embodiments, depth of insertion may be determined using a medical device having an ultrasonic reflective material. For example, a medical device having an ultrasonic reflective material at its distal end can have its distance from fixation device 30 continually monitored such that the medical device will have reached the correct depth once fixation device 30 detects that the ultrasonic reflective material is located between the minimum depth and the maximum depth.

In one embodiment, one or more fixation devices are used to provide detection means of a patient's internal anatomy for the accurate insertion of medical devices. For example, one or more fixation devices are attached to the exterior of a patient's body near a target site within the patient's anatomy. In one embodiment, the transducers of the one or more fixation devices may comprise both energy emission means and energy reception means. In another embodiment, at least one fixation device comprises transducers with emission means while the remaining fixation devices comprise transducers with reception means. In another embodiment, at least one fixation device comprises transducers with reception means while the remaining fixation devices comprise transducers with emission means.

In one embodiment, one or more fixation devices are used to map the internal anatomy of a patient in three dimensions. The fixation devices are useful in stereotactic mapping and stereotactic surgery. For example, one or more fixation devices are attached to the exterior of a patient's body, whereupon energy emission and reception determines the internal anatomy of the patient and maps it in three dimensions. The mapping data can be interpreted using a coordinate system, and surgery may be performed upon precise coordinates using the devices and methods of the present invention.

Figure 13:
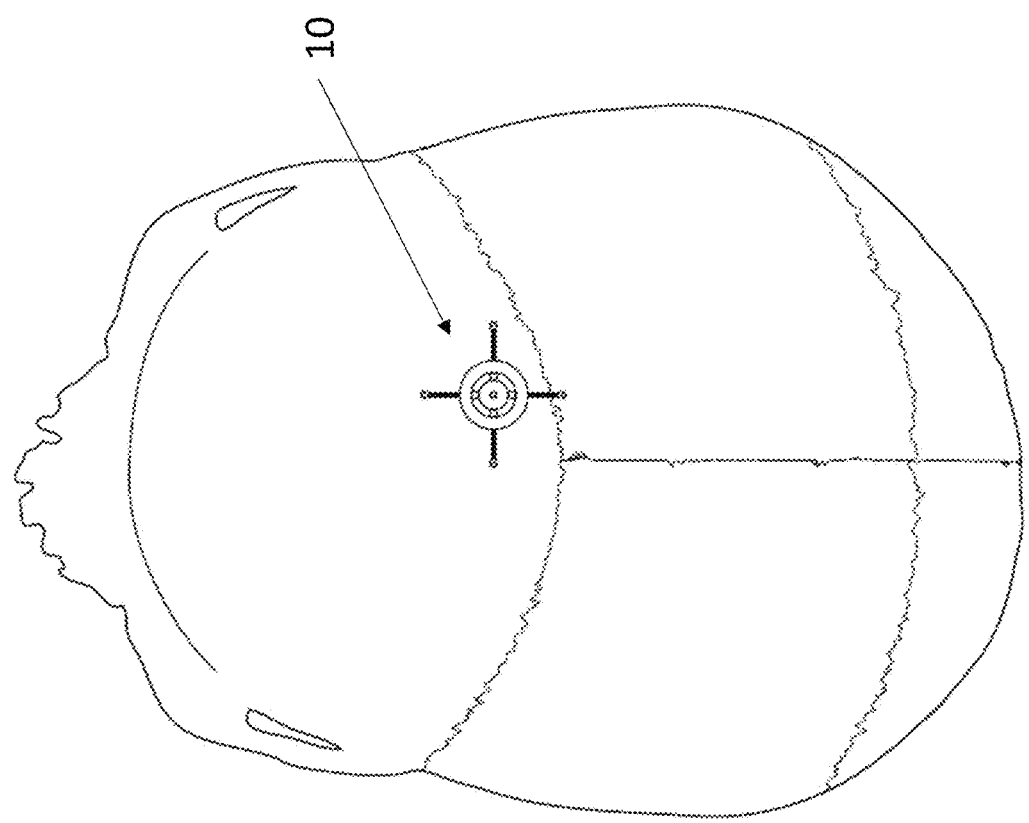
FIG. 13 depicts a top-down view of a skull with a fixation device inserted at Kocher's point.

In one embodiment, the invention provides methods for inserting an external ventricular drain (EVD) into a patient using a fixation device and a grommet locking assembly. The grommet locking assembly may be inserted into a burr hole in the skull, preferably at Kocher's point (FIG. 13), approximately 10 cm along the sagittal axis as measured from the nasion and 3 cm laterally towards the right or left ear. The grommet locking assembly spans the thickness 24 of the skull (FIG. 2B). Ultrasound imaging is performed using the ultrasonic transducers located in the fixation device to determine the brain's anatomy, including location and depth. An operator may vary the orientation of the fixation device such that the fixation device is aimed at the right lateral ventricle, preferably the frontal horn of the right lateral ventricle. The operator may then at least partially lock the fixation device in place by actuating the at least one locking member so that the grommet locking assembly maintains the aim of the fixation device at the frontal horn of the right lateral ventricle. An operator may then determine a first boundary of the right lateral ventricle closest to the fixation device having a minimum depth and a second boundary of the right lateral ventricle furthest from the fixation device having a maximum depth. The operator may then insert a drainage catheter into the frontal horn of the right lateral ventricle by guiding the catheter into the lumen of the at least partially locked fixation device such that the drainage catheter passes the minimum depth but does not exceed the maximum depth. In one embodiment, the drainage catheter may be fitted with an ultrasonic reflective strip for enhanced visualization of the catheter.

In another embodiment, the invention provides methods for inserting an EVD into a patient using a fixation device and a cup locking assembly. For example, a cup may be first inserted into a burr hole in the skull, preferably at Kocher's point (FIG. 13), approximately 10 cm along the sagittal axis as measured from the nasion and 3 cm laterally towards the right or left ear. The cup spans the thickness 24 of the skull (FIG. 4). The fixation device with ball adapter is then inserted into the cup, and ultrasound imaging is performed using the ultrasonic transducers located in the fixation device to determine the brain's anatomy, including location and depth. An operator may vary the orientation of the fixation device such that the fixation device is aimed at the right lateral ventricle, preferably the frontal horn of the right lateral ventricle. The operator may then at least partially lock the fixation device in place by actuating the at least one locking member so that the cup locking assembly maintains the aim of the fixation device at the frontal horn of the right lateral ventricle. An operator may then determine a first boundary of the right lateral ventricle closest to the fixation device having a minimum depth and a second boundary of the right lateral ventricle furthest from the fixation device having a maximum depth. The operator may then insert a drainage catheter into the frontal horn of the right lateral ventricle by guiding the catheter into the lumen of the at least partially locked fixation device such that the drainage catheter passes the minimum depth but does not exceed the maximum depth. In one embodiment, the drainage catheter may be fitted with an ultrasonic reflective strip for enhanced visualization of the catheter.

In certain embodiments, the present invention provides methods of using the fixation devices of the present invention in conjunction with imaging software, wherein the imaging software acquires ultrasound images of the body to form real-time three dimensional display models from the reconstruction of gathered image data sets (FIG. 14A, FIG. 14B). The ultrasound transducer portion of a fixation device is controllably moved to image the anatomy of the body (FIG. 15A through FIG. 15F). While the fixation device is moved, position, angle, and rotation data relative to the fixation device are collected for each image (such as via a mems sensor) to generate a three-dimensional model. The combination of the 3D data and the position, angle, and rotation data allows a physician to determine the ideal trajectory and stopping point of an inserted medical instrument into the body. Upon selection of target coordinates, a computer, attached by either wired or wireless means to the fixation device, will calculate the correct orientation of the individual components of the fixation device, assuring precise and efficient placement of the medical instrument. In some embodiments, the fixation device further comprises one or more motors, such that the computer may further automatically adjust the orientation of the fixation device to match the selected target coordinates.

In some embodiments, the methods of using the fixation devices in conjunction with imaging software are suitable for placing ventricular catheters. As described elsewhere herein, the fixation devices incorporate at least one ultrasound transducer component capable of selectively moving its sonic energy wave front. In some embodiments, the sonic energy wave front can be moved in a pivoting manner such that the axis of rotation is parallel to the face of the transmission surface. The sonic energy wave front is moved along, and normal to, a given plane face such as the sagittal or coronal planes of the brain, wherein "normal" is referred to in the geometric sense as perpendicular to a line tangential to the skull. The sonic energy wave front can also be rotated about a fixed axis that is generally oriented in an axial direction, normal to the ultrasound transducer transmission face; rotating in this manner causes the sonic energy wave front to cross the sagittal plane, the coronal plane, or both. As the transducer is either pivoted or spun about an axis of rotation, encoders mounted in the fixation devices are capable of providing real-time positional (rotational and angular information) of the transducer's position. The positional information of the transducer face angle, referenced from a starting zero position, is combined with the associated image pixel data acquired at that specific point of data collection in space and time. In some embodiments, the fixation devices also provide real-time positional data of the inserted medical instruments.

It should be appreciated that movement of the transducers to capture imaging and positional data is not limited to a single rotation. For example, the transducers may be actuated in a single sweeping direction. The transducers may also be actuated in more than once rotation, or more than one sweeping direction. The transducers may also be actuated in a combination of one or more rotations and one or more sweeping directions. Using a sweeping actuation, volumetric image formation can be obtained by sequential anterior to posterior translation of a transducer relative to a subject. In the context of imaging a brain, a sweep of the transducer may be performed in the sagittal plane to render a three dimensional image of a desired structure. If, for instance, an object of interest is not represented in the sagittal sweep, the transducer can be translated along the coronal plane and a repeated anterior to posterior sweep of the transducer can be made to obtain the volumetric image of the desired structure.

Referring now to FIG. 16, an exemplary method 200 of using a fixation device of the present invention to insert a ventricular catheter is depicted. Method 200 begins with step 202, wherein the skin is marked at Kocher's point above a subject's skull. Typically, Kocher's point is located with reference to the point between the subject's pupils, known as the nasion. A 10 cm line is drawn from the nasion along the skull in a posterior direction to the occiput. At the endpoint of the 10 cm line, a 3 cm line is drawn laterally towards the left or right ear. The endpoint of the 3 cm line is roughly Kocher's point. In step 204, an incision is made at the marked skin. The incision is preferable large enough to accommodate a fixation device of the present invention. Hemostasis should be established. To provide easier access to the skull, the skin may be spread with a retraction device. In step 206, the skull is perforated. The skull may be perforated using any suitable drill bit. In some embodiments, it is recommended not to exceed 800 RPM when drilling. In step 208, a fixation device of the present invention having ultrasonic transducers is inserted into the skull perforation. In step 210, the ultrasonic transducers are aligned to capture a cross-sectional ultrasound image of the brain with the positional, angular, and rotational orientation of the ultrasonic transducers. In step 212, the ultrasonic transducers are actuated. In step 214, a series of ultrasonic images of the brain and associated positional, angular, and rotational orientation of the ultrasonic transducers are acquired during actuation. Typically, anechoic regions visible in the ultrasonic images represent the brain ventricles. In step 216, the ultrasonic images are assembled to form a 3D reconstruction of the brain ventricles using the associated positional, angular, and rotational orientation of the ultrasonic transducers. In step 218, an automatic segmentation of the 3D reconstruction is performed to isolate an anatomy of interest. The 3D reconstruction and segmentation views can be displayed from multiple angles, such as from a sagittal, coronal, and axial plane view, as well as a 3D view. Any suitable software can be used to generate the views, such as Osirix, ITK-Snap, 3D-Slicer, and Mimics. In step 220, the positional, angular, and rotational orientation of the anatomy of interest are acquired. The location can be confirmed on the 3D reconstruction and segmentation views. In step 222, the fixation device is aligned to target the anatomy of interest. In step 224, the alignment of the fixation device is fixed relative to the skull. In step 226, a catheter and ventricular drain are inserted through the fixation device into the anatomy of interest. In some embodiments, the ultrasonic transducers may be activated to monitor the entry of the catheter and ventricular drain. For example, out-of-plane imaging using the ultrasonic transducers can verify accurate catheter and ventricular drain insertion. In step 228, the fixation device is removed over the catheter and ventricular drain.

With reference now to FIG. 35, a anchor bolt 300 with raised pillars 306 is shown according to one embodiment. The anchor bolt 300 includes a threaded portion 302 that is designed to screw the anchor bolt 300 into a perforation formed in a patient's skull. A top portion 304 of the anchor bolt 300 is configured to connect to and anchor a PID guide and an ultrasound probe assembly. The anchor bolt, PID guide and ultrasound probe assembly can be considered components of a PID system. The threaded portion 302 and top portion 304 are separated by raised pillars 306 to form an opening 308 and allow for access to a treatment device, such as an EVD. In certain embodiments, the opening 308 can be used to access and fixate the EVD while the PID guide is being removed (see for example the method 500B described below). As shown in the alternative embodiment of FIGS. 36A-C, the bolt anchor 310 can include a base 316 having multiple spikes 312 for improved fixation to the skull. In certain embodiments, the spikes 312 are disposed circumferentially or in pairs about the center opening of the bolt anchor 310. In certain embodiments, holes 314 are formed in the base 316 for the insertion of bone screws that can thread into the scull. In certain embodiments, the holes 314 are disposed circumferentially or in pairs about the center opening, or are alternating between spikes in the base 316. In one embodiment, an anchor bolt includes a circumferential bone attachment portion, a circumferential raised attachment portion, and a pillar member forming an opening therebetween. In one embodiment, the pillar member includes a plurality of separated pillar members. In one embodiment, the skull attachment portion includes a threaded surface.

With reference now to FIGS. 37A-D, an ultrasound probe assembly 400 having a retractable ultrasound probe 402 is shown according to one embodiment. The ultrasound probe assembly 400 includes a housing 401, an ultrasound probe 402 and a guide tube 410. In certain embodiments, the probe 402 is retracted and deployed using a proximal dial mechanism 406. During a procedure, the proximal dial mechanism 406 can be used to retract the probe 402 from the burr hole. A proximal dial mechanism 406 can also be used for fine adjustment of the probe 402 once inserted from the PID guide onto the dura. This allows for contact with the dura and image optimization. In one embodiment, a series of gears 408 is disposed at the base of the probe 402 that will allow for the probe 402 to be adjusted perpendicular to the probe housing or the dura surface, such as by the proximal dial mechanism 406 or a separate mechanism. Otherwise, if the adjustment were direct (i.e. along the trajectory of the probe), this may cause the probe to make contact with the inner table of the skull. According to the embodiment shown, the EVD 412 is placed from the center 404 of the ultrasound probe assembly 400 via the EVD guide tube 410 extending through the middle of the ultrasound probe assembly 400. This embodiment minimizes the risks associated with the EVD being placed from an offset and angled approach, instead allowing a more direct advancement towards the target treatment location. This embodiment further minimizes the risk of angulation of the PID causing contact with the inner or outer table of the skull. The central axis of the guide tube forms an acute angle with the ultrasound transducer as shown in FIG. 37B. As shown specifically with reference to FIG. 37D, when the probe is retracted, it is also moved off to the side to allow the EVD to advance from the center of the probe assembly. This will translate to the EVD entering in the middle of the burr hole thus minimizing the risk of the EVD making contact with the inner or outer tables of the skull. In one embodiment, an ultrasound probe assembly includes a housing forming a guide tube extending therethrough, a retractable ultrasound probe, and a distal attachment portion. In one embodiment, the ultrasound probe is configured to move towards a central axis of the guide tube during extension. In one embodiment, the ultrasound probe is configured to move away from a central axis of the guide tube during retraction. In one embodiment, the ultrasound probe assembly includes a retractable ultrasound probe that moves along a first axis, and a guide tube having a central axis, where the first axis and the central axis are non-parallel. In one embodiment, the first axis and the central axis intersect to form an acute angle. In one embodiment, the first axis and the central axis intersect to form an angle of less than 45 degrees. In one embodiment, the ultrasound probe assembly includes a proximal control configured to retract and extend the probe. In one embodiment, the ultrasound probe assembly includes a control configured to move a tip of the probe along a lateral plane. In one embodiment, the retractable probe assembly includes a linear encoder. In one embodiment, the retractable probe assembly includes a magnetic encoder.

Advantageously, embodiments of the ultrasound probe can overcome the limited space for both ultrasound probe and EVD to occupy the typically 11 mm hole left by the drill. This avoids the safety implications of vectors that displace the EVD from the intended location which could impose a safety risk to the patient. Further, The hole that is produced by the drill is typically not symmetric, and there are fragments of bone that are left after removal of the bone pad. This limits the rotation and angulation of the probe and could interfere with the trajectory of the EVD if a bone fragment displaced the EVD in route to target. The embodiment described above allows the EVD to enter in the middle of the burr hole, avoiding this safety issue.

With reference now to FIGS. 38A and B, in one embodiment, a linear encoder 420 will read the EVD 412 (or an EVD stylet) as it is inserted and advanced through the EVD guide tube 410. In certain embodiments, the EVD or an EVD stylet is encoded with magnetic tape. In certain embodiments, the linear encoder 420 is a magnetic encoder that will read linear magnetic tape as it passes through the probe assembly to give the user real time information of the location of the EVD 412 as it advances towards the target. This can be represented on the user interface in coordination with the 3D rendered ventricles. Linear encoders 452 and rotary encoders 454 can also be positioned on the PID guide 450 for precision motion control, as shown in FIGS. 39A-C according to one embodiment. The linear encoders 452 respond to motion along a path, while the rotary encoders 454 respond to rotational motion. In certain embodiments, the encoder determines a position (or direction) based on the scale it is detecting (e.g. a magnetic tape) and outputs a signal indicating the position (or direction), in either analog or digital format, to a controller. The encoders may use optical, magnetic, capacitive or inductive principles to generate an output signal. In one embodiment, the encoders are magnetic linear and rotary encoders that use magnetic tape to determine position. In one embodiment, a guide includes an opening, a first portion configured to attach to the circumferential raised attachment portion of the anchor bolt, a second portion configured to attach to the distal attachment portion of the ultrasound probe assembly, and a first and second encoder. In one embodiment, the guide includes a coronal plane adjustment mechanism. In one embodiment, the guide includes a sagittal plane adjustment mechanism. In one embodiment, the first encoder is a coronal encoder. In one embodiment, the second encoder is a sagittal encoder. In one embodiment, the first encoder is a linear encoder. In one embodiment, the second encoder is a rotary encoder.

With reference now to FIG. 40, a flowchart of an exemplary method 500A of positioning a PID system for insertion of an EVD is shown according to one embodiment. First, to mark the skin 502, a point is located between the pupils in the midline (Nasion), and a 10 cm line is drawn from the Nasion along the skull heading posterior to the occiput (see for example FIG. 17). From this line (midline), a point is located 3 cm lateral and marked. An incision is made 504 large enough to accommodate the device at Kocher's point. Hemostasis should be obtained, then the skin can be spread with a retraction device (see for example FIG. 18). Then, the skull is perforated with a power drill 506, such as a 5-8 mm twist drill. In certain embodiments, the drill has a non-clogging geometry (e.g. fluted surfaces) to remove bone chips from the hole, as well a non-skid tip (see e.g. Acra Cut Smart Drill Model 200-500). Next, the pillared anchor bolt 550 is threaded into the hole and secured to the scull 508. Various embodiments of either the threaded anchor bolt 550 (FIGS. 42A and 42B) or the spiked pillared anchor bolt 550' (FIG. 43) described above can be used. The PID guide 552 is then be inserted and connected to the pillared anchor bolt 550, aligning the PID guide 552 in the coronal plane, towards the ear and locking into place on the pillared anchor bolt 550 with a locking pin/bolt portion of the PDI guide 510 (FIG. 44). As shown in FIG. 45, an encoder based PID guide 552' and spiked pillared anchor bolt 550' can be used. The PID guide 552 and anchor bolt 550 assembly is shown in FIG. 46. Next, insert the ultrasound transducer of the ultrasound probe assembly 554 containing a second 9dof is inserted into the locked PID guide 552, 512 (FIG. 47). As shown in FIG. 47, an encoder based PID guide 552' can be used. When desired, the ultrasound probe assembly 554 can also be inserted directly into an anchor bolt 550 for imaging the target treatment area as shown in FIG. 49. The fully assembled PID system is shown in FIG. 50. A fully assembled PID system with an encoder based PID guide 552' is shown in FIG. 51. Next the depth of the transducer should be adjusted to make contact with the Dura using the twist knob 558 at the bottom of the ultrasound probe assembly 554, 514. As illustrated in FIG. 52, tilt the transducer into the ideal coronal orientation where the right anterior horn of the lateral ventricle is in the central portion of the real time image by adjusting the angle of the green portion of the PID guide 516. Next, perform a preliminary sweep of the PID in the sagittal direction to confirm proper sagittal orientation 518 (FIG. 53). Confirm the lateral ventricle is located in the center of the ultrasound image 520. Once satisfied with the sagittal orientation, press the "scan button" and sweep in the sagittal anterior-posterior direction until the unit has captured the predetermined number of images at the designated angular increments 522. The capture portion of the scan will complete automatically and the unit will automatically create a 3D reconstruction of the scanned image sequence. This form of auto-segmentation provides a significant advantage over conventional systems. Auto-segmentation applied to the PID system is Updated in real time, and the interaction between the 3D model of the ventricle and the PID/avatar which too is updated in real time (FIG. 54) provides a significant advantage over conventional systems. Dominant images and supportive images can be interchanged with a sign-in process that alters the user interface based upon user's present preferences (see FIG. 55) the software/user interface will allow the user to determine target location and depth prior to EVD insertion (malpositioned catheters shown in FIG. 56). By using the information from the 9dof, encoder and electromagnetic positioning device located on the PID, an avatar (overlay) image of the PID is projected over the 3D image of the reconstructed lateral ventricle (FIG. 57). The position of the avatar overlay correlates in real time to the position of the actual PID and as a result, the trajectory of the EVD. Utilizing the avatar representation allows the practitioner to move the PID guide into final align with the target at which time the PID is then locked into place in real time. Thus, the image capture and positioning process can be summarized in one embodiment as including the steps of determining the position of the transducer/PID using 2d scanning, sweeping the transducer form anterior to posterior, auto-segmenting the region of interest (e.g. the ventricle) using positioning data from the 9dof/encoder/electromagnetic device. Movement of the PID/transducer will update the region of interest model (e.g. the 3d ventricle). This 3D real time updates with the movement of the transducer and will simultaneous update the position of the PID/avatar within the user interface.

With reference now to FIG. 41, a flowchart of an exemplary method 500B of placing an EVD is shown according to one embodiment. A distance D from the transducer face 570 to the entrance opening of the EVD guide 580 is determined 528 (FIG. 58). This distance D is constant (i.e. the PID will move up and down a few mm with rotation of the dial, but will move as a unit). The distance D' from the transducer to the anterior horn of the ipsilateral ventricle is determined (FIG. 59), and added to the distance D from the transducer face 570 to the entrance opening of the EVD guide 580, 528. Next, the distance from transducer to target D' added to the distance from the opening of the EVD guide on the PID D is determined and marked M on the EVD 590 as measured from the functional tip of the EVD (FIG. 60) 530. The transducer is switched on to provide out of plane imaging of the EVD entering the ventricle (FIG. 61). The EVD 590 is then inserted up to the mark M 532 (FIG. 62). The practitioner can also confirm proper placement (FIG. 63) 534 with real time ultrasound image guidance information. Next, the practitioner can grab the EVD 590 with non-penetrating forceps 560 through the opening in the pillared anchor bolt 550 and subgaleal tunnel of EVD 590, 536 (FIG. 64). Once the EVD 590 is secure, the practitioner removes the ultrasound probe assembly 554 over the EVD 590, 538. Next, with the EVD still secure (FIG. 65A), the PID guide 552 is removed over the EVD 590, 540 (FIG. 65B). Finally, the pillared bolt 550 can be removed over the EVD 590, 542 (FIG. 66).

In one embodiment, a method for imaging a region of interest includes the steps of perforating a bone, inserting an anchor bolt into the perforation, connecting a guide onto the anchor bolt, connecting an ultrasound probe assembly including an ultrasound transducer onto the guide, adjusting the depth of the ultrasound transducer, performing a sweep of the region of interest to confirm proper orientation; and retracting the ultrasound transducer.

In one embodiment, a method for imaging a region of interest includes the steps of perforating a bone, inserting an anchor bolt into the perforation, connecting a guide onto the anchor bolt, connecting an ultrasound probe assembly including an ultrasound transducer onto the guide, adjusting the depth of the ultrasound transducer, tilting the ultrasound transducer into a coronal orientation where the right anterior horn of the lateral ventricle is in the central portion of the real time image by performing a preliminary sweep in a sagittal direction to confirm proper sagittal orientation, confirming a lateral ventricle is located in a center of an ultrasound image; and sweeping in a sagittal anterior-posterior direction.

In one embodiment, a method for placing a catheter includes the steps of performing the steps of the method for imaging a region of interest; inserting a catheter; and confirming proper placement with a real time ultrasound image. In one embodiment, the method includes the steps of immobilizing the catheter through an opening in the anchor bolt; and removing the ultrasound probe assembly, guide and anchor bolt over the catheter.

An important aspect of embodiments described herein that separates this system and method from conventional systems and methods is the absence of a need for a specialized CT scan or Mill that must be obtained prior to "matching" with surface landmarks. For example, if a patient was previously admitted to an outside hospital where they had a CT scan or MM, and it was not obtained with the protocol and equipment of the patient's current hospital, the medical professionals at the current hospital would have to repeat the CT scan or MRI according to the protocol and equipment of the patient's current hospital. Once the CT scan or MRI is obtained with the special protocol, the patient is then "matched" using surface landmarks. This entire process is very time consuming, spanning several hours, and the CT scanner and traditional navigation equipment are very expensive. The instant devices, methods and systems described throughout the embodiments combine the imaging, 3D segmentation and navigation steps into one single step that would take less than 5 minutes total. It is easy to understand that if the patient is in extremis, time is of the essence. Additionally, patients are often too sick to travel outside of the ICU and a compact localized and bedside solution provides a great benefit. The ultrasound can obtain 2D images with coordinate data which will allow for segmentation of the 2D images into a 3D structure. The rendered image of the ventricle is what the practitioner will use to determine the path of the EVD. The patient interface device will then be moved into the proper position and the ultrasound probe removed. This will allow for the EVD to be inserted and advanced to the proper location. The software can allow the ultrasound images that are acquired to be "fused" with a CT scan that the patient likely will have prior to admission to the ICU or transferred from another hospital. In one embodiment, the invention provides improved methods for accurate biopsies. For example, a fixation device patch may be adhered to the soft tissue near the desired sample site. Emissions from the fixation device transducers determine the patient's internal anatomy, including structure depth. An operator may vary the orientation of the fixation device such that the fixation device is aimed at the desired sample site. The operator may then at least partially lock the fixation device in place by actuating the at least one locking member so that the fixation device maintains its aim at the desired sample site. The operator may then accurately direct a biopsy needle into the sample site by guiding the biopsy needle into the lumen of the locked fixation device. In one embodiment, the biopsy needle may be fitted with an ultrasonic reflective strip for enhanced visualization of the catheter.

In various embodiments, the invention provides improved methods for accurate insertion of any medical apparatus into the internal anatomy of a patient. The partial locking feature of the invention enables medical apparatuses to be freely interchanged while maintaining positional accuracy to a target site. Examples of procedures that the present invention may be applied to and improve include, but are not limited to: brachytherapy, tracheotomy, localized drug delivery, microsurgery, and the like.

Kits of the Invention

The invention also includes a kit comprising components useful within the methods of the invention and instructional material that describes, for instance, the method of using the fixation devices and locking assemblies as described elsewhere herein. The kit may comprise components and materials useful for performing the methods of the invention. For instance, the kit may comprise a fixation device, a grommet locking assembly, a cup locking assembly, and catheters. In other embodiments, the kit may include separately the transducer components and the locking assemblies, such that the transducer components may be sterilized and reusable, while the locking assemblies may be sterilized and reusable or discarded and replaced. In other embodiments, the kit may further comprise software and electronic equipment to convert received waves into images. The software and electronic equipment may be presented in a compact form for portable use.

In certain embodiments, the kit comprises instructional material. Instructional material may include a publication, a recording, a diagram, or any other medium of expression which can be used to communicate the usefulness of the device described herein. The instructional material of the kit of the invention may, for example, be affixed to a package which contains one or more instruments which may be necessary for the desired procedure. Alternatively, the instructional material may be shipped separately from the package, or may be accessible electronically via a communications network, such as the Internet.

In one embodiment, the invention includes a kit for portable use. To facilitate portable use, a kit of the present invention may further include a razor or clipper for removing hair from a subject, a ruler or tape measure for measuring the location of a site for incision, a surgical marker or other implement for marking the site of incision, skin preparation material (i.e., antiseptic, alcohol pads) to clean the site of incision, a scalpel to perform the incision, a drilling instrument to perforate any bone, and any additional surgical and medical elements that may be useful for such an operation, such as surgical tape, gauze, bandages, surgical thread and needle, and the like.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A patient interface system comprising:
an anchor bolt comprising a circumferential bone attachment portion, a circumferential raised attachment portion, and a pillar member forming an opening therebetween;
an ultrasound probe assembly comprising an ultrasound probe and a distal attachment portion; and
a guide comprising an opening, a first portion configured to attach to the circumferential raised attachment portion of the anchor bolt, a second portion configured to attach to the distal attachment portion of the ultrasound probe assembly, a first encoder configured to generate a first position signal based on a measured position along a first path, and a second encoder configured to generate a second position signal based on a measured position along a second path, wherein each of the plurality of images captured by the ultrasound probe is associated with a set of positions comprising a first position signal and a second position signal, where the ultrasound probe is configured to capture a plurality of images while the second portion is attached to the distal attachment portion; and
a display configured to generate an updated target image while the ultrasound probe assembly is separated from the guide based on the plurality of images captured by the ultrasound probe and the associated set of positions.

2. The patient interface system of claim 1, wherein the pillar member comprises a plurality of separated pillar members.

3. The patient interface system of claim 2, wherein the first path is configured along a coronal plane and the second path is configured along a sagittal plane.

4. The patient interface system of claim 1, wherein the bone attachment portion comprises a threaded surface.

5. The patient interface system of claim 1, wherein the bone attachment portion comprises a plurality of spikes.

6. The patient interface system of claim 1, wherein the bone attachment portion comprises a hole configured to accept a bone screw.

7. The patient interface system of claim 1, wherein the ultrasound probe assembly comprises a control configured to move a tip of the probe along a lateral plane.

8. The patient interface system of claim 1, wherein the first encoder comprises a linear encoder.

9. The patient interface system of claim 1, wherein the first encoder comprises a magnetic encoder.

10. The patient interface system of claim 1, wherein the guide comprises a coronal plane adjustment mechanism.

11. The patient interface system of claim 1, wherein the guide comprises a sagittal plane adjustment mechanism.

* * * * *